United States Patent [19]

Mace et al.

[11] Patent Number: 5,793,044

[45] Date of Patent: Aug. 11, 1998

[54] INFRARED RADIATION DETECTOR UNITS AND METHODS OF ASSEMBLING TRANSDUCERS IN WHICH SAID UNITS ARE INCORPORATED

[75] Inventors: Leslie E. Mace, Mercer Island; Lawrence L. Labuda, Coupeville; Gerald R. Apperson, Seattle; Walter A. Cooke, Monroe; Joseph O. Sams, Bellevue, all of Wash.

[73] Assignee: NTC Technology, Inc., Wilmington, Del.

[21] Appl. No.: 554,898

[22] Filed: Nov. 9, 1995

[51] Int. Cl.$^6$ .................................................. G01N 21/61
[52] U.S. Cl. .......................... 250/343; 250/339.03
[58] Field of Search ..................... 250/338.1, 339.03, 250/352, 343, 345, 339.13, 349, 339.02

[56] References Cited

U.S. PATENT DOCUMENTS

| | | | |
|---|---|---|---|
| 3,813,551 | 5/1974 | Broadbent et al. | 250/338.1 |
| 4,066,364 | 1/1978 | Emerson | 250/343 |
| 4,437,004 | 3/1984 | Passaro et al. | 250/343 |
| 4,543,482 | 9/1985 | Brenholdt | 250/343 |
| 4,755,674 | 7/1988 | Schaaf | 250/338.1 |
| 4,891,519 | 1/1990 | Nohira et al. | 250/343 |
| 5,146,092 | 9/1992 | Apperson et al. | 250/343 |

*Primary Examiner*—Michael J. Tokar
*Assistant Examiner*—Richard Hanig
*Attorney, Agent, or Firm*—Hughes, Multer & Schacht, P.S.

[57] ABSTRACT

A transducer for nondispersive infrared radiation (NDIR) gas analysis and a passive device for verifying the calibration of the transducer. The calibration verification device can be mounted on a cable by which the transducer is attached to an associated signal processing-control-display unit (SPCDU) or monitor. Calibration parameters for the transducer are stored in a plug at the monitor end of the cable. The transducer includes an integrated subassembly of an infrared radiation source unit, an infrared radiation detector unit, and a flex connector and may be employed with an airway adapter preferably maintained by a thick film heating element at an above-dewpoint temperature to ascertain the concentration of a specie potentially present in gases flowing through the adapter. The transducer may also be employed for other purposes.

15 Claims, 29 Drawing Sheets

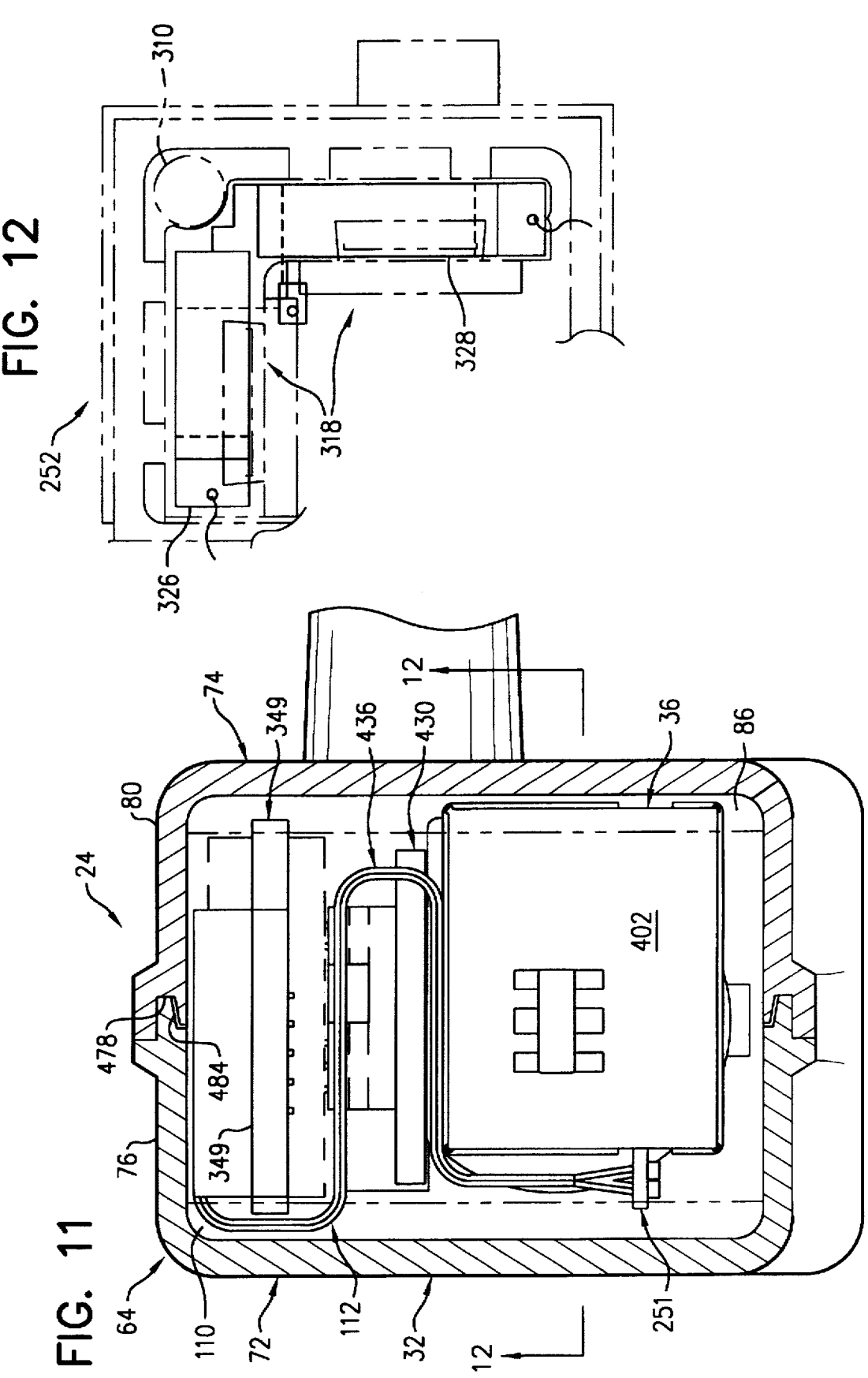

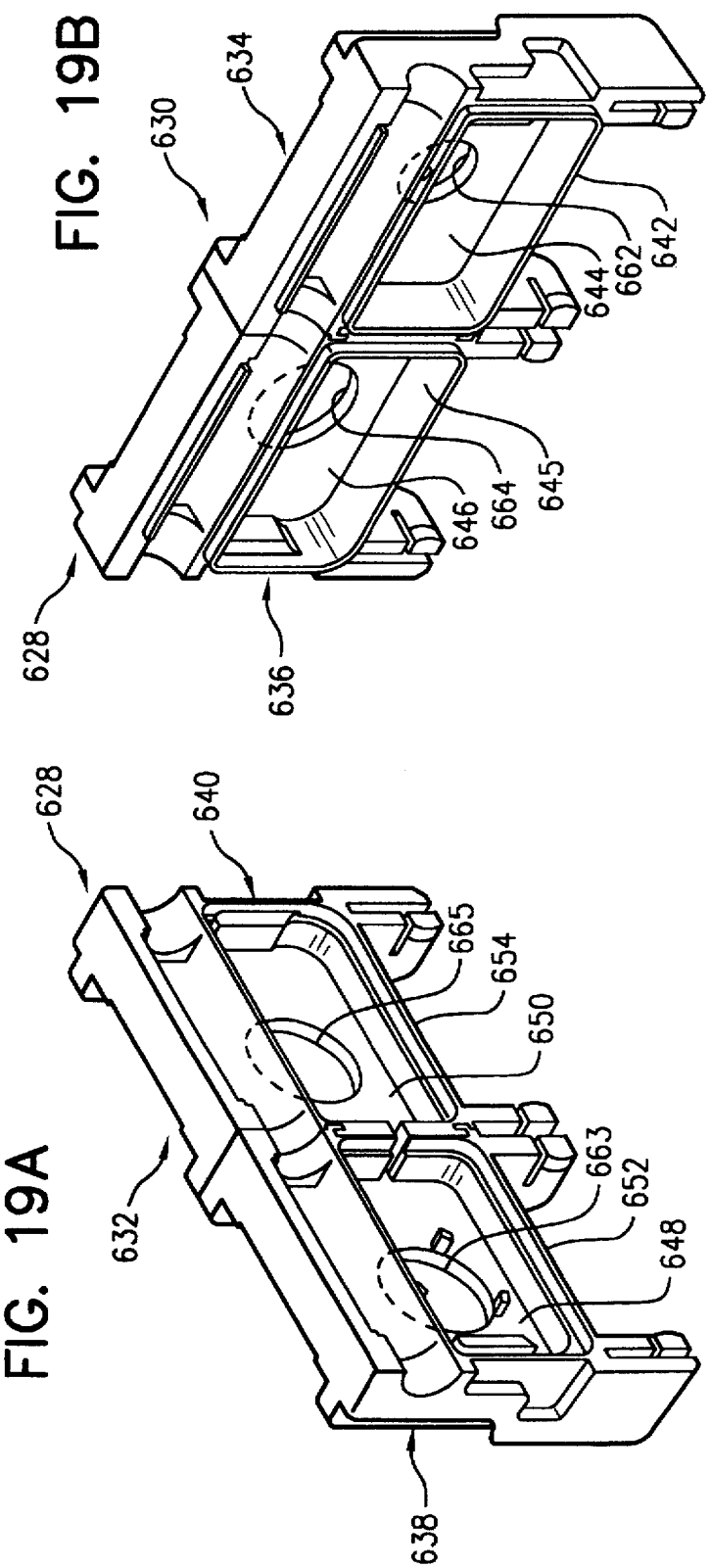

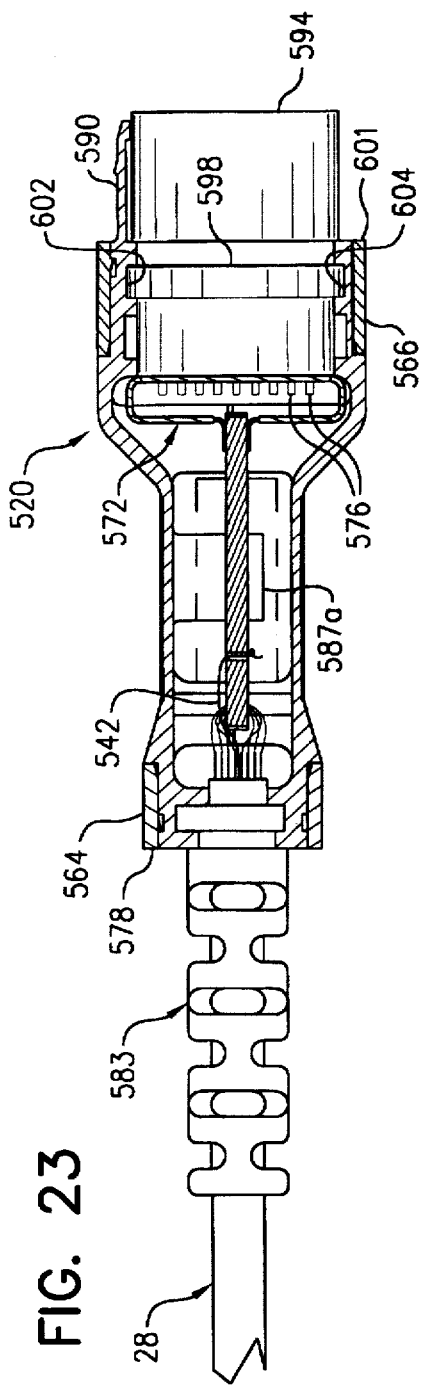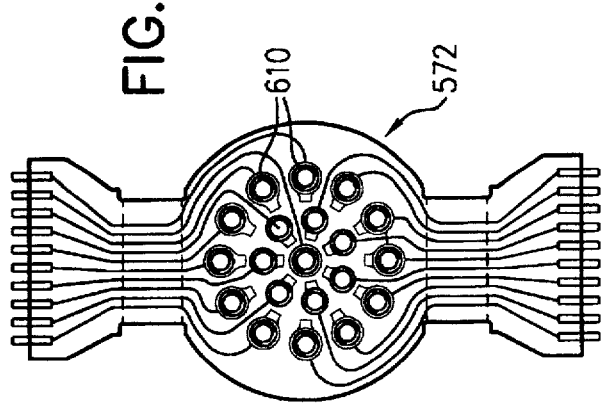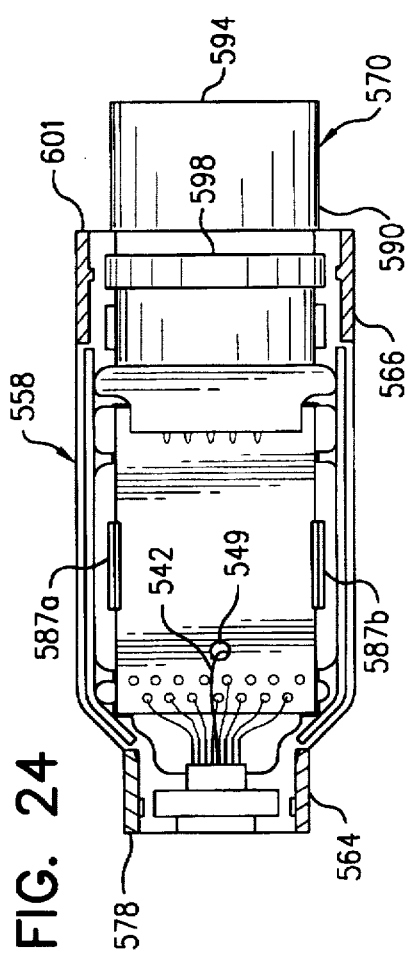
FIG. 23
FIG. 25
FIG. 24

BOTTOM SIDE OF BOARD

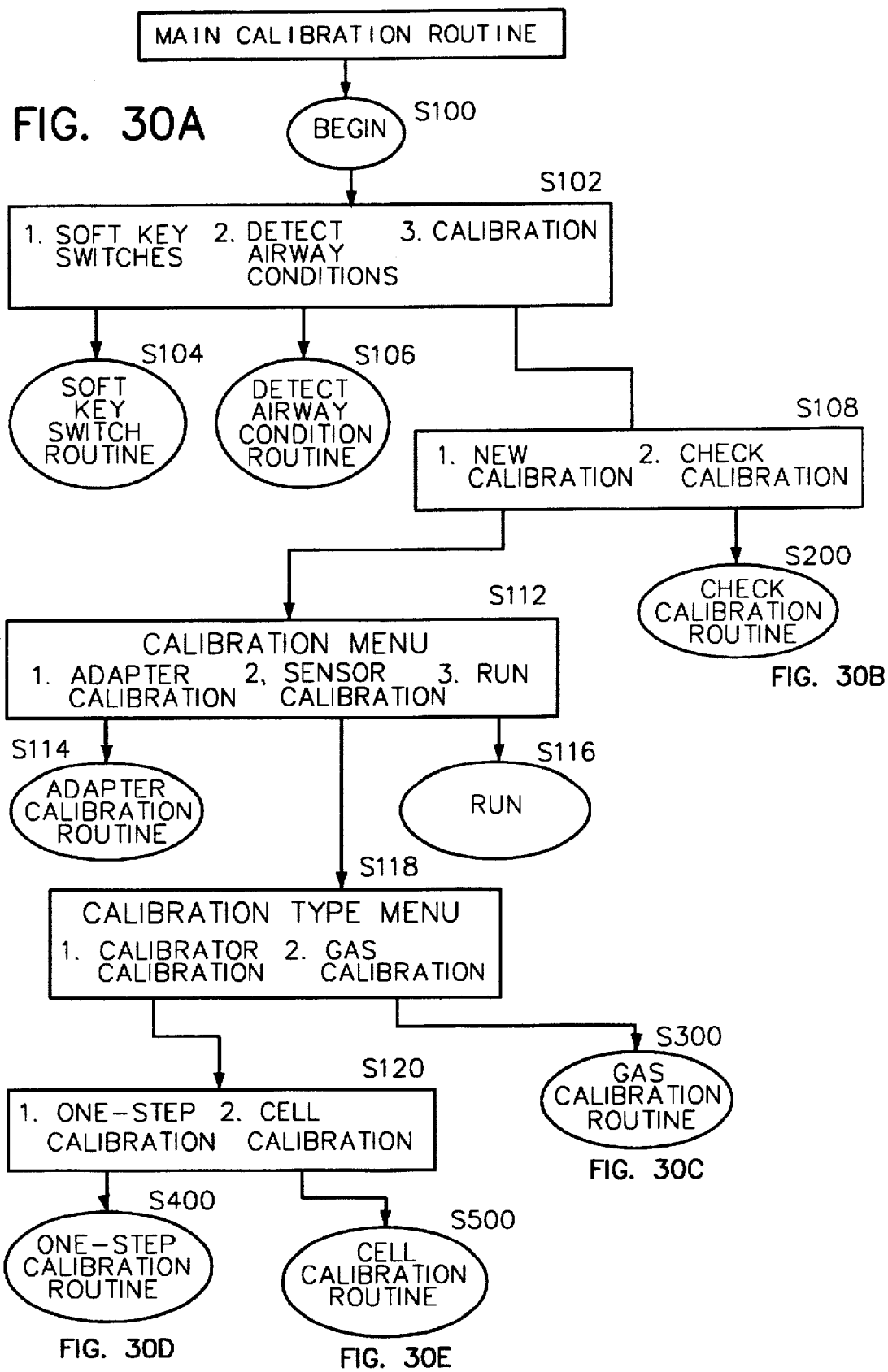

INFRARED RADIATION DETECTOR UNITS AND METHODS OF ASSEMBLING TRANSDUCERS IN WHICH SAID UNITS ARE INCORPORATED

TECHNICAL FIELD OF THE INVENTION

In one aspect, the present invention relates to novel, improved devices for emitting and detecting infrared radiation, to transducers in which those devices are incorporated, and to methods and devices for verifying the calibration of the transducers and for connecting the transducers to associated signal processing-control-display units.

In another aspect, the present invention relates to transducers of the character just described which are usable in conjunction with an airway adapter to measure the concentration of a specified gas flowing through the adapter.

In a further aspect, the present invention relates to novel, improved devices and systems which employ infrared radiation in measuring the concentration of a specified gas in a sample which may contain that gas.

BACKGROUND OF THE INVENTION

U.S. Pat. Nos. 4,859,858 and 4,859,859, both entitled GAS ANALYZERS, were issued to Knodle et al. on 22 Aug. 1989. Those patents disclose apparatus for outputting a signal indicative of the concentration of a designated gas in a sample being monitored by the apparatus.

The gas analyzers disclosed in the '858 and '859 patents are of the non-dispersive type. They operate on the premise that the concentration of a designated gas can be measured by: (1) passing a beam of infrared radiation through the gas, and (2) then ascertaining the attenuated level of the energy in a narrow band absorbable by the designated gas. This is done with a detector capable of generating an electrical output signal proportional to the concentration of the designated gas.

One important application of the approach to gas concentration measurement disclosed in the '858 and '859 patents is in capnometers for monitoring the level of carbon dioxide in the breath of a medical patient. This is typically done during a surgical procedure as an indication to the anesthesiologist of the patient's condition. As the patient's wellbeing, and even his life, is at stake, it is of paramount importance that the carbon dioxide concentration be measured with great accuracy.

In a typical instrument or system employing non-dispersive infrared radiation (NDIR) to measure gas concentration as disclosed in the '858 and '859 patents, the infrared radiation is emitted from a source and focused by a mirror on the gases being analyzed. After passing through the body of gases, the beam of infrared radiation reaches a filter. That filter reflects all of the radiation except for that in a narrow band centered on a frequency which is absorbed by the gas of concern. This narrow band of radiation is transmitted to a detector which is capable of producing an electrical output signal proportional in magnitude to the magnitude of the infrared radiation impinging upon it. Thus, the radiation in the band passed by the filter is attenuated to an extent which is proportional to the concentration of the designated gas. The strength of the signal generated by the detector is consequently inversely proportional to the concentration of the designated gas and can be inverted to provide a signal indicative of that concentration.

The actual concentration CONC in Torr of a selected gas in the optical path is determined according to the following equations:

$$IX = SCV(ZCV - MR) \tag{1}$$

$$\text{CONC Table (IX)} \tag{2}$$

In equation (1), IX is an index to locations of values in the CONC Table, SCV is a Scan Cal Value, ZCV is a Zero Cal Value, and MR is the measured ratio of the data signal to a reference signal. The index value IX is used to cross-reference the Measured Ratio MR, after it is adjusted by the Zero Cal and Span Cal Values, to the CONC Table. The values contained in the CONC Table are actual concentrations of a selected gas corresponding to different ratios of data signals to reference signals.

The Measured Ratio is the ratio of the signal through the data path $S_D$ to the signal through the reference path $S_R$ for a given gas. It is given by the following equation:

$$MR = \frac{S_{D3}}{S_{R3}} \bigg|_{C=C_m} = \frac{G_D}{G_R} = [\exp(-kl_xC_m) + L] \tag{3}$$

where $G_D$ is the gain introduced through the data path, $G_R$ is the gain through the reference path, k is the absorption (extinction) coefficient of the designated gas at a specific wavelength $1_x$ in the optical path pathlength of a reference cell containing the gas of interest, $C_m$ is the measured concentration of the selected gas, and L is the light leakage in the absorption band of the selected gas.

Zero Ratio (ZR) is the ratio of the data signal to the reference signal when the concentration of the gas being measured is zero. The Zero Ratio is given by the following equation:

$$ZR = \frac{G_D}{G_R}(1+L) \tag{4}$$

The Zero Ratio is measured by placing a zero cell in which the designated gas is absent in the optical path of a NDIR transducer and measuring the data and reference signals. While the zero ratio is being calculated, the voltages of the reference and data signals are set as close as possible to the same value using automatic gain control circuitry. The ratio of data to reference signals is thus ideally equal to unity.

For calibration verification purposes, a Span Ratio (SR) is also employed. The Span Ratio is the ratio of the data signal to the reference signal for a known concentration of selected gas CS. Substituting CS in equation (3) yields the following equation:

$$SR = \frac{S_D}{S_R} \bigg|_{C=CS} = \frac{G_D}{G_R}[\exp(-kl_xC_S) + L] \tag{5}$$

The Zero and Span Values are calculated from the Zero and Span Ratios according to the following equations:

$$ZCV = ZR \tag{6}$$

$$SVC = \frac{IX_S}{ZR - SR} \tag{7}$$

where $IX_S$ is the index value corresponding to the known concentration level $C_r$.

U.S. Pat. No. 5,369,277 issued 29 Nov. 1994 to Knodle et al. and entitled INFRARED SOURCE discloses nondispersive infrared radiation gas analyzers with infrared radiation sources which have all of the capabilities of those described in the '858 and '859 patents and are useful for the same purposes. However, the novel infrared radiation sources disclosed in the '277 patent also have a number of important advantages which the patented infrared radiation sources do not have.

Briefly, the infrared radiation sources disclosed in the '277 patent are like those disclosed in the '858 and '859 patents in that they have a low thermal conductivity substrate supporting a film-type emissive element. However, they differ in one important respect in that the ends of the substrate are not fixed at an invariable distance relative to each other. Instead, one end is fixed to a lead frame, which serves as a support for the substrate-based emitter component; and the opposite end of the substrate is left free to move relative to the lead frame. Consequently, the substrate is free to grow in length as its temperature increases; and the imposition of mechanical stresses on the emitter unit is thereby avoided.

The lead frame-based approach also facilitates assembly. For example, electrical connections are easier to make (and also less apt to break); and the need for insulated leads is eliminated. Also, the film-type emissive element is automatically centered on the axis of the energy focusing mirror. This simplifies, and reduces the cost of, the assembly process by eliminating the steps theretofore employed to insure that the emissive element was accurately aligned with the mirror.

Furthermore, the components of the infrared radiation sources disclosed in the '277 patent are primarily molded from plastics rather than being machined from metal as in the earlier patented infrared radiation sources. This allows an acceptable degree of accuracy to be maintained while significantly reducing the cost of the parts.

In addition, the novel design of the infrared radiation sources disclosed in the '277 patent allows the focusing mirror to be assembled last. This minimizes the possibility that the mirrored surface might be scratched or otherwise damaged. That is important because the mirror is the most expensive part of the infrared radiation source. Also, because the assemblies can be electrically tested without the mirror, the costs of manufacturing transducers employing the principles of the present invention are reduced.

Yet another, very important advantage of the infrared radiation sources disclosed in the '277 patent is that the thermal, physical, electrical, and other parameters of the emissive element, the electrical conductors through which current flows to the emissive element, the substrate supporting the emissive element, and even the substrate-mounting components are so balanced and correlated that the flow of heat away from the operating emissive element is closely controlled and correlated with the emitted infrared energy. This results in an infrared radiation source which can be made to emit infrared radiation of accurately predictable intensity and spectral content. This is important. For example, it is the difference in intensity between emitted and detected energy in appropriate bandwidths that is employed by NDIR gas analyzers as a measure of the concentration in a sample of the gas being monitored; and this differential is not accurate if the intensity of the emitted radiation is not consistent.

U.S. Pat. No. 5,146,092 issued 8 Sept. 1992 to Apperson et al. for GAS ANALYSIS TRANSDUCERS and U.S. Pat. No. 5,153,436 issued 6 Oct. 1992 to Apperson et al. for TEMPERATURE CONTROLLED DETECTORS FOR INFRAREDTYPE GAS ANALYZERS also disclose infrared radiation detector units which are improvements on those disclosed in the '858 and '859 patents and which, when employed in the NDIR measurement of a designated gas, make it possible to do this more accurately than is believed to have theretofore been possible by way of that approach. This is a significant advantage, especially in medical and other applications where a high degree of accuracy is of the utmost importance. At the same time, and unlike dispersive-type analyzers, these novel detector units and systems employing them are compact and rugged enough for the most demanding applications and are relatively inexpensive to produce.

Increased accuracy is achieved, in accord with the principles of the inventions disclosed in the just-cited '092, '346, and '277 patents, by a novel beam splitter which divides the energy over the entire compass of a beam passed through gases being analyzed into moieties in which the energy is of wavelengths that are respectively shorter and longer than a designated wavelength. The energy in these moieties is transmitted through appropriate bandpass filters to data and reference detectors of like dimensions which are positioned in mirror image relationship to the beam splitter. Consequently, both detectors receive energy of appropriate wavelengths from all parts of the beam. This eliminates the inaccuracies which occur in side-by-side and other detector systems in which the image of the beam falling on the detectors is different in space because the data and reference detectors are not spatially coincident.

A novel, monolithic, isothermal mount supports the beam splitter and the reference and data detectors with the precision required for optimal accuracy. Light traps associated with the mount keep extraneous energy from reaching the detectors, providing a further increase in accuracy.

Associated with the system for maintaining the data and reference detectors at the wanted temperature is an onboard power supply. The power supply output voltage is used to bias the detectors; and, because the output is precisely regulated, this is done essentially without the inaccuracies in the outputs from the data and reference detectors that would occur if the biasing voltage fluctuated.

Lead selenide detectors are preferred because of their sensitivity and consequent capability for accurately reflecting the magnitude of the infrared radiation falling on them. However, this means that they are very sensitive to variations in substrate temperature. Therefore, even minor fluctuations in the detector temperature and minor differences between the temperatures of the data and reference detectors can markedly affect accuracy. A sensor/heater system promotes accuracy by heating the isothermal support in a manner that keeps the two detectors precisely at a selected temperature, typically with a variation $\leq 0.01°$ C. The support is fabricated from a heat conductive material and so configured as to reduce the temperature difference between the data and reference detectors to this very small value.

At the same time, the novel, monolithic detector supports and other features of the devices disclosed in the '092, '346, and '277 patents make them rugged, but still compact.

Also incorporated in the detector units of the devices disclosed in the three patents just referred to are a pair of electronic amplifiers. These increase the outputs from the data and reference detectors to levels at which they can be transmitted without excessive noise to a signal processor. The signal processor converts the detector outputs to a ratioed signal reflecting the concentration of the selected gas in the stream or other sample being analyzed.

Typically, detector units of the character disclosed in the above-cited patents are employed in environments in which electrical noise is prevalent. A novel electrostatic shield effectively isolates the data and reference detectors and associated circuitry from the adverse effects of EMI and other radiations in the ambient surroundings.

A novel casing houses the electrostatic shield and the detectors and other electrical and optical components of the detector unit and keeps foreign matter from reaching those components. Guide systems in the casing and in the electrostatic shield facilitate the assembly of the unit and the electrical connection of the electrostatic shield to the components shielded by that device.

The casing in which the detector unit is housed may be one component of a transducer which also includes a source as described above with components for: emitting electromagnetic energy, focusing that energy into a beam, and propagating the beam through the gases being analyzed. In applications of the invention which are of particular interest, these transducers are used with an airway adapter to measure the concentration of a gas such as carbon dioxide flowing through the adapter.

These airway adapters may be of the character disclosed in copending applications Ser. Nos. 08/300,146 and 08/300,383 filed 2 Sept. 1994 and therefore potentially disposable after a single use or of another construction with that advantage; and optical characteristics may vary from one adapter to the next. This, however, is inconsequential, and interchangeability is provided, when a detector unit of the character disclosed in the '092 and '346 patents is employed in the transducer. Because both the data and reference detectors of such units react to the energy over the same compass of the attenuated beam, optical variations—and other sources of error including drift, foreign substances in the optical path, etc.—affect both detectors in the same manner and to the same extent. Therefore, anomalies are canceled out when the data and reference detector output signals are ratioed. This also means that the frequent recalibration required in other non-dispersive, dual detector systems is unnecessary or, at worst, minimized.

Preferably, a second system independent of that utilized to control detector temperatures is employed to keep the casing of the airway adapter at an elevated temperature (preferably in the 42°–45° C. range). This is high enough to keep moisture from condensing on those windows incorporated in the airway adapter to pass the radiant energy into that device and, after it has passed through the gas being analyzed, to the detector system. This approach to eliminating the problems that condensation might cause has the important advantage that heating the airway adapter has no effect on the power supplied to the data and reference detector heaters. Consequently, the fluctuations in the detector heater power supply that would occur as the casing heats up if the casing heater and detector heater circuits were tied together are eliminated. So are the unwanted changes in detector temperature that would be caused by such fluctuations.

U.S. Pat. No. 5,206,511 issued 27 Apr. 1993 to Apperson et al. and entitled CALIBRATORS FOR INFRARED-TYPE GAS ANALYZERS discloses certain new and novel devices which, in contrast to those theretofore proposed, make the verification of infrared radiation transducer calibration simple, time-efficient, and accurate.

In the verification technique disclosed in the '511 patent, a Concentration Factor ($CF_s$) is predetermined for a specific transducer analyzer. The Concentration Factor is independent of the gain of the system, requiring only a specific concentration of the gas of interest in a reference cell which can be associated with the transducer being checked. The Concentration Factor can be defined as the ratio of the absorption at a given designated gas concentration to the absorption at zero concentration of the designated gas. The Concentration Factor for a specific transducer is stored in non-volatile memory.

The transducer calibration is verified in a novel one-step process by obtaining a Zero Ratio, retrieving the Concentration Factor from the nonvolatile memory, and calculating Zero and Span Cal Values from the Zero Ratio and the Concentration Factor. The need to measure both Zero and Span Ratios is eliminated.

Since the gains of the data and reference channels or detectors are set to approximately the same value by the automatic gain control circuitry, the Span and Measured Ratios are derivable from the Zero Ratio and the Concentration Factor. The following equations define the Measured and Span Ratios in terms of the Concentration Factor and the Zero Ratio:

$$MR = ZR(CF_m) = \frac{[G_D(1+L)] \, [\exp(-kl_x C_m) + L]}{[G_R][1+L]} \quad (8)$$

$$SR = ZR(CF_s) = \frac{[G_D(1+L)] \, [\exp(-kl_{sc} C_s) + L]}{[G_R][1+L]} \quad (9)$$

The closer the automatic gain control sets the gain of the data and reference channels to equal, the closer the Span and Measured Ratios are to the absorption term. Accordingly, a linear relationship exists between the Measured Ratio and the absorption term. However, the relationship between the Measured Ratio and the sample gas concentration C is exponential.

In the foregoing equations, k is constant for a given sample gas, $1_{sc}$ is constant for all airway adapters and the calibrator being used, and L is fixed by the amount of light passing through the filter. Therefore, the Concentration Factor $C_s$ for a given concentration level CS is constant. Consequently, once the gains in the system are set for a zero percentage concentration of the designated gas, the known Concentration Factor for a selected gas may be used to calculate the Span Cal Value.

The Concentration Factor may be stored in non-volatile memory in two ways. First, the Concentration Factor may be calculated in the factory from equation (9) for a given Zero Ratio and Span Ratio. During subsequent factory or field verification of a specific transducer calibration, a New Zero Ratio (NZR) is measured; and a New Span Ratio (NSR) for the transducer calibration is calculated according to the follow equation:

$$NSR = NZR(CF_s) \quad (10)$$

The second method of carrying the Concentration Factor in memory is to store Zero and Span Ratios calculated at the factory and calculate a New Zero Ratio and New Span Ratio therefrom for a specific transducer calibration according to the following equation:

$$NSR = NZR * \frac{SR}{ZR} \quad (11)$$

The new Zero and Span Ratios are then substituted for the Zero and Span ratio terms in equations (6) and (7) to solve for the Zero and Span Cal Values.

The novel method of verifying infrared radiation transducer calibrations disclosed in the '511 patent is superior to the prior gas flow and gas cell methods because:

(a) The Span Ratio can be readily calculated for a specific transducer from a Concentration Factor determined under carefully controlled factory calibration procedures;

(b) two measurement points are not needed;

(c) gas storage tanks need not be kept on hand; and (d) the expense and uncertainty of sealing a known concentration of the gas of interest in a span cell is avoided.

The patented invention may be configured to allow use of the theretofore employed gas flow and gas cell calibration methods in addition to the one-step and two-step calibration methods disclosed in the '511 patent. Thus, any appropriate method of calibration may be chosen, and maximum flexibility in calibrating infrared radiation transducers for NDIR gas analyzers and other apparatus is maintained.

SUMMARY OF THE INVENTION

There have now been invented, and disclosed herein, certain new and novel transducers, infrared radiation detectors and emitters, and calibration verification devices and techniques which: (a) have the advantages of those discussed above and (b) are nevertheless superior in important respects.

The transducers disclosed herein are smaller, lighter, and less expensive to build. The reduction in manufacturing cost is important for obvious reasons. The decrease in size and reduction in weight are particularly important in applications in which the transducer is employed with an airway adapter in close proximity to a patient's face at the distal end of an endotracheal tube or a nasal cannula to monitor a patient's breathing. This reduction in size and weight becomes particularly important when the patient is a neonate or infant or even a small child.

The novel calibration verifiers disclosed herein have the significant advantage that they are passive devices. That is, they have no electrical connections to the system components they are employed to check, unlike the corresponding devices disclosed in the '511 patent. Those patented devices are mechanically and electrically attached to one end of a multilead cable which is employed to connect the transducer to an associated signal-processing-control-display unit (SPCDU), which can make the coupling of the calibration verification device to the transducer awkward.

The substitution of a passive transducer calibration verification device for the verification device disclosed in the above-cited '511 patent makes a significant contribution to simplicity, weight reduction, and lower cost of manufacture as well as making the calibration verifier easier to use because the passive verifier can be slidably mounted on the transducer-to-SPCDU cable and, consequently, easily coupled to the transducer being checked.

A related, also important feature of the present invention is the incorporation of a programmable, solid state memory such as an EEPROM in the connector unit or plug of an integrated cabling system by which the transducer is connected to the associated SPCDU. Stored in this memory are parameters peculiar to each transducer and parameters for the calibration verification device. This information can accordingly be readily retrieved on an "as needed" basis by the SPCDU in the course of verifying the calibration of the transducer.

An important feature of the transducer which contributes to the objectives of smaller size, lower weight, and reduced cost is a construction which eliminates one of the radiant energy transmitting windows required in those transducers disclosed in the '858, '092, and other patents cited above.

The novel transducers disclosed herein also feature an integrated subassembly (ISA) which includes an infrared radiation emitter unit, an infrared radiation detector unit, a printed circuit board (PCB) with the circuits employed in the operation of the transducer, and a flexible circuit device which mechanically and electrically connects up the emitter and detector units and the PCB. This assembly allows the performance of a transducer's active components to be tested as a unit rather than individually before the transducer is assembled. As a consequence, it is not necessary to wait until a transducer is assembled to determine whether it will meet performance specifications. The result can be a significant cost savings, an objective which is furthered by the elimination of hard wiring and a significant reduction in the expense of assembly. Ease of assembly with a consequent reduction in assembly cost is also promoted by a novel transducer casing construction which facilitates the optical alignment of the emitter unit and the detector unit and allows the components of the housing to be joined by an adhesive bond.

Also featured in the transducers disclosed herein are novel, improved infrared radiation source and detector units which feature simplified construction and assembly, increased reliability, lower power requirements, a reduction in shielding requirements, and an increased signal-to-noise ratio. Another important feature of the invention is the multipin input connector on the cable by which the transducer is connected to the SPCDU with which the transducer is employed. This connector is simple and easily assembled. Together with the transducer and a cable featuring a load-absorbing member, the connector keeps potentially damaging loads and strains from being imposed on the electrical leads in the cable, allowing less expensive leads to be employed.

Also, the transducers disclosed herein are designed to be more rugged than those disclosed in the cited patents and to have an optimized focal length which makes it possible to employ a smaller, less expensive, infrared radiation transmitting window in the detector unit of the transducer. Further, this and the other windows in the transducer have a simple, flat edge configuration which makes them less expensive than the stepped edge windows of the patented transducers discussed above.

Still another and obviously important advantage of the invention is backwards compatibility with the SPCDU's disclosed in the patents cited above.

Other important objects, advantages, and features of the invention will be apparent to the reader from the foregoing and the appended claims and as the ensuing detailed description and discussion proceeds in conjunction with the accompanying drawings.

INCORPORATION BY REFERENCE

The following United States patents discussed above are hereby incorporated in this application by reference:

| Patent Number | Title | Issue Date |
|---|---|---|
| 4,859,858 | GAS ANALYZERS | 22 Aug. 1989 |
| 4,859,859 | GAS ANALYZERS | 22 Aug. 1989 |
| 5,146,092 | GAS ANALYSIS TRANSDUCERS WITH ELECTROMAGNETIC ENERGY DETECTOR UNIT | 08 Sep. 1992 |
| 5,153,436 | TEMPERATURE CONTROLLED DETECTORS FOR INFRARED-TYPE GAS ANALYZERS | 06 Oct. 1992 |
| 5,206,511 | CALIBRATORS FOR INFRARED-TYPE GAS ANALYZERS | 27 Apr. 1993 |
| 5,369,277 | INFRARED SOURCE | 29 Nov. 1994 |

BRIEF DESCRIPTION OF THE DRAWING

FIG. 11 is a section through the detector unit end of the transducer casing showing the relationships among the detector unit, a PCB with a power supply and controls for a detector heater, and a flexible connector utilized to electrically couple the detector unit to the PCB;

FIG. 12 is a section taken essentially along line 12—12 of FIG. 11 to show the components of the detector heater;

FIGS. 19A and 19B are internal views of the two components which make up the casing of the calibration verification unit;

FIG. 23 is a section through the FIG. 22 plug;

FIG. 24 is a section through the FIG. 22 plug taken to better show a printed circuit board component of the plug;

FIG. 25 is a plan view of a multilead flex connector which is a component of the FIG. 22 plug;

FIG. 30A is a flow chart of the MAIN CALIBRATION ROUTINE of a transducer calibration verification protocol embodying the principles of the present invention;

DETAILED DESCRIPTION OF THE INVENTION

Figure 1:
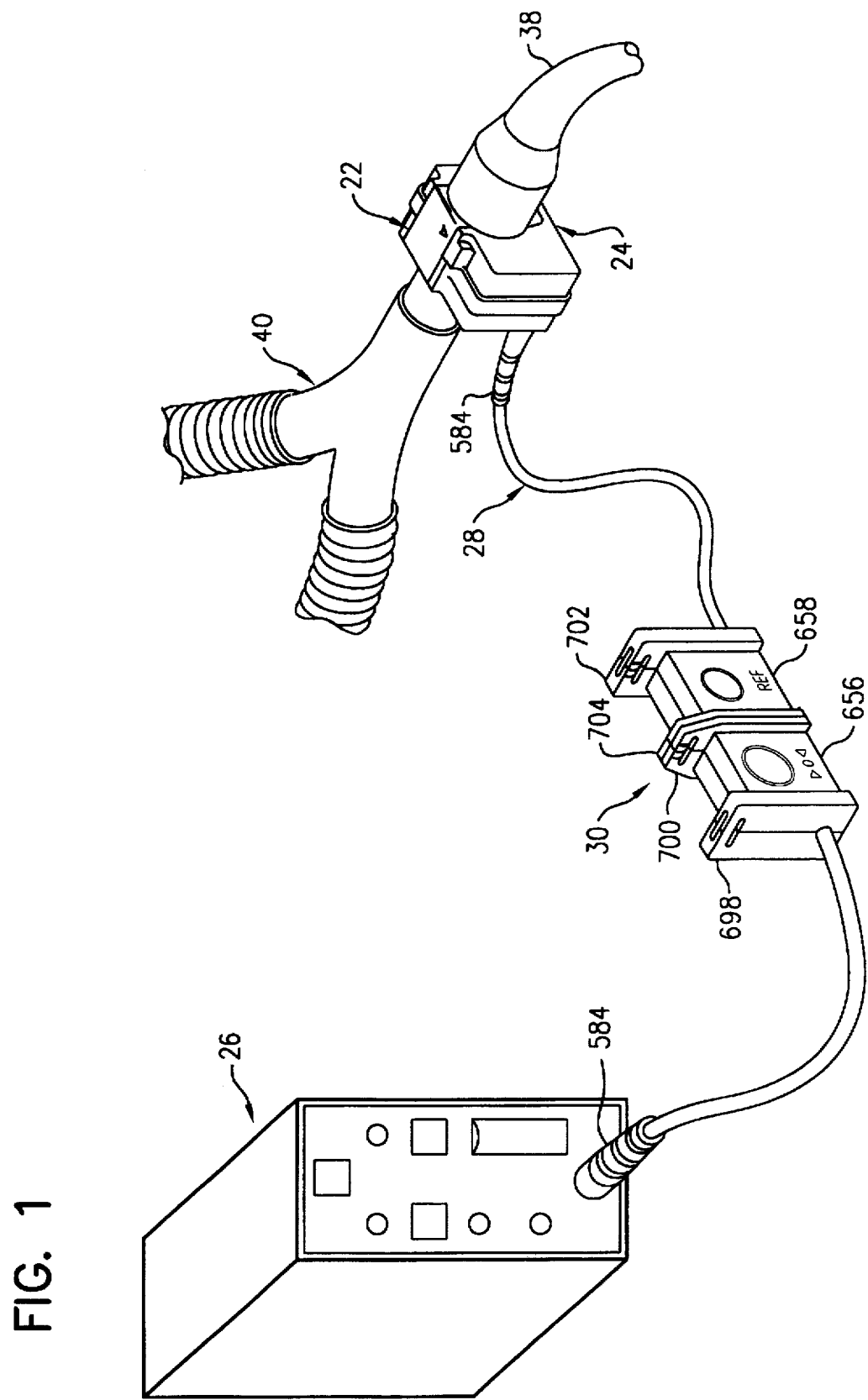
FIG. 1 is a pictorial view of a gas analyzer system which has: (a) a transducer employing the principles of the present invention and designed to measure the concentration of carbon dioxide in the gases flowing through an airway adapter connected between an endotracheal tube or nasal cannula and the plumbing of a mechanical ventilator; (b) an active cable system also employing the principles of the present invention for coupling the transducer to a monitor (SPCDU) which has signal processing, display, and control capabilities; and (c) a cable-mounted passive unit designed in accord with the principles of the present invention and employed to verify the calibration of the carbon dioxide concentration-measuring transducer.
Figure 2:
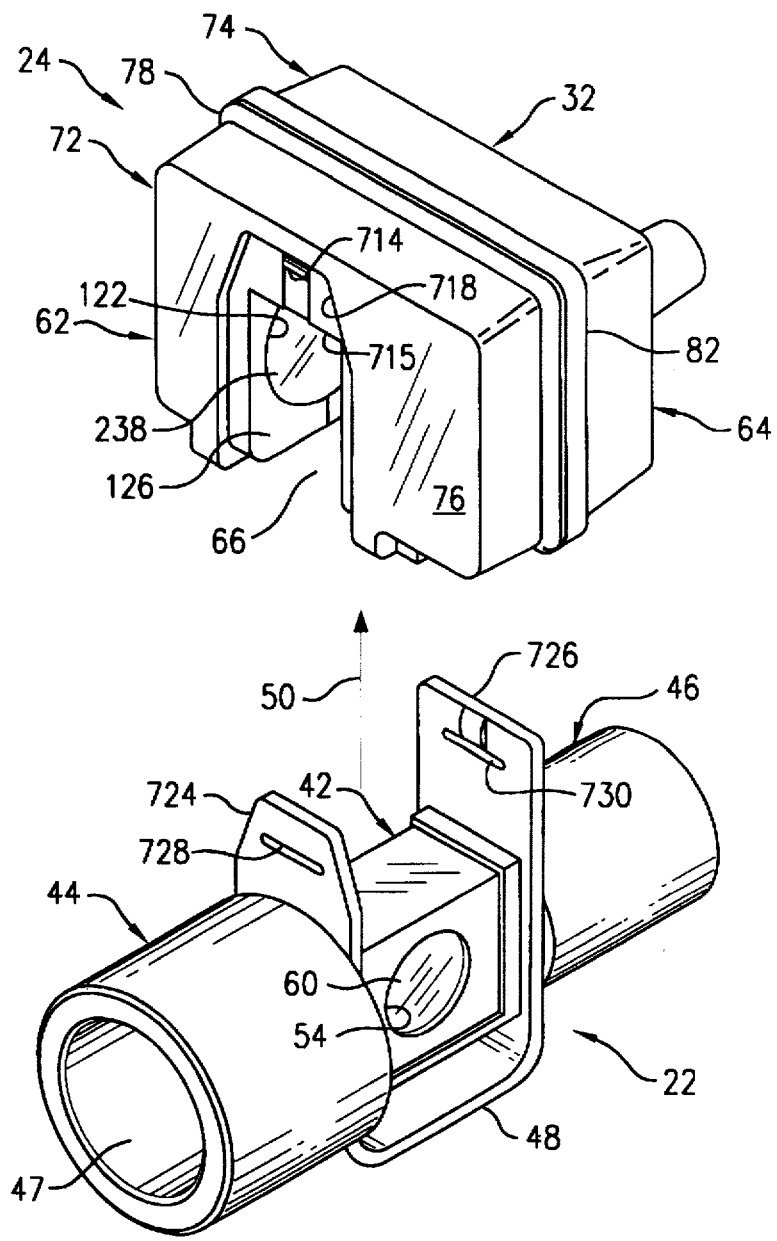
FIG. 2 is an expanded view of the FIG. 1 transducer and airway adapter.
Figure 3:
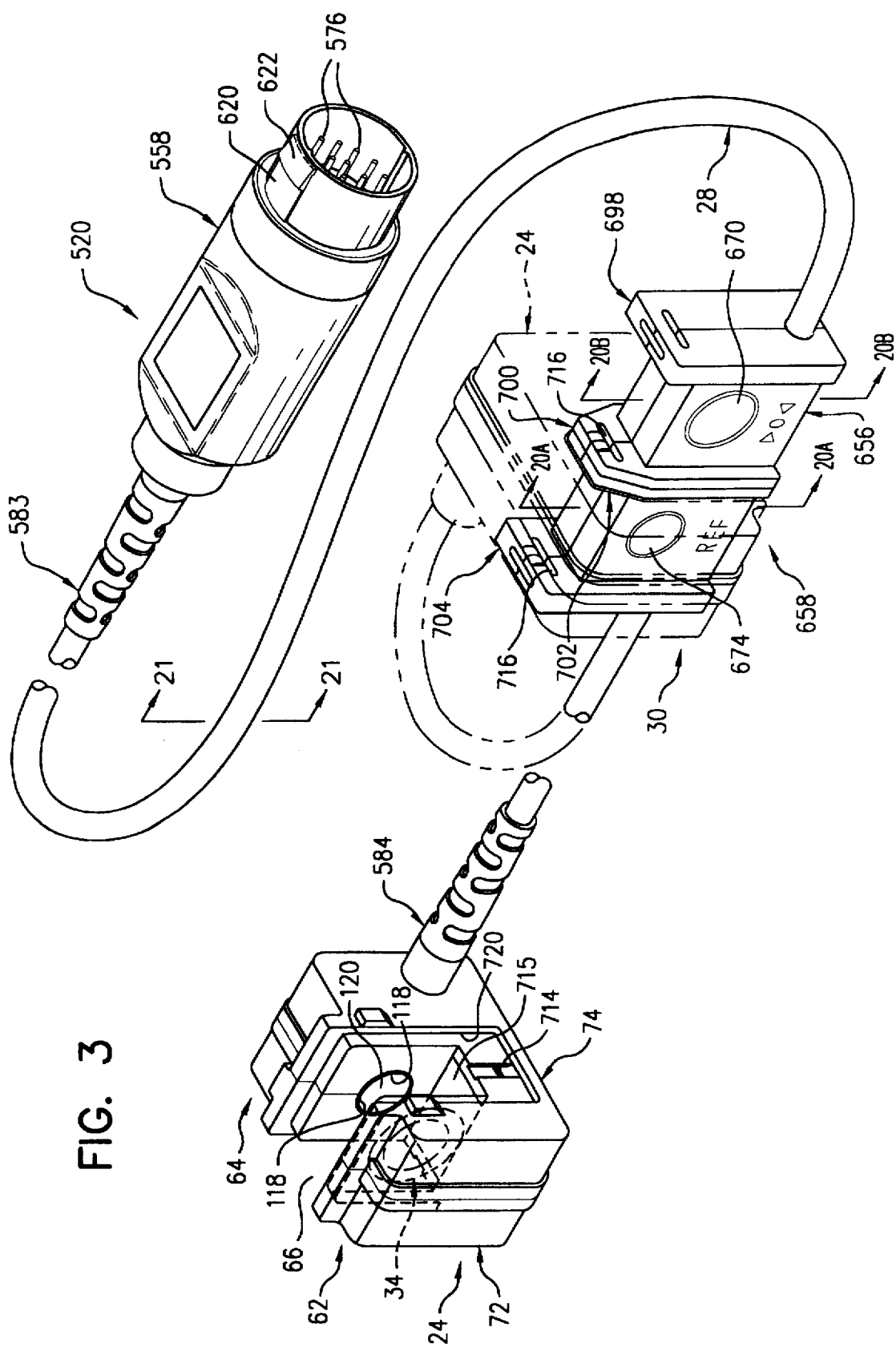
FIG. 3 is a generally pictorial view of an integrated assembly employing the principles of the present invention and made up of the FIG. 1 transducer, the active cable or connector system, and the cable mounted calibration verifier.

The principles of the present invention can be employed to particular advantage in transducers for outputting: (a) a signal proportional in magnitude to the concentration of carbon dioxide flowing through an airway adapter in a patient-to-mechanical ventilator circuit, and (b) a reference signal. These signals can be ratioed in the manner disclosed in the above incorporated U.S. patents to provide a third signal accurately and dynamically representing the concentration of the carbon dioxide flowing through the airway adapter. A representative airway adapter and a complementary transducer constructed in accord with, and embodying, the principles of the present invention are shown in FIGS. 1, 2, and 3 and respectively identified by reference characters 22 and 24. Also shown in FIG. 1 is a unit 26 which: (1) powers and controls the operation of transducer 24; and (2) extracts from signals outputted by the transducer, and displays, information such as: (a) the concentration of carbon dioxide in a patient's exhalations, (b) inspired carbon dioxide, (c) respiration rate, and (d) end tidal carbon dioxide. This unit is referred to above and hereinafter as a SPCDU and as a monitor.

FIGS. 1 and 3 also depict in some detail a novel cable 28 employed to electrically connect transducer 24 to SPCDU 26. Additionally depicted in FIG. 1 is an equally unique passive (non-electrical) unit 30 which is mounted on and slidable along cable 28 and is employed to rezero transducer 24 and to verify the factory calibration of the transducer, thereby ensuring that the transducer is operating correctly.

FIG. 2 shows primarily the polymeric housing 32 of transducer 24. This transducer also includes: (a) an infrared radiation source unit 34 (FIGS. 4, 4A, 5, 7–9, 13–15, 15A, and 15B), and (b) an infrared radiation detector unit 36 (FIGS. 4, 4A, 5, and 7–12).

The illustrated airway adapter 22 (FIG. 1) is designed for connection between an endotracheal tube 38 inserted in a patient's trachea and the plumbing 40 of a mechanical ventilator (not shown). Transducer 24 is in this instance employed to measure the expired or end tidal carbon dioxide level of a medical patient.

The particular airway adapter 22 illustrated in FIGS. 1 and 2 is not, by itself, part of the present invention. Consequently, it will be described herein only to the extent necessary for an understanding of the present invention.

Figure 9:
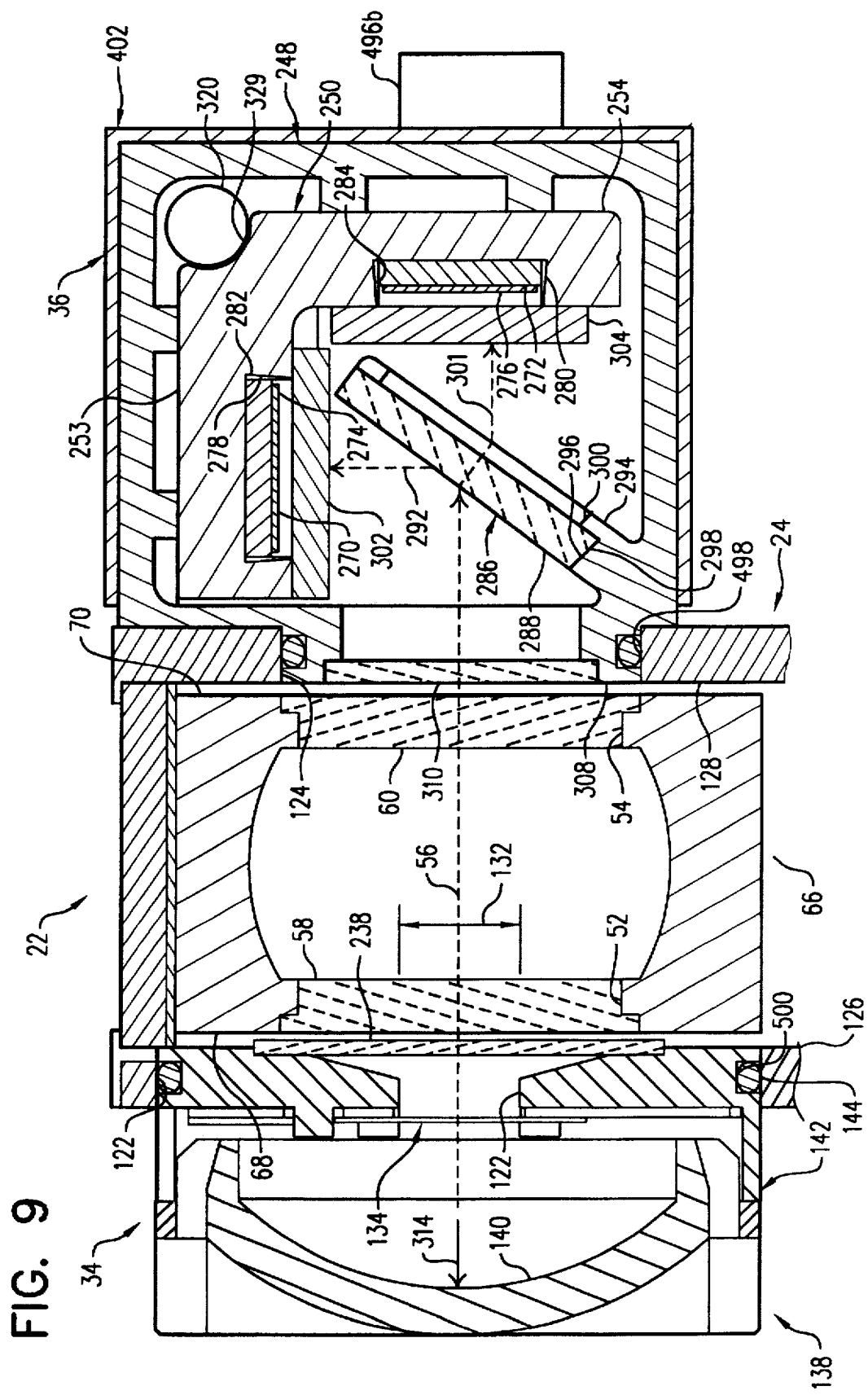
FIG. 9 is a section through the assembled FIG. 1 transducer and airway adapter showing: (a) the physical relationships among certain major components of the transducer and the airway adapter; and (b) the generation, propagation, interception, and detection of a beam of infrared radiation employed in accord with the principles of the present invention in measuring the concentration of a selected molecular species in gases flowing through the airway adapter.

Referring then to FIGS. 2 and 9, airway adapter 22 is typically molded from Ultem (a poly-carbonate manufactured by General Electric Company) or a comparable polymer. Airway adapter 22 has a generally parallelepipedal center section 42 and two cylindrical end sections 44 and 46 with a sampling passage 47 extending from end-to-end through the adapter. End sections 44 and 46 are axially aligned with center section 42.

The central section 42 of airway adapter 22 provides a seat for transducer 24. An integral, U-shaped casing element 48 positively locates transducer 24 endwise of the adapter and, also, in that transverse direction indicated by arrow 50 in FIG. 2. Arrow 50 also shows the direction in which airway adapter 22 is displaced to assemble it to transducer 24.

Apertures 52 and 54 are formed in the center section 42 of airway adapter 22. With transducer 24 assembled to the airway adapter, these apertures are aligned along an optical path identified by reference character 56 in FIG. 9. That optical path extends from the infrared radiation source unit 34 in transducer 24 transversely across airway adapter 22 and the gas(es) flowing therethrough to the infrared radiation detector unit 36 of transducer 24.

To: (a) keep the gases flowing through airway adapter 22 from escaping through apertures 52 and 54 without unacceptably attenuating the infrared radiation traversing optical path 56, and (b) keep foreign material from the interior of the airway adapter, the apertures are sealed by sapphire or other infrared radiation transmitting windows 58 and 60.

That casing or housing 32 of transducer 24 in which the infrared radiation source unit 34 and detector unit 36 are housed has first and second end sections 62 and 64 with a rectangularly configured gap 66 therebetween (see FIG. 2). With transducer 24 assembled to airway adapter 22, the two end sections 62 and 64 of transducer casing 32 embrace those side walls 68 and 70 of airway adapter central section 42 in which energy transmitting windows 58 and 60 are installed (see FIG. 9).

Referring now to FIGS. 4, 4A, 5, 9, and 11–13, transducer casing 32 is composed of two mating, complementary, cuplike casing components 72 and 74, which may be molded from a polycarbonate or any other appropriate polymer. Each of the casing components 72 and 74 has a flat side wall and an integral rim oriented at right angles to the side wall. The side wall and rim of component 72 are identified by reference characters 76 and 78, and the side wall and rim of casing component 74 are designated 80 and 82. Defined in large part by the side walls and rims of casing components 72 and 74 are two pairs of complementary cavities which cooperate to define an infrared radiation source compartment 84 in transducer housing end section 62 and an infrared radiation detector compartment 86 in transducer housing end section 64. The cavities in housing components 72 and 74 which define compartment 84 are respectively identified by reference characters 87 and 88; the cavities in those casing components which define compartment 86 are respectively identified by reference characters 90 and 92.

The apposite, inner ends of infrared radiation source and detector compartments 84 and 86 are bounded by complementary, integral wall segments of casing components 72 and 74. The integral wall segments defining the inner end of compartment 84 in casing components 72 and 74 are respectively identified by reference characters 94 and 96. Those integral wall segments of the casing components defining or bounding the inner end of detector compartment 86 are respectively identified by reference characters 98 and 100. As will be appreciated from FIG. 2, integral transducer casing wall components 94 . . . 100 also bound and define the gap 66 which receives airway adapter 22.

Figure 4:
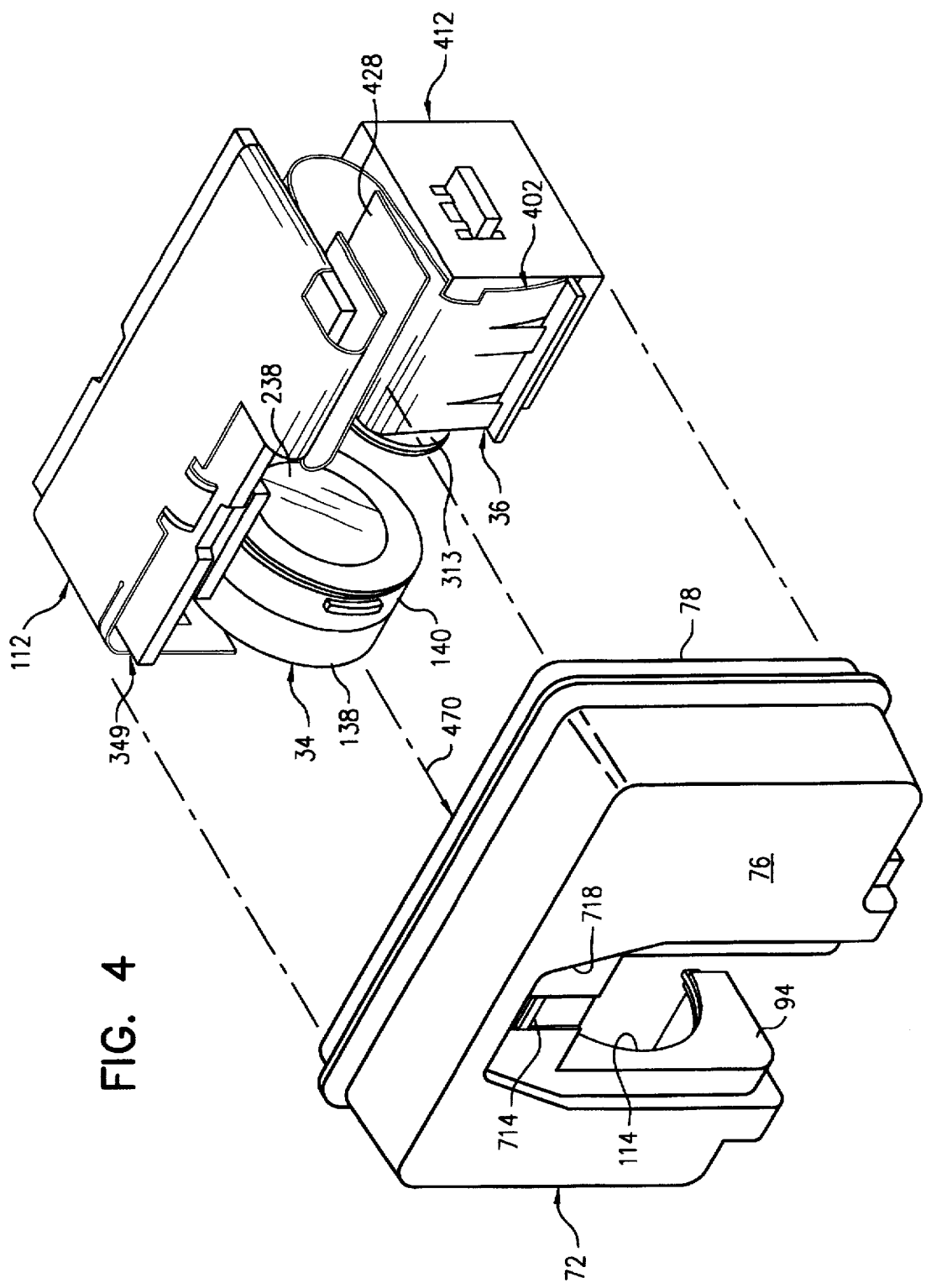
FIG. 4 is an exploded view showing how an integrated assembly of the FIG. 3 transducer components (ISA), which is fabricated in accord with the principles of the invention, fits into and is installed in one of two complementary transducer casing components.
Figure 4A:
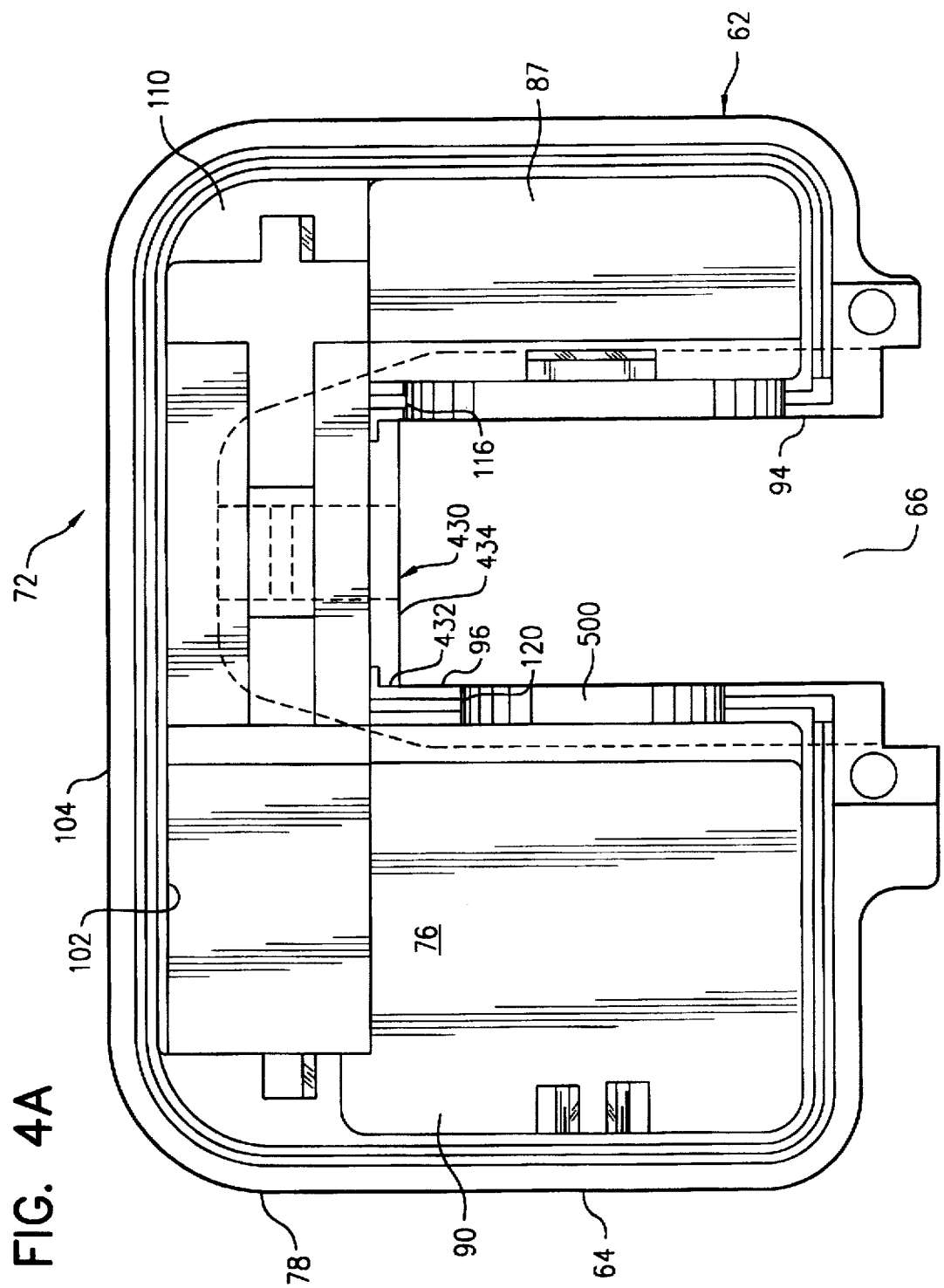
FIG. 4A is a plan view of the FIG. 4 casing component with the ISA installed.

There is a gap 102 between those ends of the wall segments 94 and 98 of transducer casing component 72 and the segment 104 of the casing component rim 78 threadadjacent (see FIG. 4A). And there is a complementary gap 106 between the free ends of the integral wall segments 96 and 100 of transducer casing component 74 and the rim segment 108 of casing component 74 (see FIGS. 5 and 8).

Figure 13:
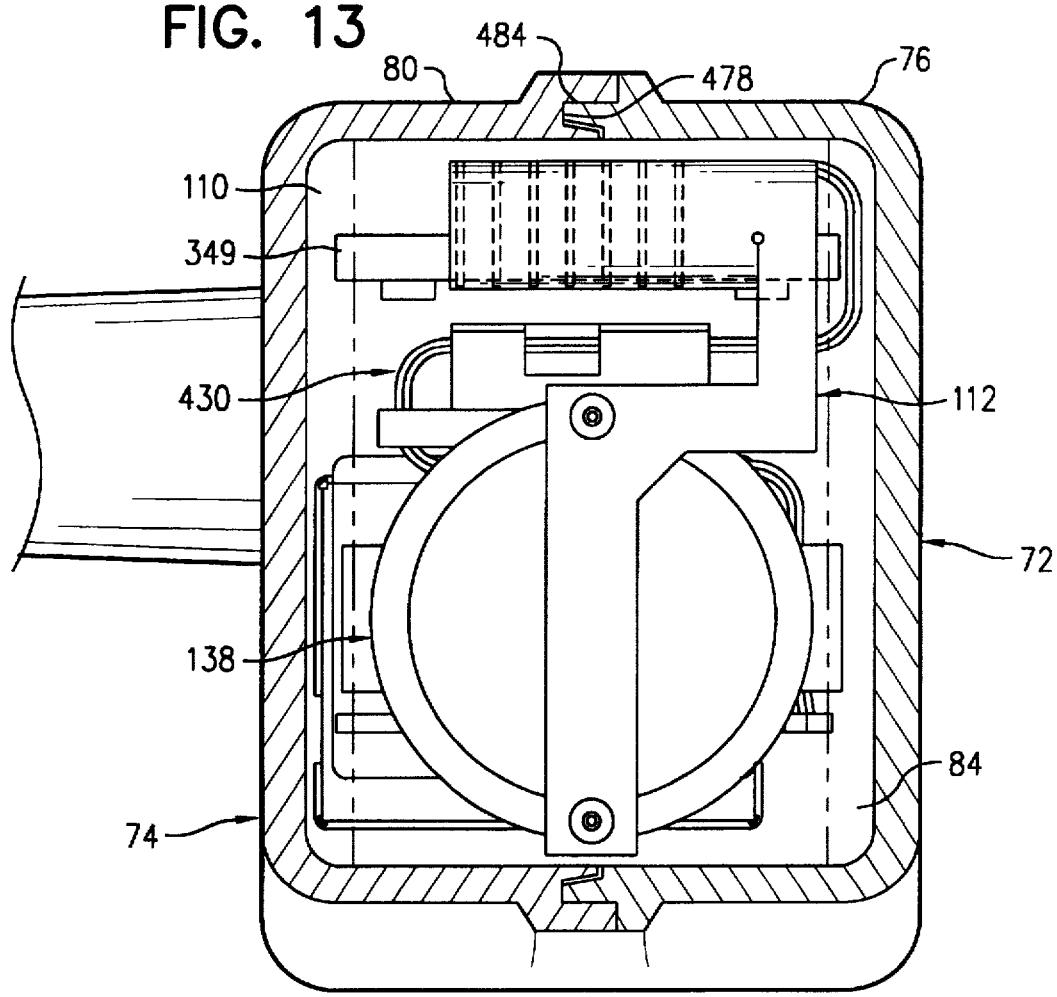
FIG. 13 is a section through the infrared radiation source end of the transducer showing the infrared radiation source unit, the PCB with the power supply for the source unit, and a flexible connector which mechanically and electrically couples the infrared radiation source unit to the printed circuit board.

Complementary gaps 102 and 106 cooperate to define a passage 110 extending between the infrared radiation source and infrared radiation detector compartments 84 and 86 in transducer casing 32 (see FIGS. 4A, 11, and 13). As will be discussed hereinafter, passage 110 accommodates a folded, space saving, multilead flex connector 112 which provides the requisite electrical connections between infrared radiation source unit 34 and infrared radiation detector unit 36 and circuits which power and control those units. Flex connector 112 also significantly reduces the time required to manufacture transducer 24.

Two sets of complementary half-moon gaps or openings are formed in the inner wall segments 94 . . . 100 of transducer casing components 72 and 74 with the opening 114 in segment 94 of component 72 mirroring the opening 116 in the wall segment 96 of casing component 74 and the opening 118 in the wall segment 98 of component 72 (FIG. 3) mirroring the opening 120 in the wall segment 100 of casing component 74. The cooperating half-moon openings 114 . . . 120 provide circular apertures 122 and 124 in the inner transducer casing walls 126 and 128 bounding gap 66 for infrared radiation propagated from infrared radiation source unit 34 through airway adapter 22 to infrared radiation detector unit 36. The apertures 122 and 124 in transducer casing 32 are sealed by windows fabricated of sapphire or other infrared radiation transmitting material to isolate transducer casing compartments 84 and 86 and keep carbon dioxide and other foreign material which might effect the accuracy of, or otherwise interfere with, the transducer from reaching the infrared radiation source and detector units 34 and 36 housed in those compartments. Those windows are components of infrared radiation source unit 34 and infrared radiation detector unit 36 and are described below in discussions of those units.

Referring now to FIGS. 8, 9, 13, and 14, the unit 34 employed to emit infrared radiation, to form that energy into a beam 132 (see FIG. 9), and to propagate the beam along optical path 56 includes: an infrared radiation emitter 134, a lead frame 136, a tubular cap 138 with a mirror 140, a base 142, and an O-ring 144 (FIG. 9).

Infrared radiation emitter or energy source 134 (FIGS. 15 and 15A) has a unique thick film construction. It includes a substrate 145 which is formed from a material having low thermal conductivity. Steatite (a polycrystalline material containing magnesium oxide and silicon dioxide) is preferred because it has a thermal conductivity which is on the order of one magnitude less than conventional low thermal conductivity materials such as alumina. This is important because it significantly reduces the power required to heat the emitter to operating temperature.

However, alumina can be employed instead of steatite. If it is, the substrate is preferably coated with a film of a dielectric material having low thermal conductivity such as a dielectric glass.

Another substrate material that can be employed is fused silica.

Bonded to an exposed surface 146 of substrate 145 (see FIGS. 15 and 15A) are electrical terminals 148 and 150. Terminals 148 and 150 may be formed of a platinum and gold containing cermet obtained by printing an ink such as DuPont's 4956 on the exposed surface 146 of substrate 145 and then firing the substrate.

Bonded to the exposed substrate surface 146 with its ends overlapping and thereby electrically connected to terminals 148 and 150 is a thick film or layer 151 of an emissive, electrically resistive material. The preferred material is obtained by firing Electro-Science Labs ESL3812 ink. This ink contains a major proportion of platinum and has an operating temperature in the range of 250–300 degrees centigrade.

Additional details of emitter 134, its construction, modus operandi, and advantages are discussed at length in above-incorporated U.S. Pat. No. 5,369,277 to which the reader may refer, if desired.

Figure 14:
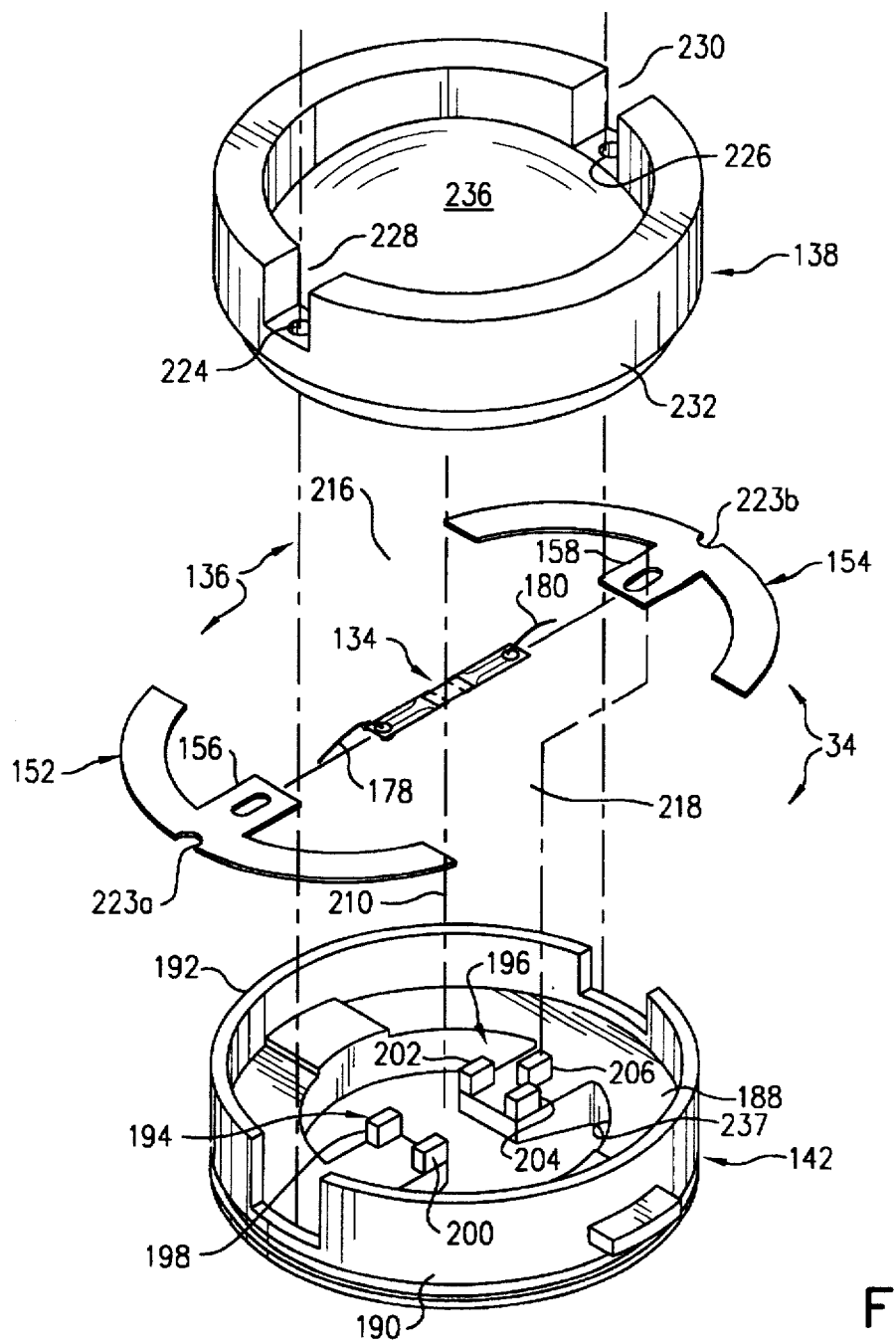
FIG. 14 is an exploded view of the infrared radiation source unit.
Figure 15:
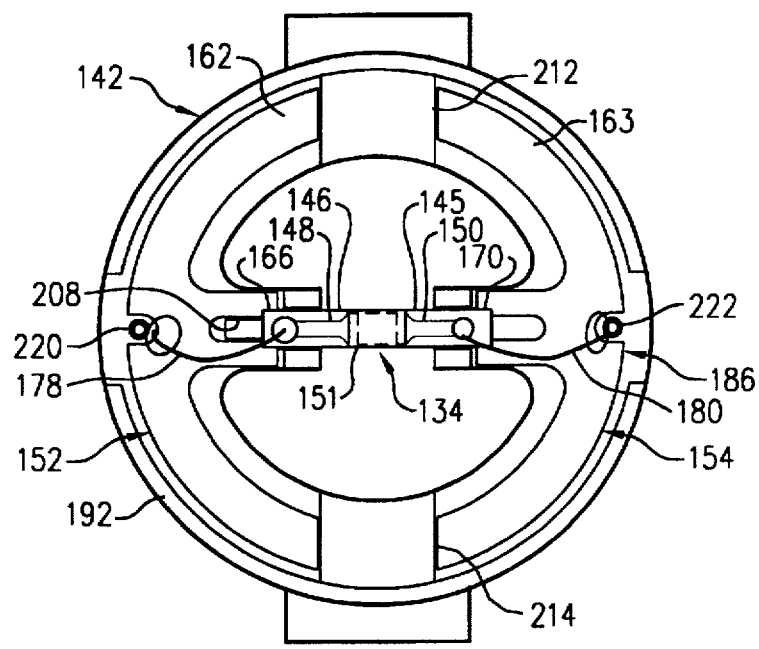
FIG. 15 is a view of the infrared radiation source unit showing certain internal components of that unit and how those components are arranged relative to each other and to the base of the unit.
Figure 15A:
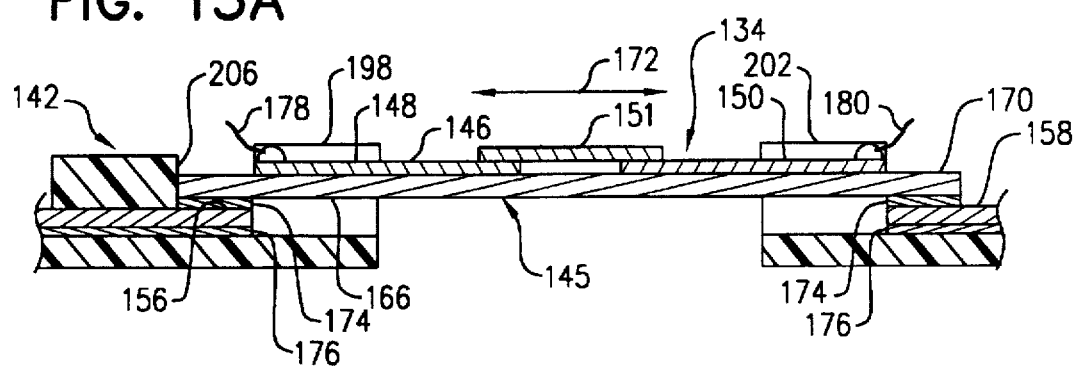
FIG. 15A is a partial section through the infrared radiation source unit showing the details of an infrared radiation emitter incorporated in that unit.

Referring now most specifically to FIGS. 14, 15, and 15A, lead frame 136 is fabricated from a conductive material such as tin-plated copper. The lead frame has two, generally similar, arcuate segments 152 and 154. Also found in lead frame 136 are emitter supports 156 and 158. Support 156 is integral with, and extends radially inward from, lead frame segment 152. Emitter support 158 is axially aligned with support 156. It is integral with, and extends radially inward from, lead frame segment 154. Lead frame segments 152 and 154 are positioned in base 142 by the arrangement of integral legs discussed in detail below.

One end 166 of emitter 134 is seated on the upper side 162 of emitter support 156, and the opposite end 170 of emitter 134 is seated on the upper side 163 of emitter support 158.

When current is applied across the emissive layer 151 of emitter 134, heating up the emissive layer and substrate 145, the substrate grows or increases in length due to thermal expansion as shown by double-headed arrow 172 in FIG. 15A; but this growth is accommodated by an elastic bonding agent rather than being constrained. As a consequence, the stresses which would be imposed upon emitter 134 if both ends were rigidly fixed are avoided, eliminating the damage to emitter 134 or complete failure of that component which might result if high mechanical stresses were imposed upon it.

Specifically, the ends 166 and 170 of emitter 134 are bonded to emitter supports 156 and 158 and the latter to base 142 with layers 174 and 176 of a high temperature RTV or comparable adhesive. RTV (room temperature vulcanizing) is a trademark for a family of silicone rubber compounds usually employed in sealing, bonding, caulking, and mold making. The preferred, cured RTV has a jellolike consistency and very low shear strength. It reduces impact-generated shock on emitter 134 but does not interfere with the ability of the emitter to expand and contract in the arrow 172 directions as the emitter heats up and cools down.

The emitter 134 of infrared radiation source 34 is energized to heat it to an operating temperature in which it emits infrared radiation in an appropriate range of bandwidths by effecting a flow of electrical current through the emissive layer 151 of the emitter from an appropriate power supply as described below. The power supply is connected to emissive layer 151 via electrical leads 178 and 180. These leads are soldered or otherwise physically and electrically connected to the emitter terminals 148 and 150 at one end and to lead frame segments 152 and 154 at their opposite ends (see FIG. 15).

The emitter/lead frame assembly 186 is installed in the base 142 of radiant energy emitting unit 34. This component is a monolithic member. The environment in which this component operates can reach an elevated temperature due to heating by the emissive layer 151 of infrared radiation emitter 134. The base is therefore fabricated of a polysulfone or comparable polymer which will remain structurally stable at the temperatures it reaches during the operation of infrared radiation source 34 and also as leads 178 and 180 are soldered to the emitter support segments 154 and 156 of lead frame 136.

Base 142, best shown in FIG. 14, has a cylindrical configuration; a platform 188; and integral, annular wall segments 190 and 192 which extend upwardly from platform 188 with base 142 in the orientation shown in FIG. 14.

Projecting in the same direction from platform 188 are two sets 194 and 196 of assembly 186-locating bosses or lugs. The spaced apart lugs 198 and 200 in set 194 and the complementary, spaced apart lugs 202 and 204 in lug set 196 embrace the opposite sides of the emitter supports 156 and 158 in the installed lead frame/emitter assembly 186. A third lug 206 of set 196 extends through an elongated slot 208 in emitter support 158. The installed assembly 186 is correctly oriented in the circumferential direction and kept from shifting relative to platform 188 by lugs 198 . . . 206. The end 166 of emitter 134 is butted against lug 206, positively locating that end of the emitter in base 142 in the spanwise, arrow 172 direction.

The assembly 186 of emitter 134 and lead frame 136 is installed in base 142 by aligning it relative to the base as shown in FIG. 14. The emitter/lead frame assembly is then displaced downwardly in the direction indicated by arrow 210 until the arcuate segments 152 and 154 of the lead frame are seated on platform 188. Radial bosses (not shown) in base 142 guide lead frame 136 relative to base 142 as the lead frame/emitter assembly 186 is installed, then and thereafter maintaining the wanted relationship between the assembly and base. Once lead frame segments 152 and 154 are seated on platform 188, the emitter/lead frame assembly 186 is retained in place by the adhesive 176 placed between lead frame segments 152 and 154 and the platform. Bosses or lugs 212 and 214 separate the commutator segments, providing gaps 216 and 218 therebetween which electrically isolate the two lead frame segments. This is necessary so that a voltage differential can be created across emitter 134 to cause operating current to flow through the emitter.

After the emitter/lead frame assembly 186 is installed and bonded to base platform 188, external leads 220 and 222 are soldered or otherwise electrically and physically connected to lead frame segments 152 and 154 with the leads being trained through peripheral lead frame notches 223a and 223b to protect the leads as source unit 34 is assembled.

Next, infrared radiation source unit cap 138 is installed. This component, shown in FIGS. 13 and 14, is cup-shaped; and it is fabricated from a polymer with a high degree of structural stability such as an acrylonitrile-butadiene-styrene (ABS).

Cap 138 is of the same diameter as base 142. It is installed by training external lead 220 through cap aperture 224 and external lead 222 through cap aperture 226 and then displacing the cap relative to base 142 in the direction indicated by arrow 210 in FIG. 14, once the cap has been oriented relative to the base as shown in that figure. External leads 220 and 222 pass through apertures 224 and 226 into notches 228 and 230 provided on opposite sides of cap side wall 232 to protect the leads. An appropriate adhesive is employed to secure cap 138 to base 142.

The mirror 140 of infrared radiation source unit 34 is formed by plating the parabolic surface 234 (see FIG. 15B) of an integral, end wall 236 of infrared radiation source unit cap 138 with a reflective coating. Typically, parabolic surface 234, which faces the emissive layer 151 of infrared radiation emitter 134, is first plated with a 2 mil thick coating of copper and then overplated with gold, the thickness of the gold layer typically being in the range of 2 μin.

Infrared radiation outputted by the emissive layer 151 of infrared radiation emitter 134 is focused and propagated as beam 132 along optical path 56 through an aperture 237 in the platform 188 of infrared radiation source unit base 142. Foreign material is kept from the interior of the infrared radiation source unit 34 by a sapphire or other infrared radiation transmitting window 238 spanning and closing aperture 237 (see FIGS. 4, 5, and 9).

Window 238 is cemented or otherwise bonded to a ledge 239 formed in the base 142 of infrared radiation source unit 34. Window positioning ledge 239 is located at the inner end of a recess 240 opening onto the exterior of base 142.

Figure 15B:
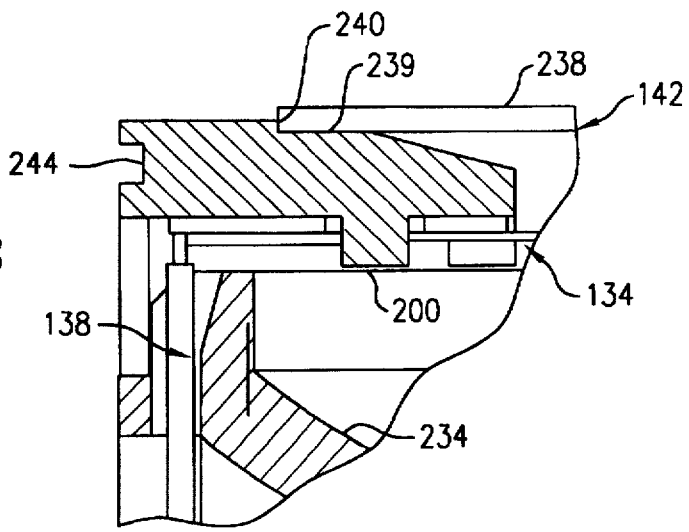
FIG. 15B is a fragmentary section through the source unit which shows the relationship of the major source unit components.

As is best shown in FIG. 15B, the O-ring component 144 of infrared radiation source unit 34 is seated in an annular recess 244 which extends around and opens on to the periphery 244 of the infrared radiation emitting unit base 142. O-ring 144 seals the gap between the infrared radiation emitting unit and transducer casing components 72 and 74 when transducer 24 is assembled as will be discussed in more detail below.

Figure 10:
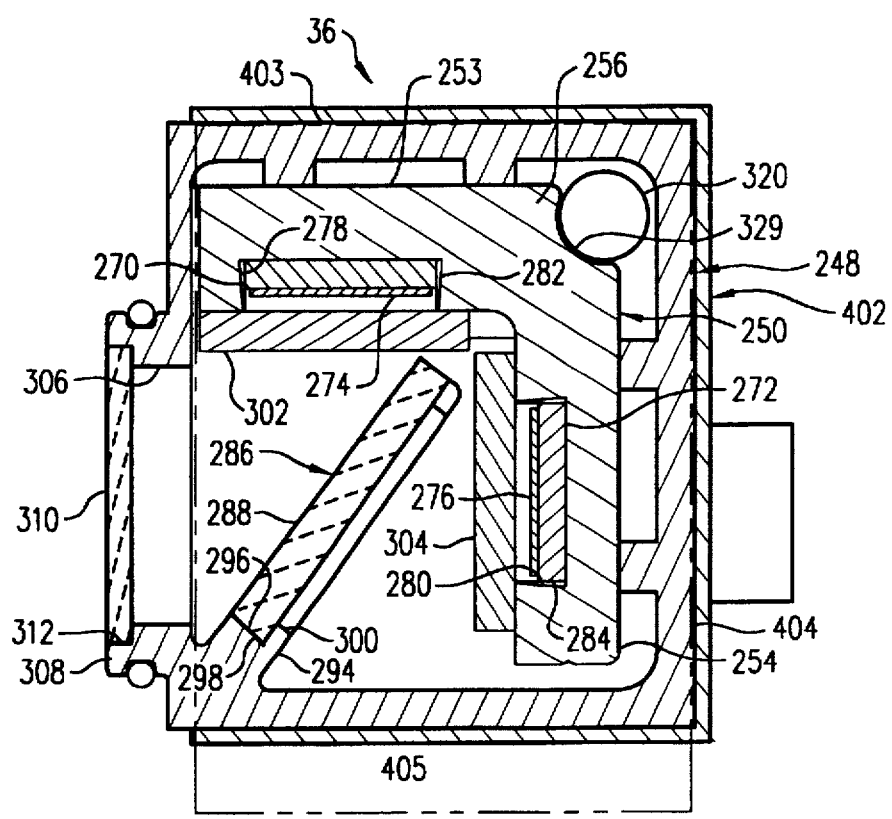
FIG. 10 is a section through the infrared radiation detector unit showing the arrangement of the unit's internal components.

Referring now to FIGS. 9 and 10, the infrared radiation detector unit 36 of transducer 24 includes a boxlike housing or casing 248. A monolithic, heat conductive, isothermal detector support and heat sink 250 is attached to a detector unit PCB 251; and the resulting support/PCB assembly 252 (see FIG. 12) is fixed to housing 248 with the detector support located in the detector unit housing. The isothermal detector support 250 is preferably extruded from aluminum because of the high heat conductivity which that element possesses. The isothermal support 250 has a generally L-shaped configuration provided by two, normally related, integral legs 253 and 254 separated by a transition section 256.

Mounted in support 250 are data and reference detectors 270 and 272. These detectors are preferably fabricated with lead selenide detector elements because of the sensitivity which that material possesses to infrared radiation having wavelengths which are apt to be of interest. Detectors 270 and 272 are described in detail in the above-cited and incorporated U.S. Pat. Nos. 4,859,858 and 4,859,859 to which the reader may refer, if desired.

Detectors 270 and 272 are connected to the power supply mentioned above and discussed in detail hereinafter to impress a biasing voltage across the identically configured and dimensioned infrared radiation sensing elements 274 and 276 of the detectors.

The two detectors 270 and 272 are mounted in recesses 276 and 280 formed in legs 253 and 254 of isothermal support 250. As shown in FIG. 9, there are annular gaps 282 and 284 between the detectors 270 and 272 and the boundaries of the detector-receiving recesses 278 and 280 in isothermal support 250. This electrically isolates the detectors from the conductive, isothermal support.

Also housed in the casing 248 of detector unit 36, and in front of data and reference detectors 270 and 272, is a beam splitter 286. The beam splitter has a generally parallelepipedal configuration. This component is fabricated from a material such as silicon or sapphire which is essentially transparent to electromagnetic energy in wavelengths of interest. The exposed front surface 288 of the beam splitter is completely covered with a coating (not shown) capable of reflecting that electromagnetic energy impinging on the beam splitter which has a wavelength longer than a selected value. Preferred is a proprietary coating supplied by Optical Coating Laboratories, Inc., Santa Rosa, California. In the illustrated exemplary embodiment of the invention, the coating will reflect to data detector 270 as indicated by arrow 290 energy having a wavelength longer than about 4 microns. The energy of shorter wavelengths is, instead, transmitted through beam splitter 286 to reference detector 272 as is suggested by arrow 292.

Beam splitter 286 is supported at equal distances from, and in identical angular relationships to, data and reference detectors 270 and 272. The detectors are offset as shown in FIG. 9 relative to the envelope of the beam 132 of infrared radiation propagated to detector unit 36 by a distance equalling that to which the rays in the envelope of the beam are displaced by bending due to the index of refraction of the beam splitter material. The beam splitter is fixed in place by epoxying or otherwise bonding the beam splitter to a support 294 which is an integral element of isothermal detector support 250. A ledge 296 toward the lower end of support 294 is engaged by the lower edge 298 of the beam splitter. This accurately positions beam splitter 286 in the wanted, identical relationships to data and reference detectors 270 and 272 with the advantage that the heretofore employed subsequent adjustment of the beam splitter orientation is not required. An aperture 300 through support 294 allows infrared radiation passed by beam splitter 286 to reach reference detector 272.

Bandpass filters 302 and 304, also supplied by Optical Coating Laboratories, Inc., limit the infrared radiation energy respectively reflected from and transmitted by beam splitter 286 and impinging upon data and reference detectors 270 and 272 to energy in selected bandwidths. In the exemplary embodiment and use of the invention under discussion and depicted in the drawing, the reference detector filter 304 is centered on a wavelength of 3.681 μm and has a half power bandwidth of 0.190 μm. That filter transmits maximum energy near the carbon dioxide band absorbed by data detector 270. This absorption of maximum energy in an adjacent bandwidth is selected so that the output from reference detector 270 will be at least as large as the output from data detector 272. This contributes markedly to the accuracy of the gas concentration indicative signal subsequently obtained by ratioing the data and reference signals.

The data detector bandpass filter 302 is centered on a wavelength of 4.260 μm and has a bandwidth of 0.10 μm. This is two times narrower than the bandwidth of filter 304. The carbon dioxide absorption curve is fairly narrow and strong, and bandpass filter 302 centers the transmission band within that absorption curve. Therefore, if there is a change in carbon dioxide level in the gas(es) being analyzed, the maximum modulation for a given change in carbon dioxide level is obtained.

Data and reference bandpass filters 302 and 304 are bonded to the legs 253 and 254 of isothermal detector support 250 in overlying relationship to those recesses 278 and 280 in which data and reference detectors 270 and 272 are mounted.

All of that energy over the entire and same span of infrared radiation beam 132 propagated along optical path 56 and reaching detector unit 36 with a wavelength longer than the selected cutoff is reflected to data detector 270. Similarly, that energy with a shorter wavelength is transmitted through beam splitter 286 to reference detector 272. Because of this, the physical relationship of detectors 270 and 272 discussed above, and the dimensioning and configuration of the energy intercepting sensing elements 274 and 276 of those detectors, both detectors "see" the same image of the beam 132 of electromagnetic energy. This contributes markedly to the accuracy afforded by detector unit 36.

In other words, and optically, with the data and reference detectors 270 and 272 accurately positioned relative to each other and beam splitter 286 in the novel manner just described, these components function as if the two detectors were precisely stacked one on top of the other. Therefore, electromagnetic energy from the entire compass of beam 132 reaches both detectors in spatially identical fashion.

By making the two detectors 270 and 272 spatially coincident from the optical viewpoint and electronically sampling the detector outputs at the same times, the adverse effects on accuracy attributable to foreign material collecting on either of the above-described airway adapter optical windows 58 and 60, the window 238 of source unit 34, or a subsequently described window of detector unit 36 are also eliminated by the subsequent ratioing of the data and reference detector output signals.

The electromagnetic energy in the beam 132 propagated along optical path 56 reaches beam splitter 286 through an aperture 306 in the front wall 308 of detector unit casing 248. An infrared radiation transparent window 310—again typically made of sapphire—spans aperture 306 and keeps carbon dioxide and other foreign material from penetrating to the interior of detector unit casing 248 before the detector unit is installed in transducer housing 32 and if that housing is subsequently unsealed. Window 310 is seated in a recess 312. That recess is formed in a barrel-shaped extension or segment 313 of detector unit casing front wall 308 and surrounds radiation transmitting aperture 306. The window is bonded to the casing in any convenient and appropriate manner.

Infrared radiation beam 132 is focused down (or narrowed) by mirror 140, which allows a detector unit window 310 much smaller in diameter than source unit window 258 to be employed. Because of the expense of sapphire and comparable window materials, the cost savings is appreciable.

The operation of transducer 24 as thus far described is believed to be apparent from the drawings and the foregoing, detailed description of the transducer. Briefly, however, electromagnetic energy in the infrared portion of the spectrum is generated by heating the emitter 134 of infrared radiation source unit 34. The energy thus emitted is propagated toward the concave emitter unit mirror 140 as shown by arrow 314 in FIG. 9. Mirror 140 focuses this energy and propagates the energy as beam 132 along optical path 56 across the path of the gas(es) flowing through airway adapter 22.

Energy in a species specific band is absorbed by the gas of interest flowing through the airway adapter (typically carbon dioxide) to an extent proportional to the concentration of that gas. Thereafter, the attenuated beam of infrared radiation passes through the aperture 306 in the front wall 308 of the detector unit casing 248, is intercepted by beam splitter 286, and is either reflected toward data detector 270 or transmitted to reference detector 272. The bandpass filters 302 and 304 in front of those detectors limit the energy reaching them to specified (and different) bands. Each of the detectors 270 and 272 thereupon outputs an electrical signal proportional in magnitude to the intensity of the energy striking that detector. These signals are amplified and conducted to SPCDU 26 and there typically ratioed to generate a third signal accurately reflecting the concentration of the gas being monitored. The signal processing circuitry used for this purpose is independent of airway adapter 22 and transducer 24, is not part of the present invention, and will accordingly not be disclosed herein.

The preferred, lead selenide data and reference detectors 270 and 272 are extremely temperature sensitive. It is therefore critical that these two detectors be maintained at the same temperature, preferably within the above-mentioned tolerance of not more that 0.01° C. As discussed above and in more detail hereinafter, transducer housing 32 is preferably heated to keep condensation from forming on the infrared radiation-transmitting windows of transducer 24 and airway adapter 22. The detector temperature is maintained independently of the transducer housing temperature because of the thermal perturbations to which the transducer housing may be subjected.

Detectors 270 and 272 are maintained at the selected operating temperature by a detector heating system 316 (FIG. 29B) which includes a detector heater 318 (FIG. 12), a temperature monitoring thermistor 320 (FIGS. 9 and 10), and an operating/control circuit (not shown) which is located in SPCDU 26.

Detector heater 318 is composed of an L-shaped array of two orthoganally related, resistive, thick film heating elements 326 and 328 fabricated by printing platinum-gold conductors and a rutheniumbased glass frit resistance element on a printed circuit board 251 hereinafter referred to as a preamplifier board (see FIG. 12). Preamplifier board 251 is assembled to detector support/heat sink 250 with resistive heating elements 326 and 328 facing and in heat transfer relationship with component 250. Consequently, and because component 250 is fabricated of a material with high thermal conductivity, there is a flow of thermal energy through that component which allows the data and reference detectors 270 and 272 to be precisely maintained at the same, selected temperature.

Temperature sensing thermistor 320 is seated in a complementary, transversely extending recess 329 opening onto the side of detector support/heat sink 250 opposite detectors 270 and 272 at the junction between isothermal support legs 253 and 254. Thermistor 320 is of conventional construction.

The detector heater 318 and thermistor 320 are connected to terminals on preamplifier board 251 and, via those terminals and cable 28, to the detector heater drive circuit in SPCDU 26. This circuit operates heater 318 on a schedule which keeps the temperature of data and reference detectors 270 and 272 as measured by thermistor 320 constant at the selected level.

Figure 26:
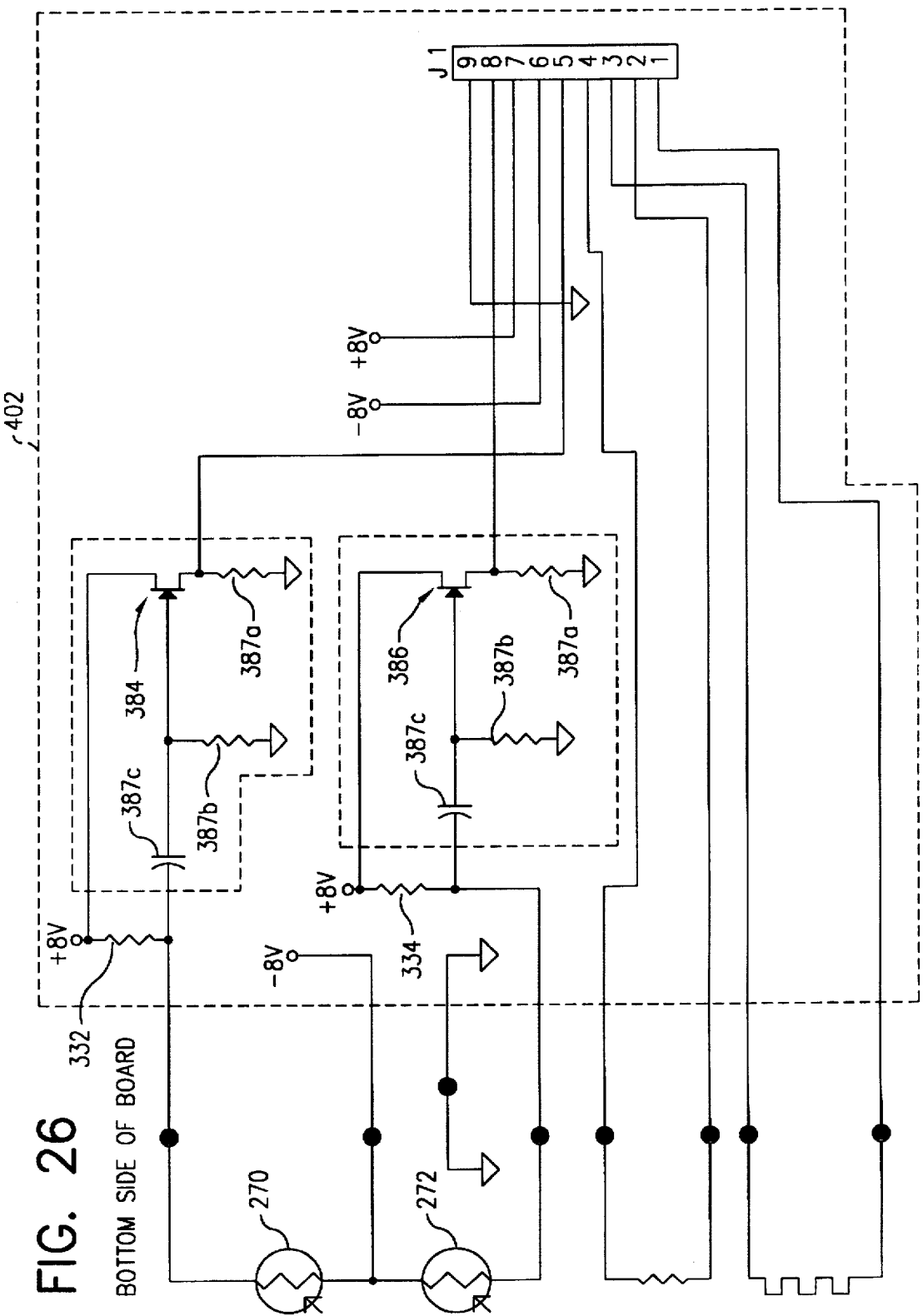
FIG. 26 is an electrical schematic of the infrared radiation detectors in the FIG. 1 transducer, the detector heater and an associated temperature sensor, and a preamp printed circuit board; these components are all part of the detector unit.

As is also shown in FIG. 26, resistors 332 and 334 are connected in series with data detector 270 and reference detector 272. These resistors bias the detectors to the maximum extent. This is important because the sensitivity of those detectors to energy in the infrared portion of the electromagnetic spectrum is so bias dependent. Therefore, as the bias is increased, the magnitude of the signal that can be outputted for a given quantum of impinging energy is increased.

Figure 27:
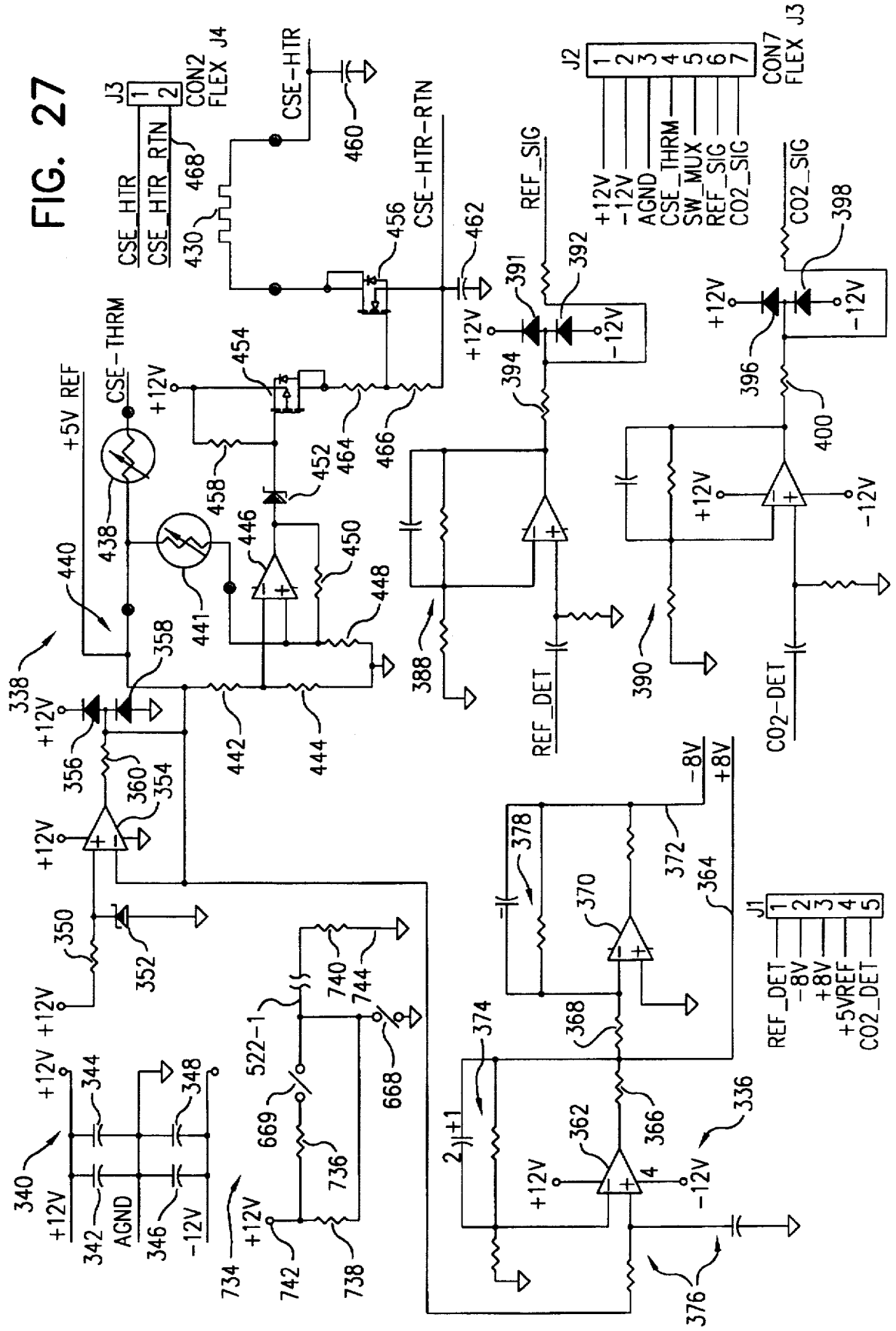
FIG. 27 is an electrical schematic of the ISA multipurpose PCB shown in FIG. 7.

Bias resistors 332 and 334 (FIG. 26) are driven by a bias voltage circuit identified by reference character 336 (See FIG. 27). The bias voltage circuit is connected to an external power supply (not shown) through a reference voltage circuit 338 and a circuit 340 which provides electrostatic discharge (ESD) protection and voltage decoupling and is composed of a network of capacitors 342 . . . 348. This circuit is located on a PCB 349 which will hereinafter be referred to as a "multipurpose board".

Reference voltage circuit 338 converts the 12 volt power to a buffered, 5V power supply. The reference voltage circuit includes a voltage dropping resistor 350 and a precision reference voltage diode 352.

The current output from diode 352 is very limited; and the current flow is accordingly increased to a useable level by the operational amplifier 354 in reference voltage circuit 338. Also incorporated in this circuit are diodes 356 and 358 which, in cooperation with resistor 360, provide electrostatic discharge (ESD) protection for the reference voltage circuit 338.

Plus 5V power is supplied by reference voltage circuit 338 to an operational amplifier 362 in bias voltage circuit 336 to buffer or increase the voltage to +8V, which is available on lead 364. The +8V power is also applied through resistors 366 and 368 to a second operational amplifier 370 connected as an inverter. This inverter makes −8V power available from bias voltage circuit 336 on lead 372. The +8V power from lead 364 is applied to one side of the data detector 270 and one side of the reference detector 272, and the −8V power is applied from lead 372 to the opposite sides of those detectors.

In addition to the components just discussed, bias voltage circuit 336 includes three conventional R-C filters 374, 376, and 378 which eliminate noise.

Referring now to FIG. 26, the data and reference signals outputted by data and reference detectors 270 and 272 are routed to field effect transistors (FET's) 384 and 386 configured by resistors 387a and 387b and capacitors 387c as source followers. Data detector 270 and reference detector 272 are not shielded, and the outputs from these detectors have a high impedance. Consequently, the output leads from the two detectors will pick up 60 Hz signals, adversely affecting the accuracy of transducer 24 to an unacceptable extent unless steps are taken to keep this from occurring. Unity gain source followers 384 and 386 reduce the impedance to a very low level, limiting the 60 Hz signals components that are picked up to an acceptable level. The impedance is typically reduced from hundreds of Kohms to around 5 Kohms.

The low impedance signals from source followers 384 and 386 are amplified by data and reference signal amplifiers 388 and 390 (see FIG. 27). These amplifiers are conventional and are employed to increase the voltage of the detector output signals, typically with a gain of 58.6 V/V in the data detector 270 output signal and a gain of 45.4 V/V in the reference detector 272 output signal. The amplified signals are routed from amplifiers 388 and 390 to SPCDU 26 through cable 28. The details of amplifiers 388 and 390 are not part of the present invention; and these amplifiers are described at length in above-incorporated U.S. Pat. No. 5,153,436 to which the reader may refer, if desired. Accordingly, the amplifier circuitry will not be described herein, and the circuit components have not been individually labeled in the drawings.

Like the reference voltage circuit 338 discussed above, ESD protection is provided to the outputs of data detector signal amplifier 388 and reference detector signal amplifier 390 by diode/resistor circuits. The ESD protection circuit of data detector signal amplifier 388 is composed of diodes 391 and 392 and a resistor 394, and the ESD protection circuit of reference detector signal amplifier 390 is composed of diodes 396 and 398 and resistor 400.

Referring now to FIG. 9, the casing 248 of detector unit 36 as thus far described is in part surrounded by a conductive sheet metal shield 402 to provide EMI protection to the electrical and electronic components of that unit. This shield has segments which cover the top, rear end, bottom, and side walls 403, 404, 405, and 406 of casing 36 with one shield segment 410 overlying and providing EMI protection to the components on preamplifier board 251.

Figure 5:
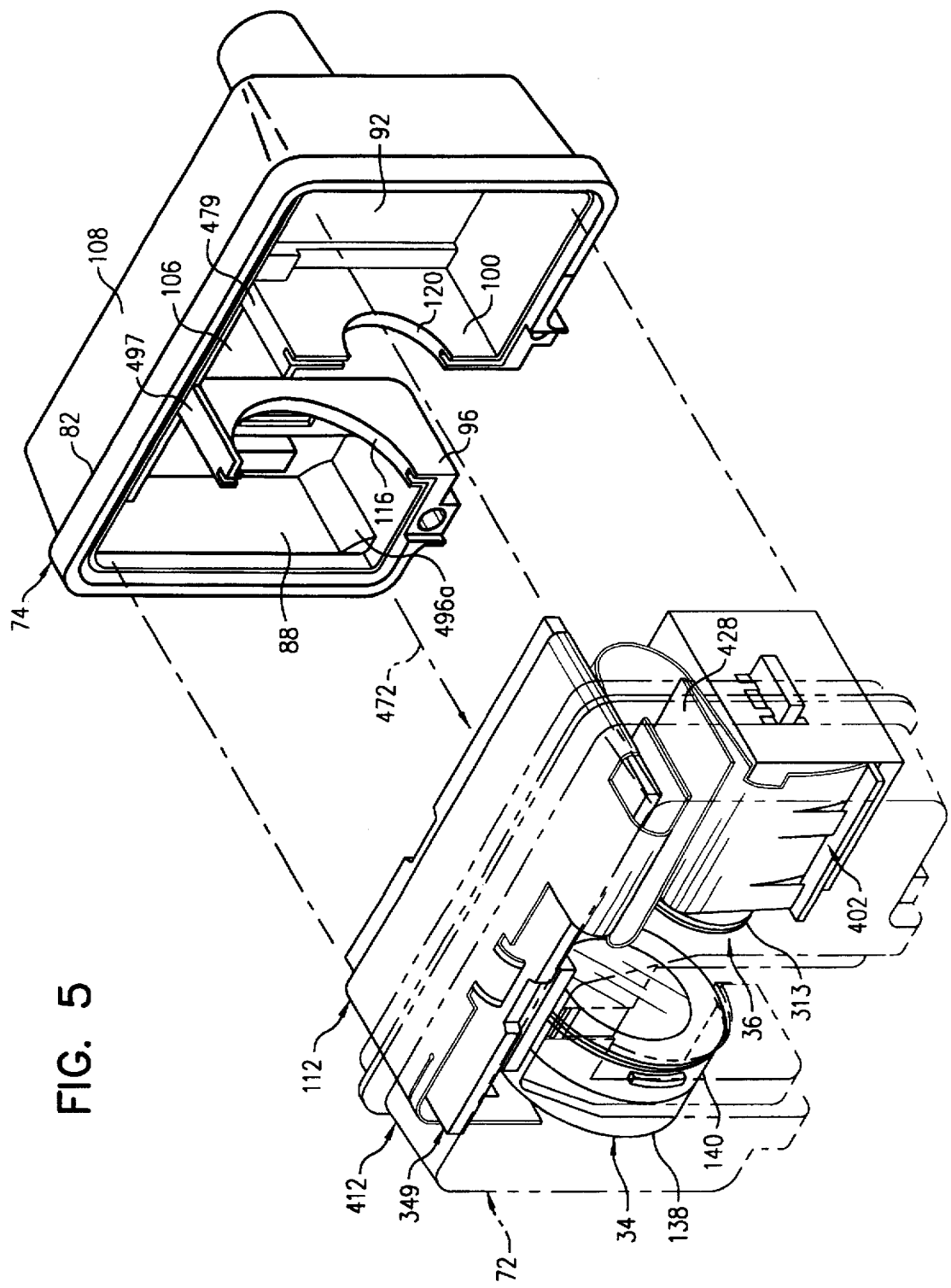
FIG. 5 is an exploded view showing how the second of the transducer casing components is assembled to the to the first of those casing components after the ISA is installed.
Figure 16:
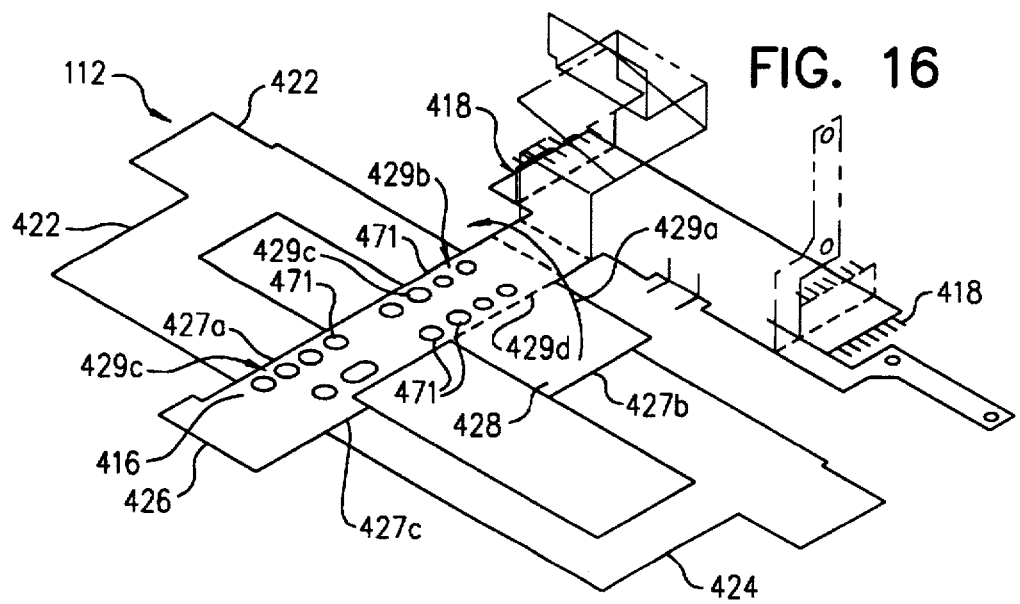
FIG. 16 is a generally perspective view of a multilead flex connector which is a component of the ISA.

Infrared radiation source unit 34, detector unit 36, and multipurpose board 349 are joined into an integrated subassembly (ISA) 412 by the folded flex connector 112 (see FIGS. 4 and 5 and especially FIG. 16). Flex connector 112, shown by itself in FIG. 16, consists of a flexible polymeric matrix 416 in which electrical leads or conductors are embedded. Representative ones of these leads are shown generally schematically in FIG. 16 and identified by reference character 418. Leads 418 are also shown—and named—in FIGS. 29A and 29B.

Figure 29:
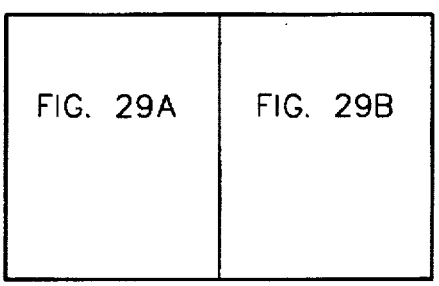
FIG. 29 shows the relationship between FIGS. 29A and 29B which, together, constitute a wiring diagram of the gas analyzer system illustrated in FIG. 1.
Figure 29A:
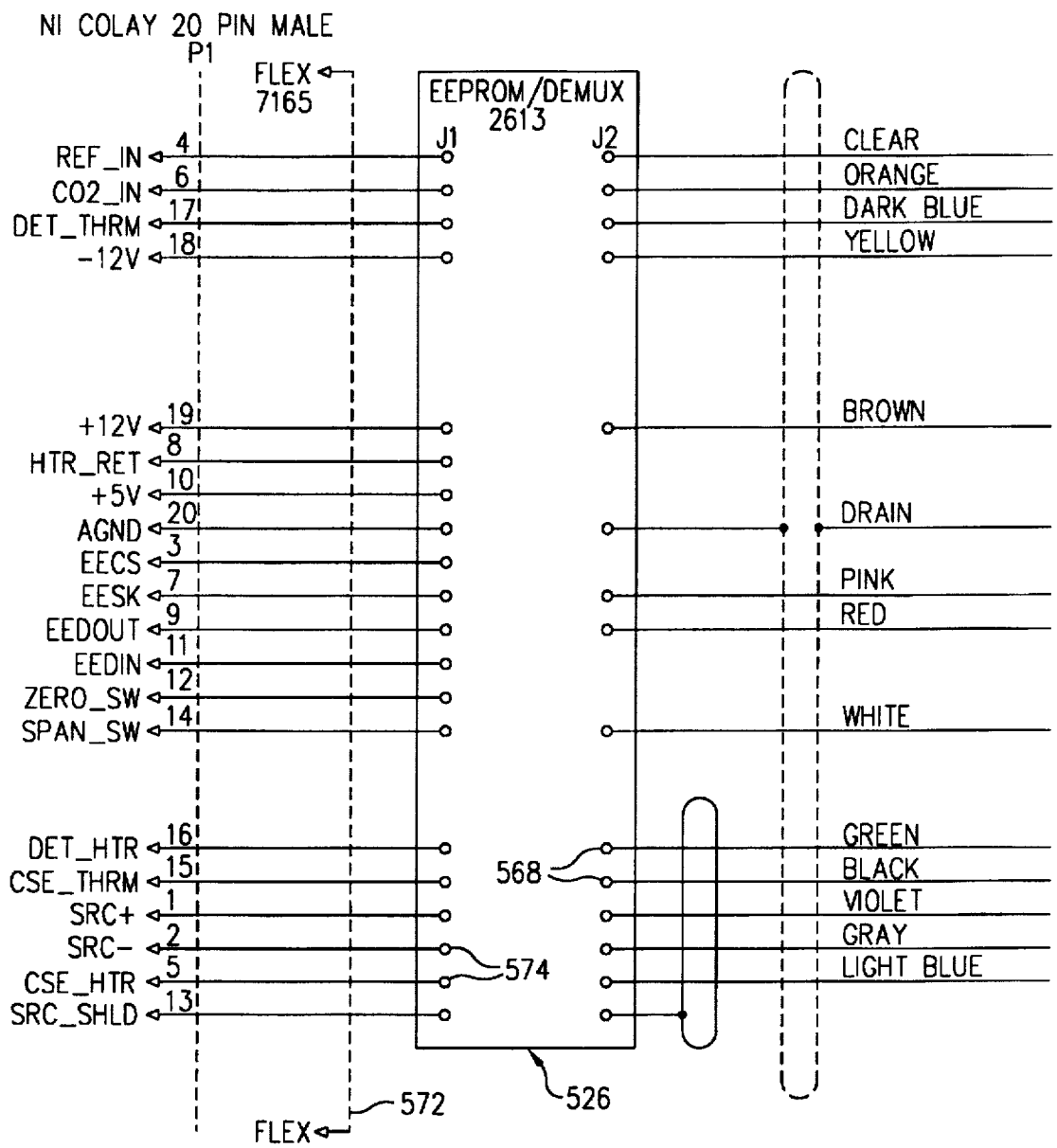
Figure 29B:
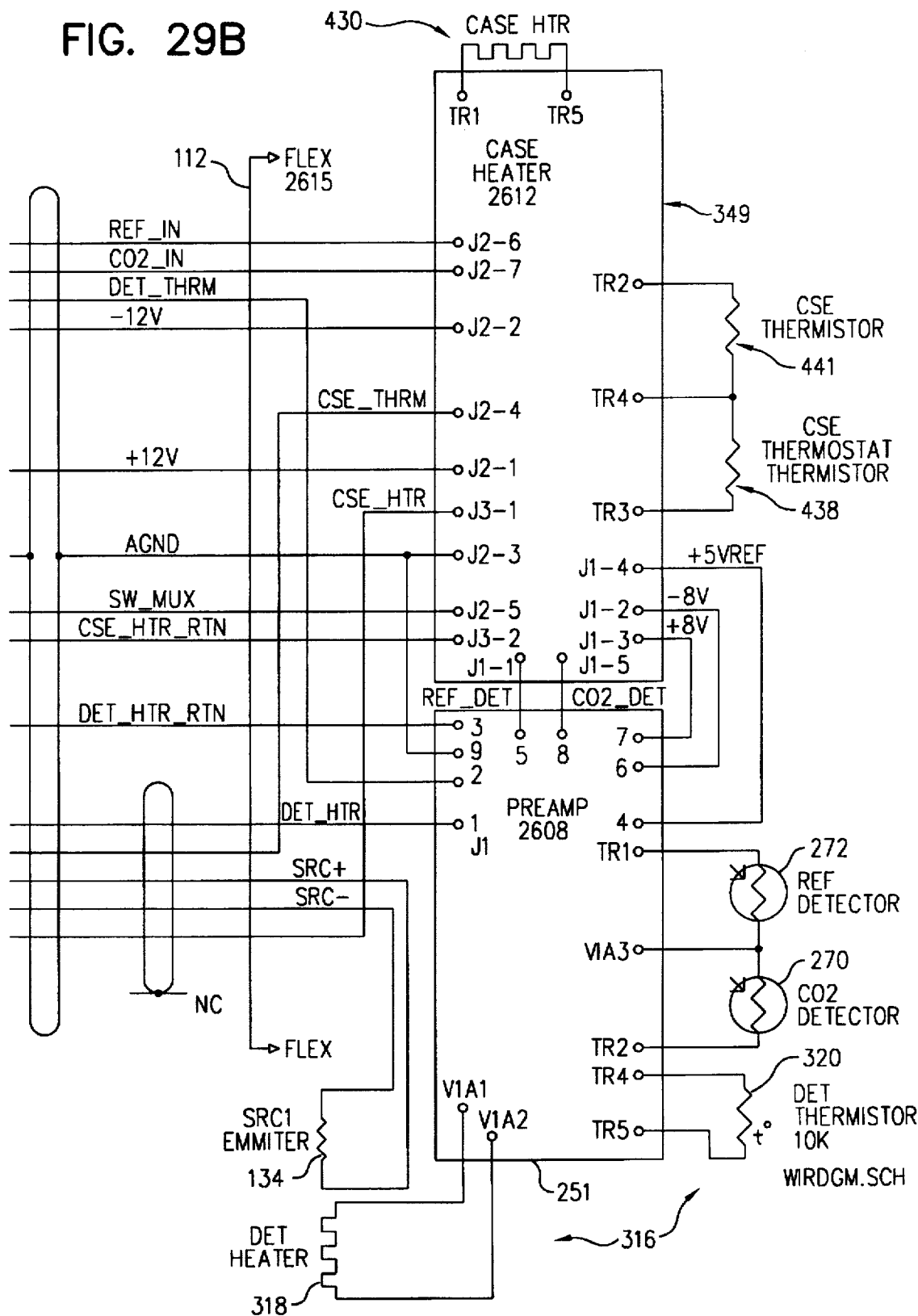

Flex connector leads 418 are connected to infrared source unit 34, infrared radiation detector unit 36, and multipurpose board 349 as shown in FIG. 29A and 29B; and the flex connector is folded as shown in FIG. 11. As is also shown in FIG. 11, the flex connector extends from the top side 420 of PCB 349 downwardly through transducer casing 32. Beneath PCB 349, flex connector 414 is folded into a U-shaped configuration and then trained down alongside infrared radiation detector unit 36 and connected to the appropriate terminals—shown in FIG. 29—of preamplifier board 330.

As shown in FIG. 16, terminal segments 422 and 424 extend from what can be considered the main part 426 of flex connector 414. These terminal segments allow integrated subassembly 412 to be electrically connected to test equipment (not shown) provided to test the integrated subassembly and electrically driven components of the integrated subassembly. These flex connector extensions or terminal segments 422 and 424 are removed at lines 427a–c after testing is completed and before integrated subassembly 412 is installed in transducer casing 32.

Reference character 428 in FIG. 16 identifies an insulator tab which can be folded over as indicated by arrow 429a to isolate one of the two solder pads 429b on PCB 349. The other solder pad is identified by reference character 429c, and the fold line is identified by reference character 429d.

This provision of a subassembly which contains all of the electrical components of transducer 24 is a significant feature of the present invention. The operation of the transducer can be tested before the transducer is assembled, which is an important, cost saving advantage from the manufacturing viewpoint.

With a gas such as a patient's exhaled breath flowing through the sampling passage 47 in airway adapter 22 (see FIGS. 2 and 9), moisture can condense out of the surrounding environment and collect on the optical windows 58 and 60 of the airway adapter and/or the windows 238 and 310 of transducer 24. The result may be a degradation in performance and loss of accuracy.

This problem is solved by maintaining the transducer housing and airway adapter windows 58, 60, 238, and 310 at an elevated, above-dewpoint temperature, preferably in the range of 42°–45° C., during the sampling or monitoring process. This is accomplished with a resistance-type transducer casing heater 430. The casing heater is mounted in, and closes, an opening 432 in transducer casing 26 at the upper end 434 of the gap 66 between transducer casing end sections 62 and 64 (see FIGS. 4A and 8). Resistance heater 430 keeps transducer casing 32 and the airway adapter 22 assembled to transducer 24 at the desired, higher than dewpoint temperature in the sampling passage 47 of airway adapter 22 by circuitry (not shown) in SPCDU 26 which will typically be set to maintain the case temperature at 45° C. in that exemplary application of the invention under discussion. A thermistor 438 (see FIG. 29B), typically set to 60° C., is provided as a fail safe safety valve. Thermistor 438 shuts off heater 430 if the SPCDU circuitry should for some reason allow the airway adapter/transducer case temperature to go significantly above the 45° C. or other selected nominal operating temperature.

Figure 17:
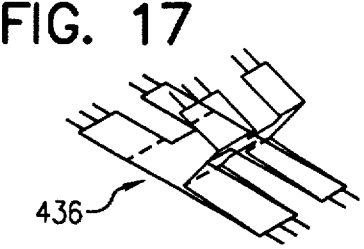
FIG. 17 is a generally perspective view of a second, multilead flex connector utilized to electrically connect the circuit board of the ISA to a heater which is employed to prevent condensation from forming on the infrared radiation transmitting windows of the FIG. 2 airway adapter.

Casing heater 430 is a component of integrated subassembly 412. Like the detector data and reference heating elements 326 and 328, heater 430 is fabricated by printing a high resistance material such as a ruthenium-based glass frit and platinum-gold conductors on a ceramic substrate. The casing heater is connected to multipurpose PCB 349 by the flex connector shown in FIG. 17 and identified by reference character 436. This facilitates the assembly of transducer 24 and, also, allows the operation of transducer casing heater 430 to be checked at the same time as, and in association with, the other electrical and electronic components of transducer 24.

As indicated above, case heater 430 is decoupled from and controlled independently of detector heater 318 so that the thermal perturbations to which airway adapter 22 and transducer housing 32 may be subjected will not affect the accuracy of the temperature sensitive lead selenide detectors 270 and 272. The operation of case heater 430 is controlled by a case thermistor 438. That thermistor is mounted on the top or back side 439 of the case heater. Thermistor 438 is incorporated in a cost saving, reliability increasing electronic thermostat 440 (see FIG. 27) which is located on ISA multipurpose PCB 349 (see FIG. 8). A second thermistor 441 (FIG. 29B) is provided as a backup for case thermistor 438 so that case heater 430 will not stay on and damage heat sensitive transducer components if thermistor 438 fails.

Referring still to FIG. 27, electronic thermostat 440 is powered from reference voltage supply circuit 338 through a voltage divider composed of resistors 442 and 444. The voltage divider drops the +5V output from reference voltage circuit 338 to a level (typically 2.5V) appropriate for the operation of electronic thermostat 440. The output from the voltage divider and the thermistor 438 of case thermostat 440 are connected to the input side of an operational amplifier 446 configured as a comparator. Also connected to the input side of operational amplifier 446 is a temperature reference resistor 448 and a feedback resistor 450 employed in conventional fashion to provide hysteresis in the operation of operational amplifier comparator 446.

As long as the temperature sensed by thermistor 438 does not exceed the selected level, the bridge formed by temperature reference resistor 448 and thermistor 438 is balanced; and the series circuit of voltage divider 442/444, operational amplifier comparator 446, zener diode 452, FET 454, FET 456, and case heater 430 is essentially a short circuit. Current accordingly flows through the case heater; and the transducer housing 32 and airway adapter 22 are heated. In the event of a primary (SPCDU) control circuit failure and if the setpoint temperature is exceeded, the resistance of thermistor 438 changes; and the reference temperature resistor/thermistor bridge becomes unbalanced. Operational amplifier comparator 446 thereupon turns off FET's 454 and 456, and the supply of operating current to case heater 438 is interrupted.

Case heater 430 will stay "off" until it cools down and the temperature sensed by thermistor 438 reaches the lower hysteresis point of electronic thermostat 440. At that point, operational amplifier comparator 446 turns FET's 454 and 456 back on, reactivating case heater 430. This on-off cycle is repeated at intervals which keep the set temperature at a selected level, typically around 60° C.

As illustrated in FIG. 27, the zener diode 452 mentioned above is connected in series between the output of operational amplifier comparator 446 and the first FET 454. This diode ensures that operational amplifier 446 goes to the plus rail and turns off FET's 454 and 456 when the thermistor/reference resistor bridge 438/448 becomes unbalanced.

In addition to the circuit components discussed above, electronic thermostat 440 includes a conventional pull-up resistor 458 and capacitors 460 and 462 which are connected to ground. These capacitors and resistor 458 provide ESD protection to the electronic thermostat 440.

The second FET 456 and resistors 464 and 466 constituting a voltage divider on the input side of FET 456 are not essential to the operation of thermostat 440. FET 456 and the circuit in which it is incorporated are employed only so that a negative voltage can be made available on the lead 468 also labeled CSE htr rtn in FIG. 27. The voltage on lead 468 ensures that the gate/source voltage does not exceed the level which FET 456 can safely handle.

As suggested above and shown in FIG. 27 and FIG. 29B, electronic thermostat 440 and transducer casing heater 438 are connected to signal processing/display and control unit 26 by the leads labeled CSE thrm, CSE htr, and CSE htr rtn. Consequently, the control of case heater 438 by case thermostat 440 is superimposed on the operation of the case heater dictated by the programming of SPCDU 26.

Referring now primarily to FIGS. 4 and 5, the assembly of transducer 24 is effected by soldering leads 522, 529, and 536 of cable 28 to appropriate ones of the terminals 471 of multipurpose board solder pads 429b and 429c, folding insulator pad 428 over solder pad 429b, and then installing integrated subassembly 412 in transducer housing component 72 as indicated by arrow 470 in FIG. 4. Then, the second transducer housing component 74 is slid on to the integrated subassembly as indicated by arrow 472 in FIG. 5 and adhesively bonded to the companion casing component 72.

Figure 6:
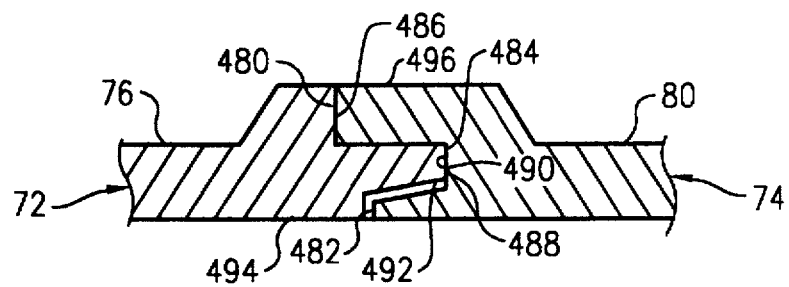
FIG. 6 is a partial section through the transducer casing, showing how the lips of the casing components are configured in accord with the principles of the invention to keep an adhesive employed to bond those components together from escaping to the exterior of the casing.

As shown in FIG. 6, there is a tongue-and-groove relationship between the peripheral rim 76 of transducer housing component 72 and the rim 80 of housing component 74. The groove, identified by reference character 478, is formed in the rim 80 of housing component 74 and opens onto the exposed edge 480 of that rim. Groove 478 has a tapered, trapezoidal configuration; and the rim segment 482 on the inner side of the rim is foreshortened.

The tongue, identified by reference character 484, is configured to complement groove 478; and it protrudes from the rim 76 of transducer housing component 72. Tongue 484 facilitates the assembly of transducer 24 by aligning casing component 74 with casing component 72 as component 74 is moved into place.

With integrated subassembly 412 assembled between transducer housing components 72 and 74 in the manner just discussed, the outer, exposed segment 480 of rim 80 abuts the outer segment 486 of rim 80; and the end 488 of tongue 484 abuts the inner end 490 of the groove 478 in rim 80 with a gap 492 between tongue 484 and groove 478. Gap 492 opens onto the inner side 494 of transducer housing 32. This groove accommodates the epoxy adhesive which is employed to bond transducer housing components 72 and 74 together. The novel tongue-and-groove arrangement just described keeps any excess adhesive from leaking to the exterior 496 of transducer housing 32.

With the transducer 24 assembled, infrared radiation source unit 34 and detector unit 36 are sealed in transducer casing compartments 84 and 86. Internal locator bosses in the two compartments (as exemplified by that boss 496a in compartment 84 shown in FIG. 5) and a detector unit guide 496b (FIG. 9) accurately align infrared radiation emitter 134 and beam splitter 286 along optical path 56. Flex connector 112, multipurpose ISA board 349, and casing heater 430 are housed in the passage 110 between infrared radiation source and detector compartments 84 and 86 with the case heater seated on (and bonded to) case heater seat elements 497 in transducer case opening 432 at the inner end of the gap 66 into which airway adapter 22 fits. The seat elements 497 in transducer casing component 74 are shown in FIG. 5 (there are comparable case heater seats (not shown) in transducer casing component 72). The case heater covers opening 432 and is located for intimate contact with, and the efficient transfer of heat to, airway adapter 22 (see FIGS. 8 and 9).

Figure 8:
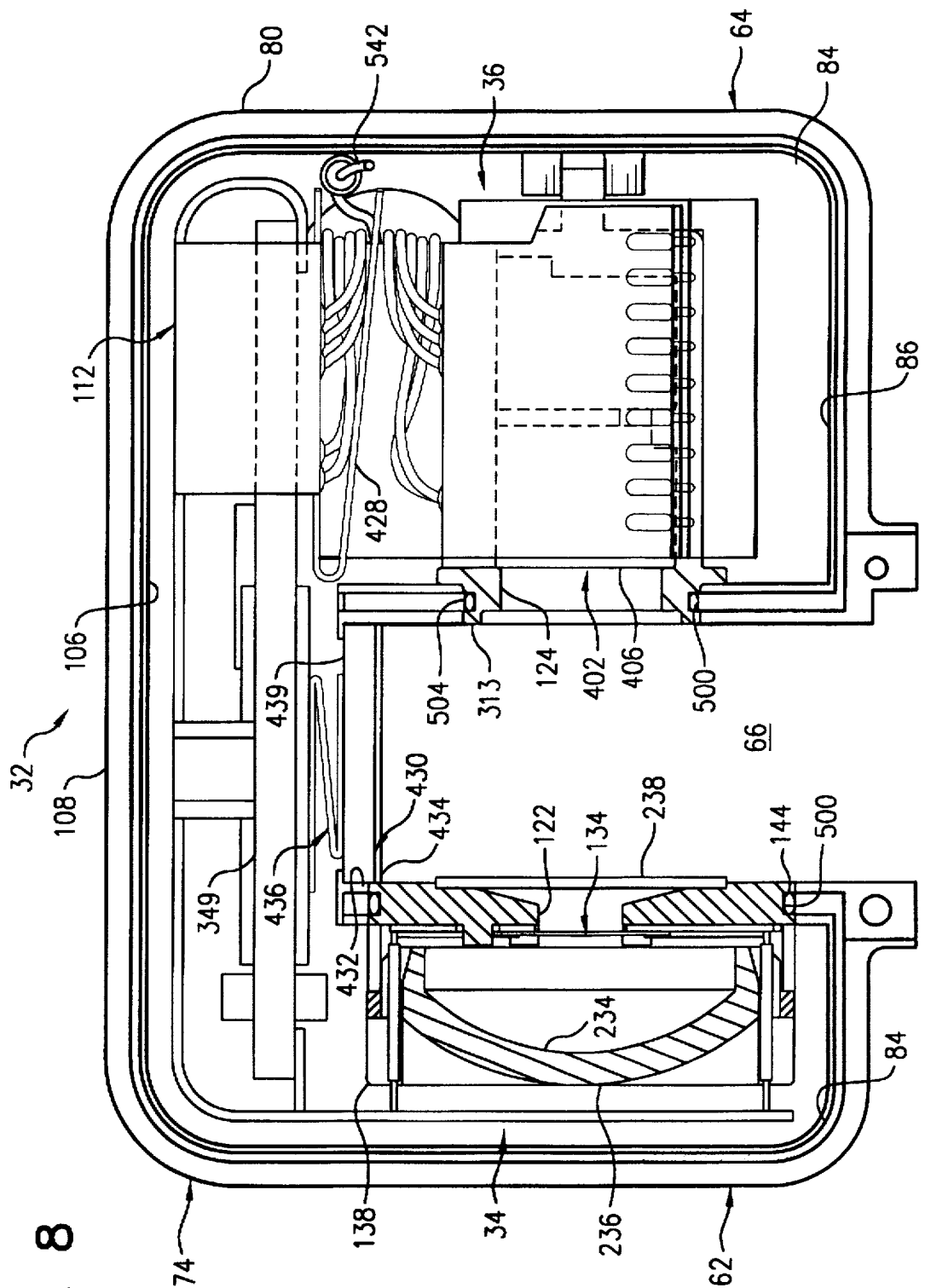
FIG. 8 is a section through the transducer showing from a different perspective the arrangement of the internal transducer components in the transducer casing.

As is suggested by FIGS. 4 and 5 and shown in FIGS. 8 and 9, the assembly of transducer housing elements 72 and 74 in embracing relationship with the opposite sides of integrated subassembly 412 results in there being a gap 498 between infrared radiation emitter unit 34 and the perimeter of the infrared radiation passing aperture 122 in transducer housing inner end wall 126. Gap 498 is sealed by O-ring 144 as discussed above by virtue of the O-ring being seated on a flat surface 500 which surrounds aperture 122. As is best shown in FIG. 9, O-ring 144 completes the isolation of the infrared radiation source compartment 84 in transducer housing 32 from the surrounding environment.

The transducer housing compartment 86 in which infrared radiation detection unit 36 is housed is in like manner isolated from the surrounding environment to keep out carbon dioxide and other foreign material by similarly functioning O-ring 144. O-ring 144 is seated in a groove 504 extending around and opening onto the periphery of detector unit casing front wall extension 313 (see FIG. 9). With the components of transducer 24 assembled and integrated subassembly 412 confined between transducer housing components 72 and 74, O-ring 144 is seated on a flat surface 506 which surrounds the gap 508 between detector extension 313 and the aperture 124 in transducer casing inner end wall 128. This effectively isolates detector compartment 86 from the surrounding environment and keeps unwanted, accuracy-effecting carbon dioxide and other foreign material from that compartment.

As discussed above, the transducer housing components and O-ring seal arrangement just described have the virtue of eliminating one of the relatively expensive sapphire windows employed in the transducer described in those transducer-disclosing patents above incorporated by reference. Further, those windows that are employed have a flat, inexpensive edge (see FIG. 9) rather than the costly stepped configuration heretofore employed. They are consequently much easier and less expensive to manufacture than the stepped edge windows employed in the patented transducers. In addition, the present arrangement has the advantage of holding the number of transducer housing components with a consequent reduction in transducer assembly costs. Also, the two-component transducer casing construction and the assembly method described above reduce manufacturing costs by holding to a minimum the number of casing components that have to be sealed together. of particular importance is that the novel sealing arrangement just discussed which keeps carbon dioxide in the ambient surroundings from leaking into the detector unit cavity and causing an error in the detector generated signal indicative of the concentration of carbon dioxide in the sample being assayed.

Figure 21:
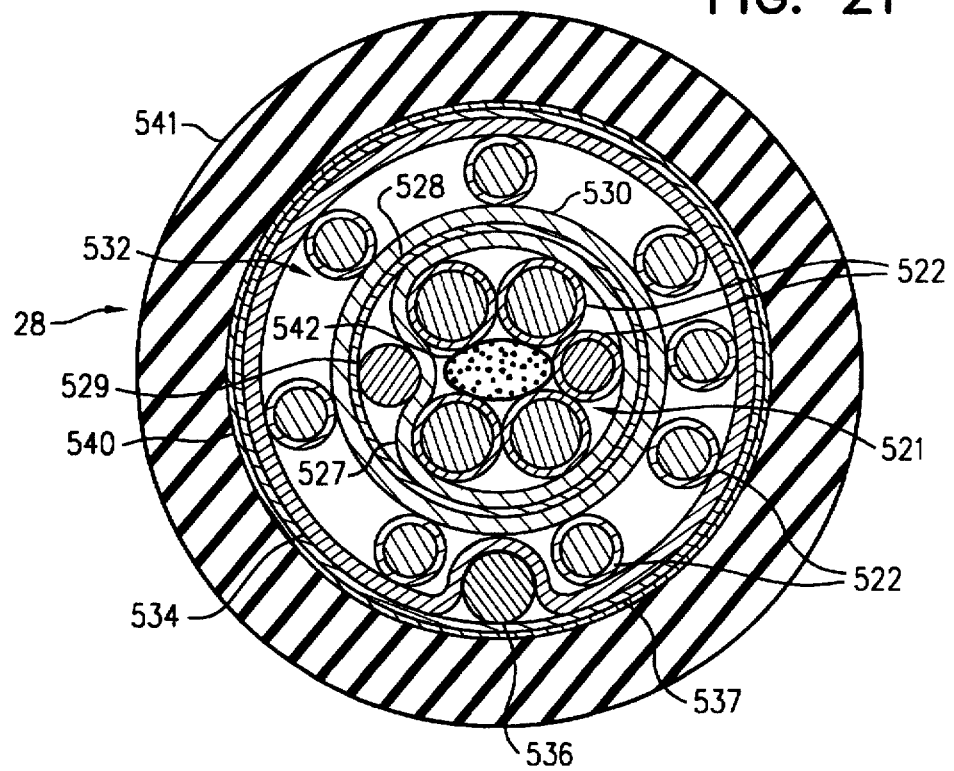
FIG. 21 is a section through the cable which physically and electrically connects the transducer of the FIG. 1 system to the monitor (or SPCDU) of that system.

Referring still to the drawing, it was pointed out above that the cable 28 which connects transducer 24 to SPCDU 26 and the plug at the SPCDU end of that unit (identified by reference character 520 in FIGS. 1, 3, 22, 23, and 24) are also important features of the present invention. Cable 28, best shown in FIG. 21, includes an inner bundle 521 of insulated leads 522 which connect associated terminals 471 on the solder pads 429b and 429c of transducer ISA multipurpose board 349 (FIG. 29B) to associated terminals 524 (FIG. 29A) on a PCB (EEPROM/DEMUX board) 526 in plug 520. Leads 522 are surrounded by a Teflon (PTFE) or comparable insulation sleeve 527. The insulated cable bundle sleeve 527 and a bare ground lead 528 are surrounded by a conventional braided copper shield 529 which keeps the relatively high current flowing through the shield-surrounded leads from interfering with the current flow through a hereinafter described, outer bundle of leads also located in cable 28. Braided shield 529 is surrounded by a PTFE (polytetrafluorethylene) or comparable wrap 130. Copper shield 529 can slide freely relative to wrap 130. That keeps the copper shield from rubbing against and damaging the insulator jacket 527 surrounding inner cable bundle 521.

Located at intervals around PTFE wrap 530 are the insulated leads 522 of a second, outer bundle 532. These leads also connect cable-associated terminals 471 on solder pads 429b and 429c in transducer 24 to EEPROM/DEMUX board 526. Cable bundle 532 is enclosed in a second insulator jacket 534 of PTFE or a comparable material. Jacket 534 and a second bare ground 536 are surrounded by a second, outer, braided copper shield 537 to minimize, if not entirely eliminate, interference traceable to current flowing through the leads 522 in outer cable bundle 532. Braided shield 537 is surrounded by a paper wrap 540. This paper wrap allows the assembly of sleeve 537 and those cable components it surrounds to be easily slid into the outer, typically polyvinyl chloride jacket 541 of cable 28.

Another, and important, component of cable 28 is a load-bearing strand 542 fabricated from a high tensile strength, flexible, inextensible material such as Kevlar. Load-bearing strand 542 is located in the center, and extends the length, of cable 28. At its transducer 24 end, load-bearing strand 542 is immobilized by trapping it against a frustoconical boss 543 which extends into the detector unit housing compartment 86 of transducer housing 32 from the transducer casing outer end wall 544 with which the boss is integrated (see FIGS. 5 and 7).

Figure 7:
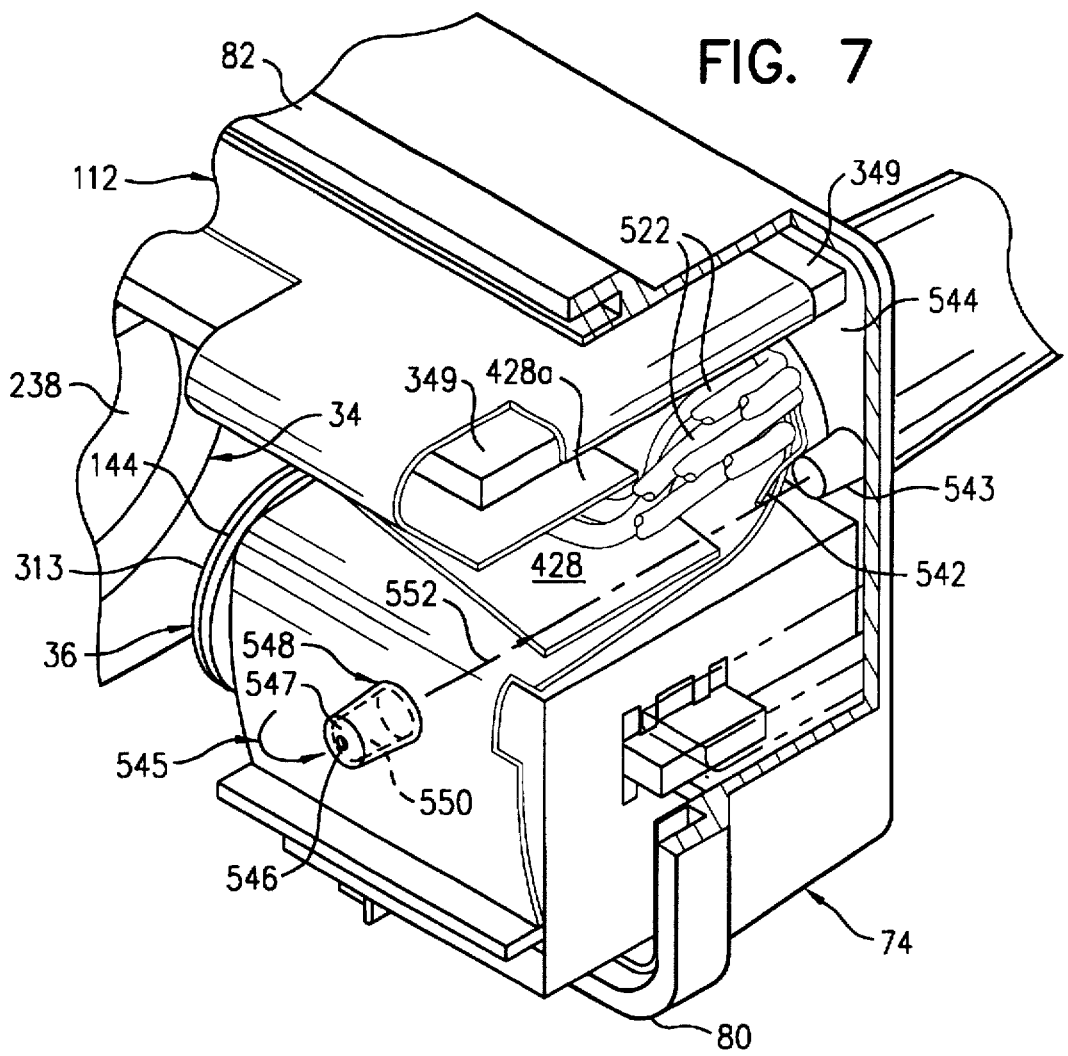
FIG. 7 is a partial view of the transducer with part of the casing broken away primarily to show how flexible connectors coupling an infrared radiation source unit and an infrared radiation detector to a printed circuit board of the ISA fit into the transducer casing.

As suggested by arrow 545 in FIG. 7, the anchoring of Kevlar strand 542 is accomplished by training the strand through an opening 546 in the end 547 of a hollow, cuplike retainer or cap 548 with an interior 550 configured to complement the configuration of boss 544 and then down through the interior of the retainer. Next, the retainer is installed on boss 543 by displacing it in the direction indicated by arrow 552 in FIG. 7. Friction retains cap 548 in place with load-absorbing strand 542 securely trapped and immobilized between the cap and boss 544.

Load-absorbing strand 542 is also anchored at the EEPROM/PCB end of cable 28, in this instance by training the strand through an opening 549 in EEPROM/DEMUX board 526 (see FIG. 24) and then knotting the free end of the strand to its standing part. With load-absorbing strand 542 thus anchored at both ends, axial loads imposed upon cable 28 are absorbed by this high-strength strand. This isolates those loads both from the conductors 522 and the other components of cable 28.

Figure 22:
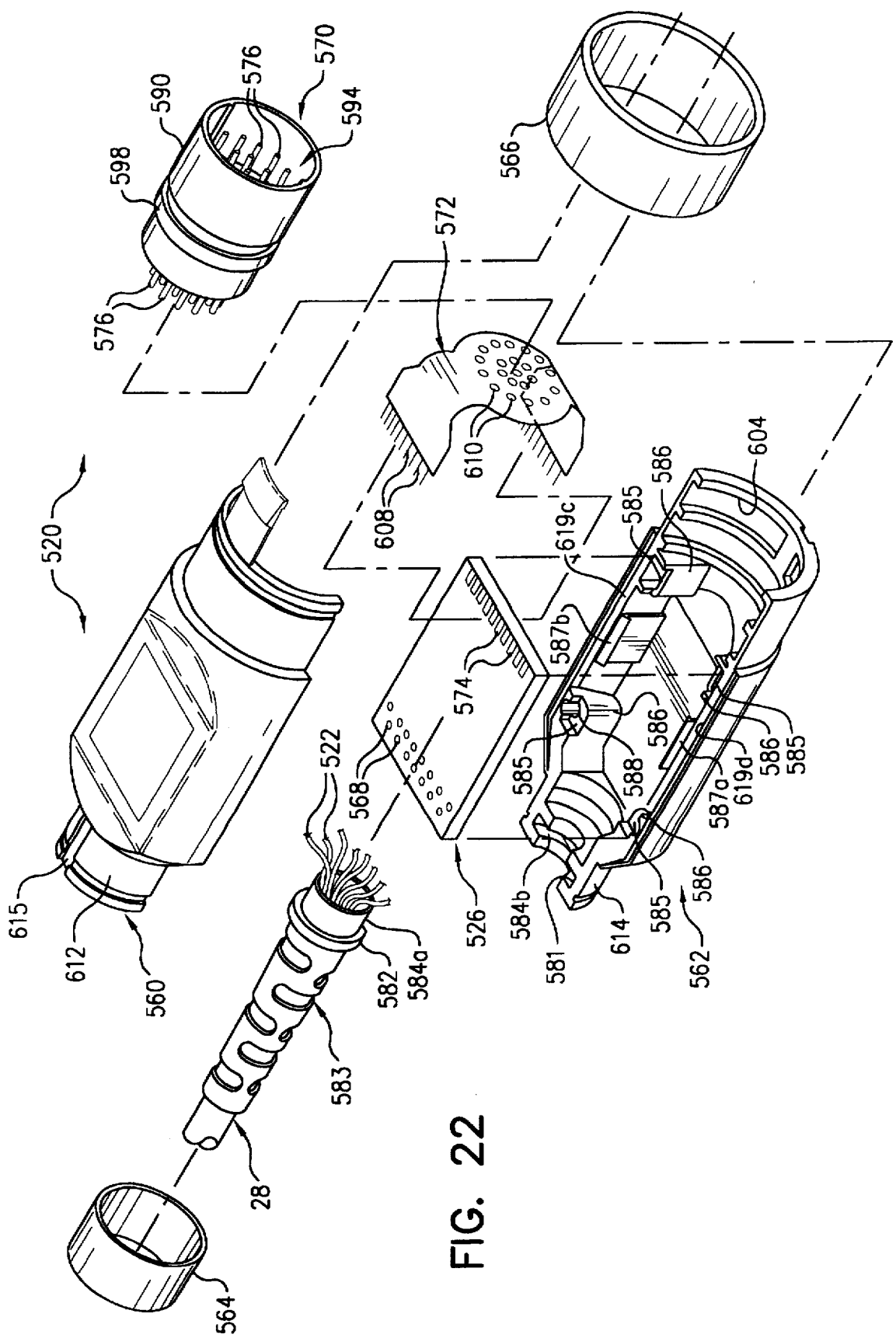
FIG. 22 is an exploded view of an active plug at the monitor end of the FIG. 1 cable.

Referring now to FIGS. 3 and 22–24 and most specifically to FIG. 22, the plug 520 at the SPCDU end of cable 28 includes a casing or housing 558 composed of two complementary casing components 560 and 562 and hoops or bands 564 and 566 for holding those casing components together. Housed in casing 558 are the EEPROM/DEMUX board 526 with its input terminals 568 for the leads 522, 529, and 536 in cable 28; a pin-type connector 570; and a flex connector 572 for connecting output terminals 574 on the top and bottom sides of PCB 526 to pins 576 of connector 570. As is shown in FIG. 22, the ends of the just-referred-to leads of cable 28 are soldered or otherwise electrically connected to terminals 568.

At the cable-associated end 578 of plug casing 558 is a circular groove defined by complementary semicircular recesses in casing components 560 and 562. One of these recesses is shown in FIG. 22 and identified by reference character 581. Trapped in this groove is a circular external boss 582 at the plug-associated end of a circumferentially slotted strain-relief fitting 583. That fitting, which is formed of a slotted, flexible polymeric material, surrounds cable 28. Complementary flat surfaces 584a and 584b on strain-relief fitting 583 and in recess 581 keep the fitting from rotating in plug 520. Thus, fitting 584 keeps cable 28 from rotating in plug casing 558. It also limits the bend radius of the cable at the plug-associated end of that component. This prevention of rotation and limiting of bend radius keeps potentially damaging stresses from being placed on the leads 522, 529, and 536 of the cable.

A second strain-relief fitting 584 of the same character as strain-relief fitting 583 is located at the transducer end of cable 28. Strain-relief fitting 584 keeps the cable from rotating relative to the transducer and from bending too sharply relative to that system component.

Turning next to FIGS. 22 and 24, plug casing component 562 has shelves 585 located at the upper ends of component-integral bosses 586 found at locations corresponding to the four corners of PCB 526. Plug casing component 560 has complementary shelves (not shown). In the assembled plug (see FIG. 23), PCB 526 is located between integral, internal spring tabs 587a and 587b. The PCB is trapped between (and held in place by) the shelves 585 in casing component 560 and 562. The vertical ledge structures of the casing components bounding those shelves (of which 588 is representative) keep the PCB from shifting longitudinally or laterally in casing 558.

As is shown in FIGS. 22 and 23, the male connector 570 of plug 520 has a cylindrical casing component 590 housing pins 576 which, on the output side 592 of the connector, plug into complementary female connectors (not shown) in SPCDU 26. That connects the SPCDU through PCB 526 and cable 28 to transducer 24. Pins 576 are typically molded into casing 590.

Male connector 570 is secured in cable housing 558 by trapping a circumferential boss 598 on connector housing 590 in a complementary, circular groove 600 in the plug casing. This groove is composed of complementary, mating, semicircular, internal recesses in plug casing components 560 and 562 at the SPCDU end 601 of plug 520. These recesses are best shown in FIG. 23 in which they are identified by reference characters 602 and 604. This boss-and-groove arrangement provides axial and rotational restraint between plug 520 and cable 28.

The initial step in assembling plug 520 is to connect the leads 522, 529, and 536 in cable 28 to the input terminals 568 on EEPROM/DEMUX board 526. Typically, the next step is to assemble pin-type male connector 570 to flex connector 572 with pins 576 extending through female connectors 610 in the flex connector and thereby electrically connecting leads 608 to those pins. Then, the leads 608 of flex connector 572 are joined to the output terminals 574 on the top and bottom of that PCB. This innovative assembly technique is faster and more cost effective than making conventional soldered or crimped connections to individual leads.

The assembly of PCB, flex connector, male connector, and cable is then installed in upper cable casing component 560 with the integral internal spring tabs 587a and 587b in casing component 560 engaging opposite sides of PCB 526 to temporarily hold the PCB in place. The load-absorbing Kevlar strand 542 of cable 28 is anchored to PCB 526 by threading the strand through a hole 611 in the PCB and then tying a knot between the standing and free segments of the strand (see FIG. 23).

Next, plug casing component 562 is put in place, and the two casing components 560 and 562 are fastened together with the internal plug components clamped therebetween by retainer hoops 564 and 566. In particular, casing components 560 and 562 have complementary, matching, semicircular bosses 612 and 614 at the cable end 578 of plug casing 558. Hoop 564 is slid over these bosses to clamp them—and therefore casing components 560 and 562—together at the cable end 578 of the casing. A bump (not shown) in hoop 564 slides into a groove 615 in casing component 562 as the hoop is installed. This arrangement provides rotational restraint between the hoop and the casing 558 of plug 520.

Similar, complementary, semicircular bosses 616 and 618 are formed at the SPCDU end 601 of plug casing 558. As is also shown in FIG. 23, hoop 566 clamps these bosses—and therefore casing components 560 and 562—together at the SPCDU end 601 of plug 520.

With the plug casing components 560 and 562 assembled together, ridges (not shown) on opposite sides of component 560 fit into complementary recesses 619c and 619d on the opposite sides of casing component 562. This interfitting, quasi tongue-and-groove arrangement provides ESD protection for the electrical components on EEPROM/DEMUX board 526.

Located at the SPCDU end 601 of plug 520 is a tang 620 which is integral with upper casing component 560, extends beyond the SPCDU-associated end 601 of casing 558, and is resiliently displaceable in the arrow 621 direction. Toward the free end of tang 620 is a latch 622 which is engaged by a complementary, SPCDU-incorporated keeper (not shown) when plug 520 is plugged in to the SPCDU and the tang flexes to slide by the SPCDU keeper and then restores to its FIG. 22 configuration. Tang 620 orients the pins 576 with the corresponding female connectors in the SPCDU socket (not shown), and latch 622 ensures that plug 520 is not inadvertently displaced from the SPCDU socket.

The calibration verification unit 30 discussed briefly above and employed to verify the calibration of transducer 24 is shown in FIGS. 1 and 3 and in more detail in FIGS. 18, 19A, 19B, 20A, and 20B. That unit includes a hollow housing 628 composed of two mated casing components 630 and 632 bonded together without the need for fasteners as by an appropriate adhesive. Source side casing component 630 is made from interlocking casing elements 634 and 636 while detector side casing component 632 is similarly fabricated from interlocking casing elements 638 and 640.

As is shown in FIG. 19B, element 634 has a peripheral wall structure 642 bounding a cavity 644, and casing element 636 has a peripheral wall structure 645 bounding a cavity 646. Complementary cavities 648 and 650 in casing components 638 and 640 (see FIG. 19A) are bounded by the integral wall structures 652 and 654 of those casing components. Complementary dovetail joint elements 641a and 641b (FIG. 18) lock the casing elements 634/636 and 638/640 together.

Figure 18:
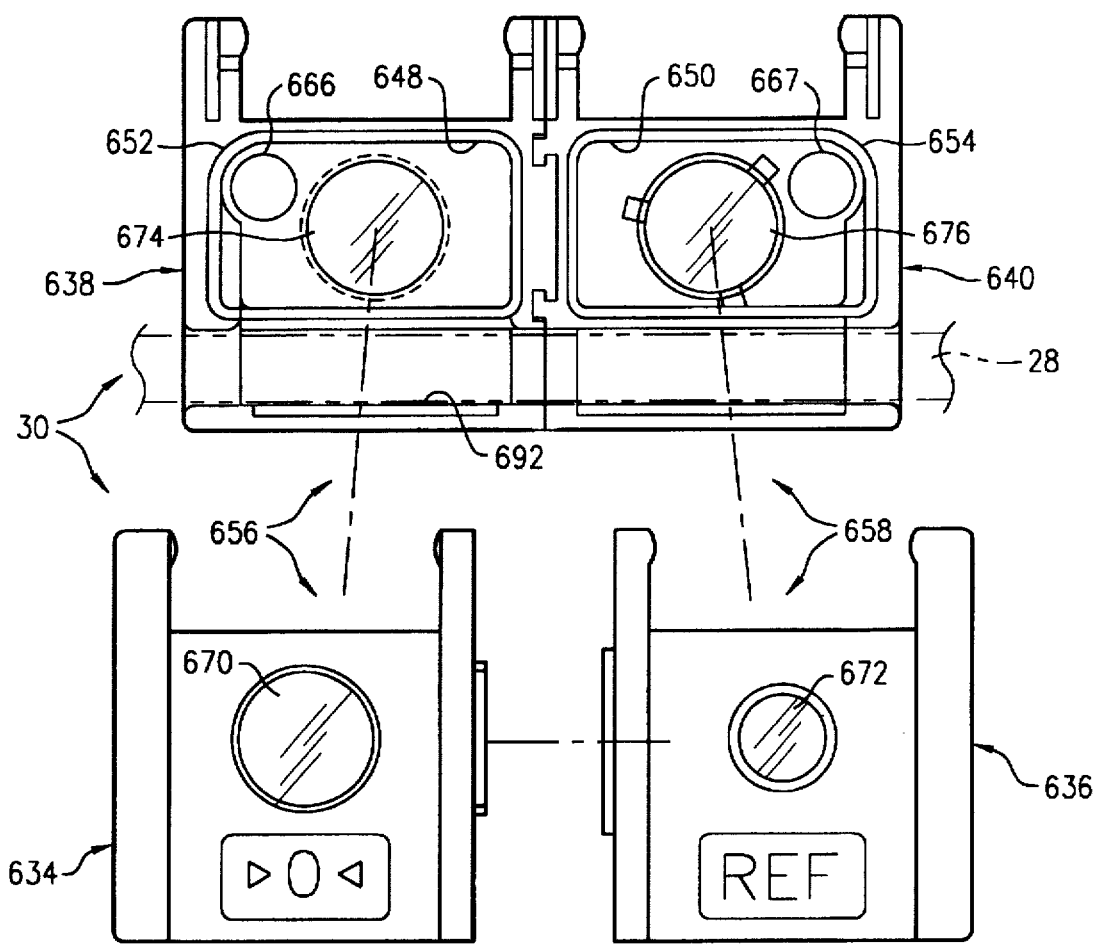
FIG. 18 is an exploded view of a passive unit which may be mounted on the active connector component of the FIG. 1 system and which is employed to verify the calibration of the transducer.
Figure 20A:
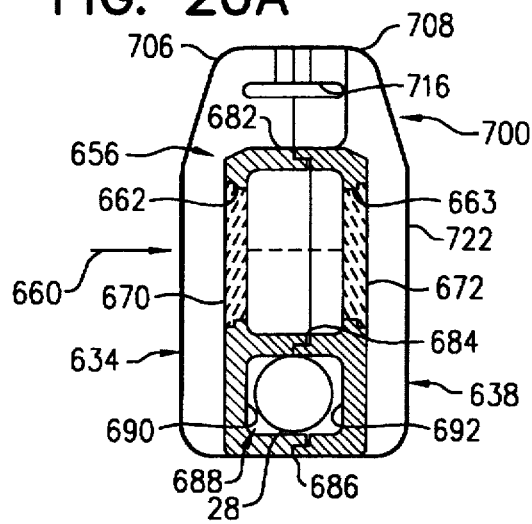
FIG. 20A is a section through a zero cell which is a component of the passive calibration verifier.
Figure 20B:
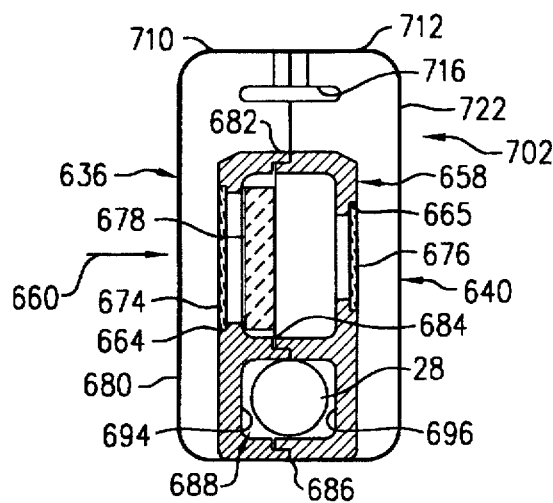
FIG. 20B is a section through a reference cell which is a component of the passive calibration verifier.

With the two casing components 630 and 632 assembled as shown in FIGS. 1, 3, 20A, and 20B, matching cavities 644 and 648 define a zero cell 656 (see FIGS. 18 and 20A) while mating cavities 646 and 650 define a reference (or REF) cell 658 (see FIGS. 18 and 20B). Zero cell 656 and reference cell 658 are employed as described above and in more detail below in verifying the calibration of transducer 24. In different steps of the calibration routine, infrared radiation propagated along optical path 56 traverses zero and reference cells 656 and 658 as indicated by arrow 660 in FIGS. 20A and 20B.

Cells 656 and 658 are preferably color coded to assist a user in aligning transducer 24 with that cell employed in a particular step of the calibration verification process. To this end, the casing elements 634 and 638 defining zero cell 656 may have a dark color and the casing elements 636 and 640 defining reference cell 658 a lighter color.

In different steps of the calibration verification process, the beam 132 of infrared radiation emitted from the infrared radiation source 34 in transducer 24 is passed through zero cell 656 and through reference cell 658 as indicated above. To this end, aligned, infrared radiation passing apertures 662 and 664 are provided in the casing elements 634 and 638 defining the zero cell, and similarly aligned apertures 666 and 668 are provided in the two casing elements 636 and 640 defining reference cell 658. The interiors of the zero and reference cells are isolated from the ambient surroundings by windows 670, 672, 674, and 676 respectively installed in apertures 662, 663, 664, and 665 to keep foreign material and gases (especially carbon dioxide in the ambient surroundings) from the zero and reference cell interiors. These four windows may also be fabricated from sapphire or an alternative radiation-transmitting material; and reference cell window 676 can be made smaller than window 674 with a consequent cost savings because of the focusing of infrared radiation beam 132 by source unit mirror 140.

As is shown in FIG. 20B, an optical filter 678 is mounted in reference cell 658 behind the window 674 on the source side 680 of the calibration verification unit 30. This filter is employed to emulate a specific concentration of the carbon dioxide or other gas being monitored by attenuating the beam 132 of infrared radiation passing through reference cell 658 to the same extent that the same concentration of the gas in a sample flowing through passage 47 of airway adapter 22 would.

Permanent magnets 666 and 667 (see FIG. 18) are housed in the casing 650 of calibration verification device 30 adjacent zero cell 656 and reference cell 658, respectively. Magnet 666 closes a "zero" reed switch 668 (FIG. 27) on heater board 337 in transducer 24 when the transducer is assembled on zero cell 656; and magnet 667 closes a second, "reference" or "span" reed switch 669 on that board when the transducer is on reference cell 658 of calibration verification unit 30. Switches 668 and 669 identify the cell on which the transducer is placed (zero or reference) in the transducer verification process described hereinafter.

Referring now primarily to FIGS. 20A and 20B, the two components 630 and 632 of calibration verification unit casing 628 are bonded together to keep carbon dioxide and other foreign material from zero cell 656 and reference cell 658. Sealing of the gaps between the two casing components is promoted by employing dovetail joints therebetween as shown by reference characters 682, 684, and 686 (see FIGS. 20A and 20B). These dovetail joints extend completely around the zero and reference cells 656 and 658 and from end-to-end of casing 628 at the bottom of that casing.

Referring still to FIGS. 20A and 20B and also to FIGS. 1, 3, and 18, it was pointed out above that calibration verification unit 30 is mounted on and can be slid along the cable 28 connecting transducer 24 to SPCDU 26. Cable 28 extends through a passage 688 in the casing 628 of the calibration verification unit. That passage extends from end-to-end of the casing and is defined by mating, semicircular recesses 690 and 692 in casing elements 634 and 638 and by similarly configured, complementary recesses 694 and 696 in casing elements 636 and 640.

As discussed above, this novel technique of mounting the calibration verification unit is possible because that unit is passive and accordingly has no electrical connections to other system components and is advantageous in that calibration verifier 30 can be located along cable 28 at a position in which transducer 24 can easily be assembled to it for calibration verification purposes as is shown in FIG. 3.

FIG. 3 also shows the relationship between transducer 24 and calibration verification unit 30 with the transducer installed on reference cell 658 of the calibration verification unit. The transducer 24 is similarly related to the calibration verification unit when it is coupled to that unit on zero cell 656. In both cases, the cell being employed fits into the gap 66 between the infrared radiation source end and detector end sections 62 and 64 of transducer housing 32 with the windows 670 and 672 or 674 and 676 of the active cell aligned with the optical path 56 of the transducer.

Transducer 24 is directed onto calibration verification unit 30 in alignment with the selected cell 656 or 658 by guides 698 and 700 at opposite ends of zero cell 656 and by guides 702 and 704 at the opposite ends of reference cell 658. Guides 698, 700, 702, and 704 are provided by complementary guide segments on the four elements 634, 636, 638, and 640 of calibration verification unit casing 628. The guide elements making up representative guide 700 are shown in FIG. 20A and identified by reference characters 706 and 708. The elements making up likewise representative reference cell guide 702 are shown in FIG. 20B and identified by reference characters 710 and 712.

Lugs 714 (see FIGS. 2 and 3) are formed on the side walls 76 and 80 of transducer housing 32 adjacent the inner end 715 of the gap 66 between the two end sections 62 and 64 of that casing. A representative one of those lugs is shown in FIG. 3. Complementary recesses 716 are provided in the four zero and reference cell guides 698 ... 704 of calibration verification unit 30. When transducer 24 is coupled to the calibration verification unit on zero cell 656 or on reference cell 658, the transducer casing-associated lugs 714 snap into the slots 716 in those pair of guides 698/700 or 702/704 between which the transducer is guided. This locks the transducer to the calibration verification unit with the proper alignment therebetween.

One of the guides in each pair (698 and 702) has a trapezoidal configuration, and the other guide in the pair (700 or 704) has a rectangular configuration. The guides (698 and 700 or 702 and 704) slide into slots or grooves 718 and 720 of complementary configuration (see FIGS. 2 and 3) when transducer 24 and calibration verifier 30 are coupled together. This asymmetric guide and groove arrangement ensures that the two components are correctly assembled with the source side 680 of calibration verification unit 30 facing the infrared radiation source unit 34 of transducer 24 and the detector side 722 of the verifier facing the detector unit 34 of the calibration verification unit.

A similar arrangement (see FIG. 1) ensures that transducer 24 and airway adapter 22 are assembled with the correct orientation between those components (see FIG. 2). To this end, airway adapter 22 is provided with guides 724 and 726 corresponding to guides 698 and 700 (or 702 and 704) in that they are spaced to engage opposite sides of transducer casing 32 and respectively have a trapezoidal configuration and a rectangular configuration. These guides also have slots 728 and 730 into which transducer casing lugs 714 can snap to lock the airway adapter and transducer together.

One of the significant features of the present invention, discussed briefly above, is the multiplexing of the different signals outputted from transducer 24 when: (a) the zero and span switches 668 and 669 on multipurpose board 349 are both open, and (b) first the zero switch 668 and then the span switch 669 are closed in different steps of the transducer calibration verification process. This multiplexing has the advantage of reducing the number of leads 622 in cable 28 because only one lead is required to conduct the several different signals through the cable. A lighter and less expensive cable can therefore be employed.

The just-described signals are utilized to indicate whether transducer 24 is coupled to one of the calibration verification device cells and, if it is, which one. The signals are voltage coded as follows:

| Zero Switch 668 | Span Switch 669 | Voltage |
| --- | --- | --- |
| Open | Open | 4 |
| Closed | Open | 0 |
| Open | Closed | 8 |

The circuitry for multiplexing the signals so that they can be transmitted on a single lead 522 is shown in FIG. 27 and identified by reference character 734. In addition to the zero and reference cell reed switches, circuit 734 has a 16.5 Kohm resistor 736 and a 49.9 Kohm resistor 738. The voltage coded output signals are available on the lead identified by reference character 522-1 in FIG. 27 to distinguish that lead from the other insulated leads 522 in cable 28. At the plug 520 end of cable 28, the signal on lead 522-1 is routed to a 24.9 Kohm resistor 740 on the printed circuit board 526 in plug 28.

With zero switch 668 and span switch 669 both open, a +12V terminal 742 on transducer multipurpose board 349 is connected through resistor 738 to lead 522-1, and a 4V signal appears at the output side of resistor 740 on lead 744. With zero switch 668 open and span switch 669 closed, +12V terminal 742 is connected through resistor 736 to lead 522-1; and the voltage level on the output side lead 744 of resistor 740 is 8 volts. And, with zero switch 668 closed and span switch 669 open, +12V terminal 742 is connected through resistor 738 to ground; and the voltage on resistor 740 output lead 744 is zero volts.

Figure 28:
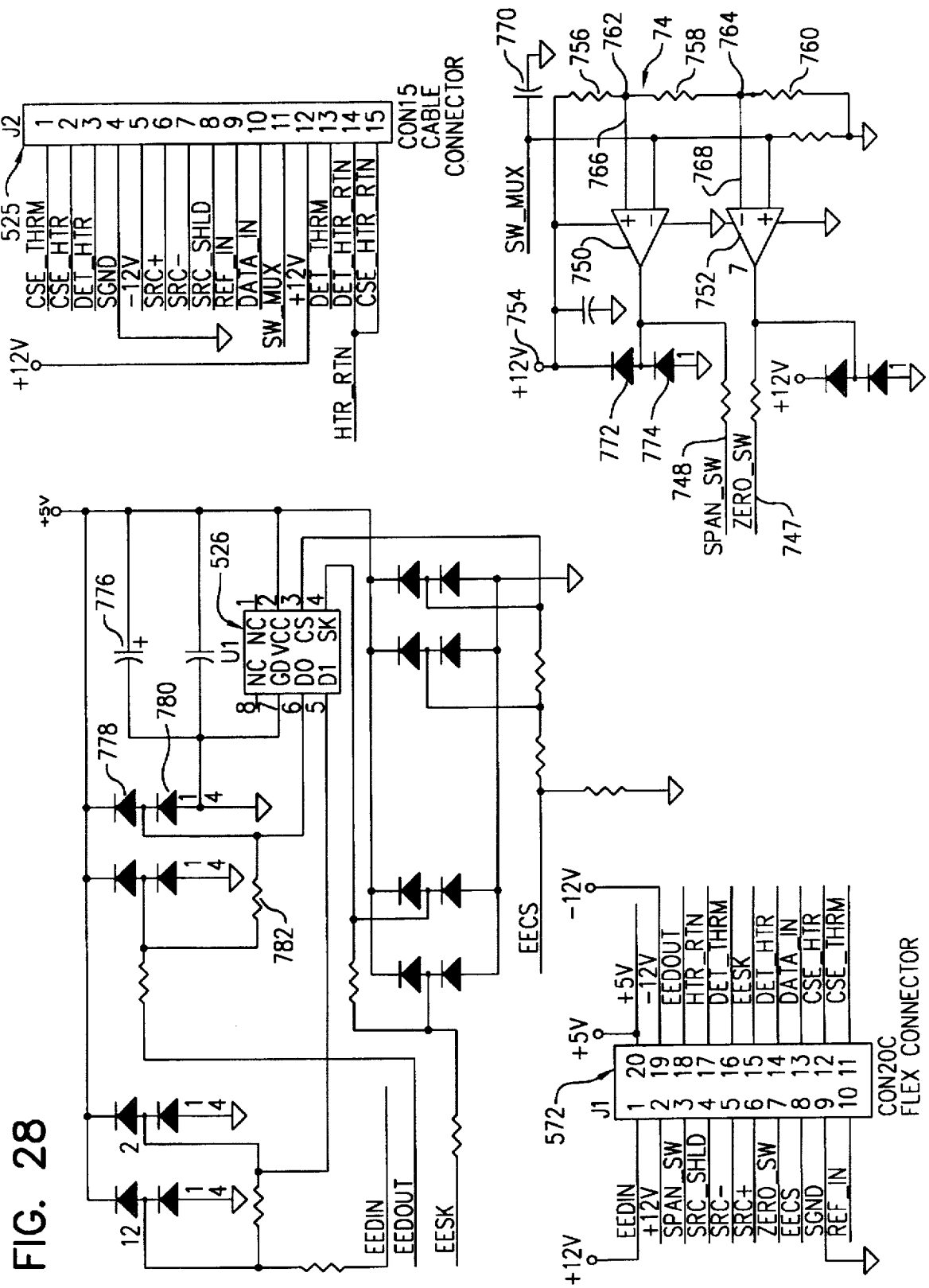
FIG. 28 is a schematic of the electrical circuits in the FIG. 22 plug.

The signal carried by lead 744 is decoded by the demux (or demultiplex) circuit 746 illustrated in FIG. 28. That circuit is located on the PCB 526 in plug 520. If the decoded signal is between zero and 2.5 volts, a signal indicating that zero switch 668 is closed appears on output lead 747 of demux circuit 746; and, if span switch 669 is instead closed, a signal will appear on demux circuit output lead 748. If both switches are open, there is no signal on either output lead.

The incoming signal is decoded in demux circuit 746 by two comparators 750 and 752 so connected to +12V terminal 754 on PCB 526 that comparator 748 has a positive input and comparator 750 has a negative input. Demux circuit 746 also has a string of three voltage-dividing resistors 756, 758, and 760 connected in series between +12V terminal 752 and ground with a junction 762 between resistors 756 and 758 and a second junction 764 between resistors 758 and 760. A lead 766 connects terminal 762 to the positive input of comparator 750, and a lead 768 connects junction 764 to the negative input of inversely connected comparator 752.

Comparator 750 is configured to turn on when a signal of at least 6 volts appears on lead 766, and comparator 752 is configured to turn on when the voltage appearing on lead 768 is between zero and 2.5 volts. With span switch 669 closed, a 5.8V signal appears on lead 766, and comparator 750 turns on with a signal consequently appearing on lead 748 to indicate that the transducer 24 has been placed on span cell 658. If transducer 24 is instead placed on zero cell 656, a 2.18 volt signal appears on lead 768; and comparator 752 instead turns on with a signal consequently appearing on lead 747 to indicate that the transducer is located on the zero cell. If transducer 24 is not located on a calibration verification device cell, voltage levels which will turn on comparators 750 and 752 are not available at voltage divider network terminals 762 and 764; and there is no output signal from demux circuit 746.

In addition to the components discussed above, demux circuit 746 includes a variety of capacitors and diodes with the capacitor labeled 770 and the diodes 772 and 774 on the output side of comparator 750 being typical. These circuit components provide R-C filtering and ESD protection for the demux circuit. Similarly wired capacitors, diodes, and resistors of which the capacitor labeled 776, the diodes labeled 778 and 780, and the resistor labeled 782 are typical provide ESD protection for EEPROM 526.

The steps performed by the gas analyzer microprocessor in the course of verifying the calibration of a transducer 24 can best be understood by referring to FIGS. 3 and 30A–E.

The MAIN CALIBRATION program or protocol begins at steps 100 (FIG. 30A). At step 102, the operator must choose among: (a) operating soft key switches, (b) detecting airway conditions, and (c) performing calibration. If the operator chooses to operate soft key switches or detect airway conditions, the processing proceeds to steps S104 and S106, respectively. The soft key switch and detect airway condition routines of steps S104 and S106 are not in themselves part of the present invention and will not be discussed herein.

If the operator chooses calibration at step S102, the process moves to step S108; and the operator must choose between: (a) performing a new calibration and (b) checking a previous calibration. If the operator chooses to check a previous calibration, the process goes to the CHECK CALIBRATION routine of step S200 (see FIG. 30B).

If the operator chooses to perform a new calibration, the process moves to step S112. At step S112, the operator is prompted to choose among the following: (a) airway calibration, (b) sensor calibration, and (c) exiting the calibration process and running a gas analyzing routine.

If the operator chooses airway calibration, the process moves to the AIRWAY CALIBRATION routine in step S114. That routine is not in itself part of the present invention and will not be discussed further herein.

If the operator chooses sensor calibration at step S112, the process moves to step S118; and the operator is presented with a CALIBRATION TYPE menu. The CALIBRATION TYPE menu presents the operator with the following choices: (a) calibrator calibration and (b) gas calibration.

Figure 30B:
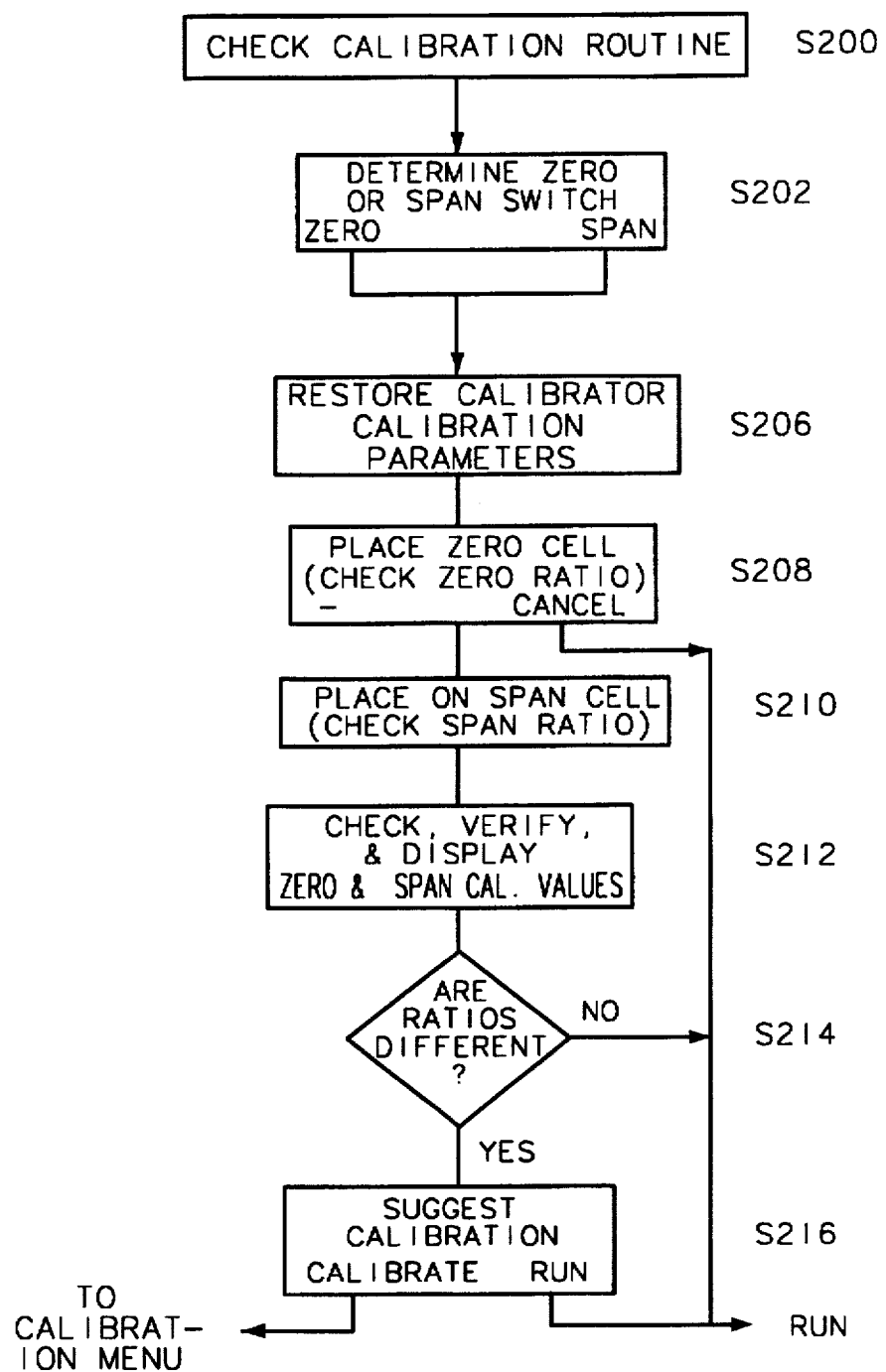
FIG. 30B is a flow chart of a CHECK CALIBRATION ROUTINE called from the MAIN CALIBRATION ROUTINE.
Figure 30C:
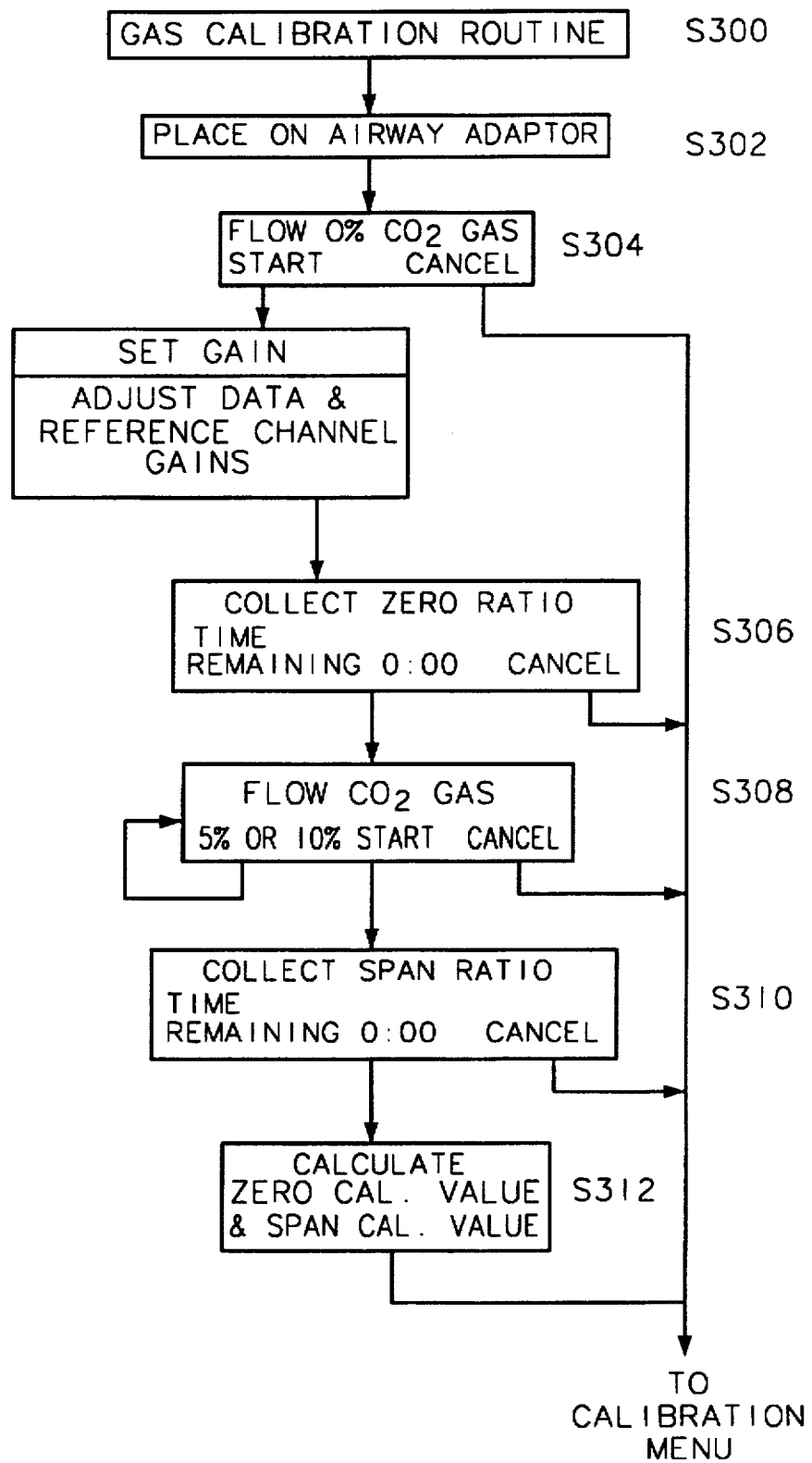
FIG. 30C is a flow chart of a GAS CALIBRATION ROUTINE called from the MAIN CALIBRATION ROUTINE.
Figure 30D:
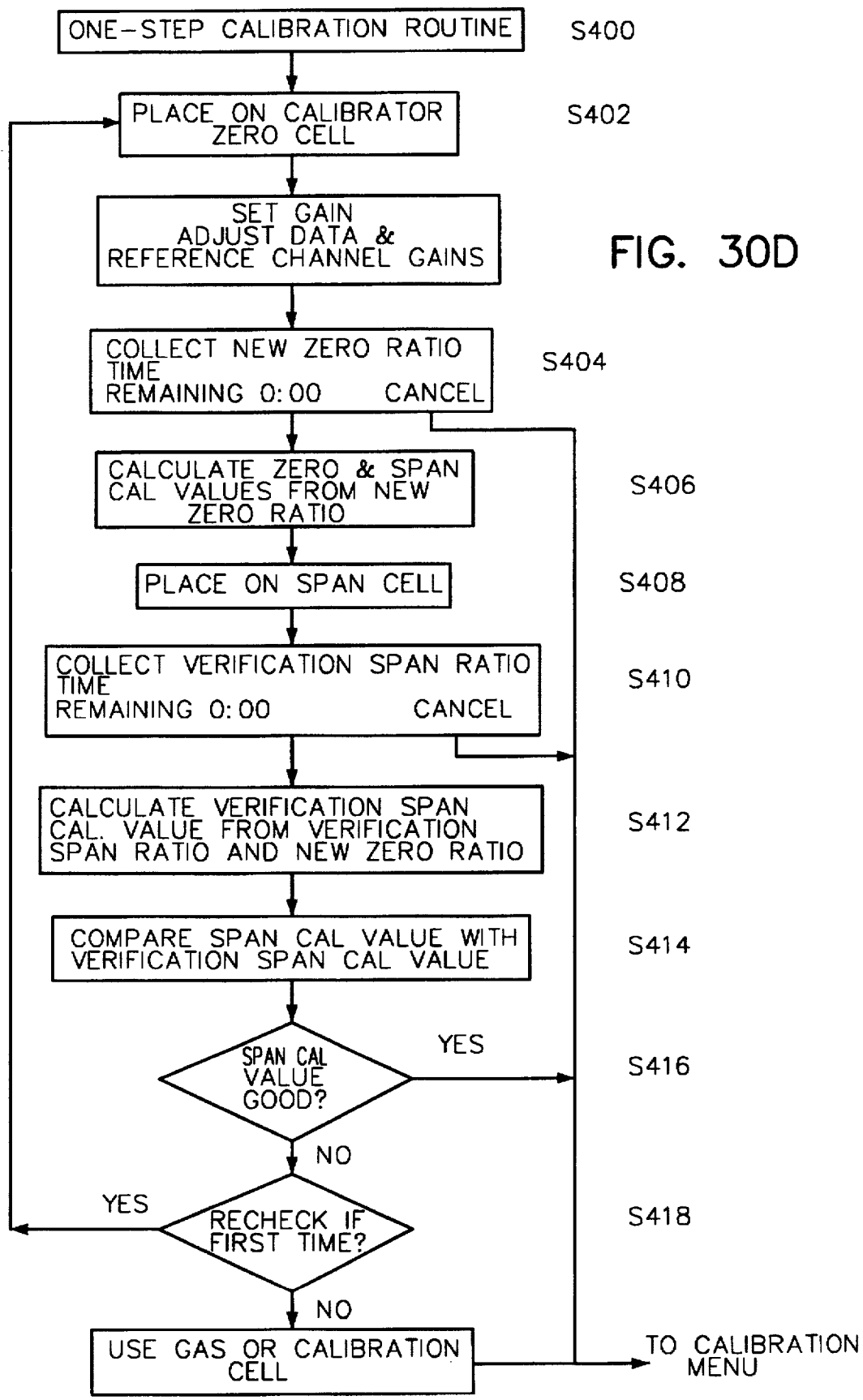
FIG. 30D is a flow chart of a ONE-STEP CALIBRATION ROUTINE for implementing the principles of the calibration verification protocol.

If the operator chooses gas calibration at step S118, the process moves to the GAS CALIBRATION routine of step S300 (see FIG. 30C).

On the other hand, if the operator chooses calibrator calibration, the process moves to step S120 where the operator must choose between: (a) one-step calibration and (b) cell calibration. If the operator chooses one-step calibration, the process moves to the ONE-STEP CALIBRATION routine of step S400 (see FIG. 30D). If the operator chooses cell calibration, the CELL CALIBRATION routine is performed at step S500 (see FIG. 30E).

The relevant routines called by the MAIN CALIBRATION program are explained in detail below with reference to the appropriate figures of the drawing.

The CHECK CALIBRATION routine begins at step S200 as shown in FIG. 30B. At step S202, the microprocessor determines whether zero cell 656 or reference cell 658 of calibration verifier 30 has been placed in the transducer optical path 56. If the ZEROSW signal appears, zero cell 656 has been placed in the optical path; and, if the SPANSW signal appears, the reference cell 658 has been placed in the transducer optical path.

After determining which cell is in optical path 56, step S200 asks the operator if an adult airway adapter is being used. If it is, the processing goes directly to step S208. If an adult airway adapter is not being used, the processing goes first to step S206 where the parameters for the adult airway adapter are restored for calibration.

The processing then goes to step S208, which instructs the operator to place zero cell 656 in transducer optical path 56 if this has not already been done; and a Zero Ratio is determined in the manner described above. The operator has the option of cancelling the calibration check at step S208. Otherwise, the process advances to step S210.

The operator is instructed at step S210 to place the transducer 24 on reference cell 658, at which time the Span Ratio is measured. At step S212, the zero and span ratios are displayed; and, at step S214, the zero and span ratios calculated at steps S208 and S210 are compared with the Zero Ratio and Span Ratio calculated during the last calibration of the transducer 24 being subjected to calibration verification. If the ratios calculated in steps S208 and steps S210 are different, i.e., greater than or less than the previously calculated ratios by a predetermined amount, the processing moves to step S216 where the operator is prompted to recalibrate.

On the other hand, if the ratios are not significantly different; i.e., within a predetermined value above or below the previously calculated ratios, the processing continues with normal measurement of gas concentration. At the next step, S216, the operator also has the discretion to continue normal analysis of gas without further calibration.

If at step S216 the operator chooses to rezero the transducer 24, the processing goes to step S112 where the operator is presented with the calibration menu.

Referring now to FIG. 30C, the GAS CALIBRATION routine is carried out at the factory. That routine begins at step S300. Step S302 prompts the operator to assemble transducer 24 to an airway adapter 22.

At step S304, the operator is prompted to start gas with no carbon dioxide flowing through airway adapter 22. The operator then enters "start" to proceed with the gas calibration procedure or "cancel" to exit the gas calibration procedure and return to the calibration menu.

If the operator chooses "start", the Zero Ratio is obtained at step S306. More specifically, a clock is set to a predetermined measurement period and then counted down to zero. During the measurement period, multiple ratios of the data detector 270 output signal magnitude to the reference detector 272 output signal magnitude are measured. The average of these ratios is subsequently employed as the Zero Ratio.

The operator may cancel GAS CALIBRATION and return to the calibration menu at any point during the measurement period.

At step S308, the operator is prompted to start flowing a gas mixture containing five (or 7.5 or 10) percent carbon dioxide through airway adapter 22.

When the operator enters "start" at step S308, the process moves to step S310 where a clock is again set to a measurement value and counted down to zero. Plural ratios of the data detector 270 output to the reference detector 272 output are taken during the countdown of the clock. The average of these ratios is used as the Span Ratio. Again, the operator has the option to cancel GAS CALIBRATION and return to the calibration menu during the measurement period of step S310.

When the clock reaches zero at step S310, the process moves to step S312, where the Zero Cal Factor and Span Cal Factor are calculated from the Zero Ratio and Span Ratio according to equations (6) and (7). The process then returns to the calibration menu.

The ONE-STEP CALIBRATION routine (calibration verification) may be performed in the field. That routine begins at step 400 (see FIG. 30D). At step S402, the operator is prompted to place transducer 24 on the zero cell 656 of calibration verification unit 30. At step S404, a clock is set to a predetermined measurement value and counted down to zero. While the clock is counting down, ratios of the data and reference detector output signals are calculated at different points in time. The average is a New Zero Ratio. The operator has the option to cancel ONE-STEP CALIBRATION during step S404 and return to the calibration menu.

After the clock counts down to zero, the process advances to step S406. At step S406, the Zero and Span Cal Values are calculated according to equations (6) and (7) from: (a) the New Zero Ratio collected at step S404, and (b) the New Span Ratio calculated from the Concentration Factor stored in the EEPROM 526 in plug 520 and the New Zero Ratio according to equations (10) or (11).

The operator is next prompted to place transducer 24 on reference cell 658 of calibration verification device 30 (step S408).

The process then advances to step S410, at which point the clock is again set to a measurement value. The clock is then counted down to zero, and the ratios of data and reference detector output signals are generated at different points. The operator has the option to cancel ONE-STEP CALIBRATION during step S408 and return to the calibration menu.

After the clock counts down to zero, the average of the ratios calculated during the measurement period is taken. A verification of Span Ratio is the average of these ratios.

A verification Span Cal Value is calculated at step S412 from the verification Span Ratio collected at step S410 and the New Zero Ratio collected at step S404 according to equation (7).

At step S414, the Span Cal Value calculated at step S406 is compared with the verification Span Cal Value generated at step S412 from the New Zero and Measured Span Ratios. If the Span Cal Value calculated at step S406 is within a sufficiently small range of the verification Span Cal Value calculated at step S412: (a) the Span Cal Value calculated at step S406 is determined to be good at step S416; and (b) the process exits ONE-STEP CALIBRATION to the calibration menu.

If, on the other hand, the Span Cal Value calculated at step S406 is not within a sufficiently small range of the Verification Span Value calculated at step S402: (a) the Span Cal Value calculated at S406 is determined not to be good, and (b) the process proceeds to step S418.

If the Span Cal Value calculated at step S404 has been determined not to be good for the first time at step S418, the operator is given the opportunity at step S418 to recalculate the Zero and Span Cal Values by returning to step S402. The operator may also elect to return to the calibration menu without repeating the ONE-STEP CALIBRATION routine.

Figure 30E:
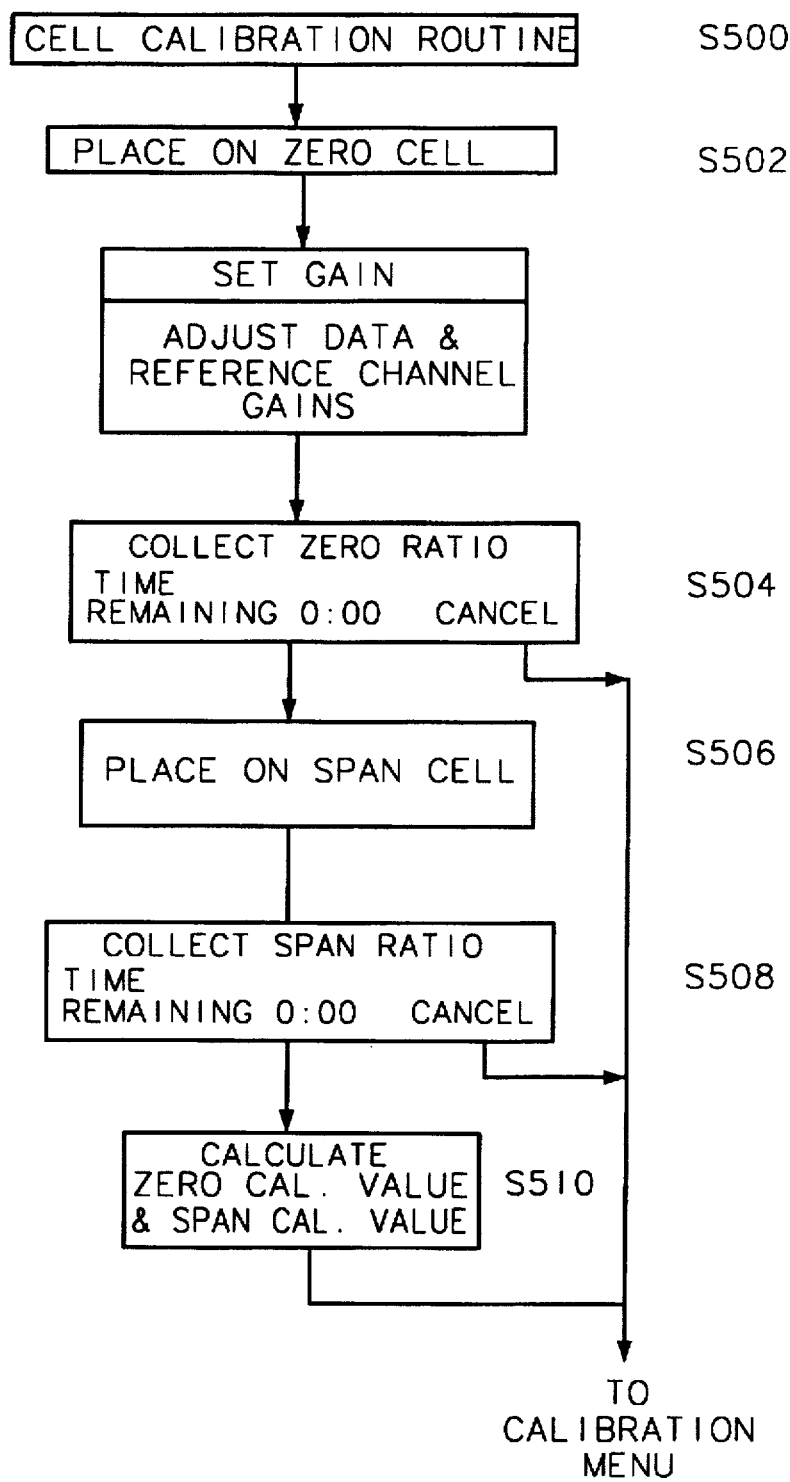
FIG. 30E is a flow chart depicting a CELL CALIBRATION ROUTINE of the calibration verification protocol.

CELL CALIBRATION begins at step S500 (see FIG. 30E). At step S502, the operator is prompted to place transducer 24 on the zero cell 656 of calibration verification unit 30. The process then proceeds to step S504 where a clock is set to a measurement value and then counted down to zero. While the clock is counting down to zero, the operator may choose to cancel CELL CALIBRATION and return to the calibration menu.

Ratios of the data and reference detector 270 and 272 output signals are generated at different points in time during the countdown of the clock. The Zero Ratio is the average of the different ratios and is calculated after the clock reaches zero.

The process then proceeds to step S506, and the operator is prompted to place transducer 24 on reference cell 658 of unit 30. The process then proceeds to step S508 at which point the clock is again set and begins counting down. The operator is given the opportunity to cancel CELL CALIBRATION at step S508 and return to the calibration menu at step S112.

When the clock reaches zero, the Span Ratio is calculated. It is the average of ratios of the data and reference detector output signals taken while the clock is counting down to zero.

If the operator does not choose to cancel the cell calibration routine at step 508, the routine proceeds to step S510. In this step, the Zero Cal Factor and Span Cal Factor are calculated from the Zero Ratio and the Span Ratio according to equations (6) and (7).

The principles of the present invention have above in the interest of brevity and clarity been developed principally with reference to the use of that invention to monitor the end tidal carbon dioxide of a medical patient. This application, while important, is only exemplary. Devices, systems, and routines employing the principles of the present invention may be advantageously used to monitor the concentration of virtually any polyatomic, asymmetric compound in a sample which may contain that compound; for example, carbon dioxide and carbon monoxide, water, nitrogen oxides, ammonia, fluorocarbons, etc., it being necessary only to select appropriate bandpass filters and an appropriate path length through the sample being monitored to adapt the invention to the measurement of the concentration of a given molecule. The invention may be used in industrial and other settings as well as in medical applications other than end tidal carbon dioxide measurement. Therefore, the approach of describing the invention with reference to a particular application of the invention is not intended to in any way limit the scope of the appended claims.

The invention may accordingly be embodied in many forms without departing from the spirit or essential characteristics of the invention. The present embodiment is therefore to be considered in all respects as illustrative and not restrictive. The scope of the invention is indicated by the appended claims rather than by the foregoing description, and all changes which come within the meaning and range of equivalency of the claims are therefore intended to be embraced therein.

What is claimed is:

1. A method of assembling a transducer which comprises: (a) complementary first and second open-sided housing components, and (b) an integrated assembly comprising an infrared radiation emitter unit, an infrared radiation detector unit, and a printed circuit board, said method comprising the steps of:

installing said integrated assembly in said first housing component with said emitter unit in a first compartment-defining element in the first housing component and the detector unit in a second compartment-defining element in said first housing component;

thereafter fixing said second housing component to said first housing component with said emitter unit and said detector unit also in part housed in complementary, first and second, compartment-defining elements in said second housing component;

providing a means for heating an airway adapter assembled to said transducer;

assembling said heating means to said printed circuit board; and installing said heating means concurrently with said integrated assembly and in a passage defined by the first and second transducer housing components and located between infrared unit-receiving and detector unit-receiving compartments bounded by the compartment-defining elements of said components.

2. A method of assembling a transducer which comprises: (a) complementary first and second open-sided housing components, and (b) an integrated assembly comprising an infrared radiation emitter unit and an infrared radiation detector unit, said method comprising the steps of:

installing said integrated assembly in said first housing component with said emitter unit in a first compartment-defining element in the first housing component and the detector unit in a second compartment-defining element in said first housing component; and thereafter fixing said second housing component to said first housing component with said emitter unit and said detector unit also in part housed in complementary, first and second, compartment-defining elements in said second housing component;

said method being further characterized by the step of so configuring said compartment-defining elements as to: (a) position said emitter unit in said first compartment with an emitter means in said unit aligned with a first infrared radiation passing aperture in said first component, and (b) position said detector unit in said second compartment in alignment with a second infrared radiation passing aperture in said second compartment and with an infrared radiation detector means of said unit oriented to intercept infrared radiation propagated from the emitter unit through said first and second apertures to said detector unit.

3. A method as defined in claim 2 in which said emitter unit and said detector unit are aligned in said first housing component by complementary surfaces of: (a) said emitter unit and said detector unit, and (b) wall means of said first and second housing compartments.

4. An infrared radiation detector unit which is a physically integrated combination of an infrared radiation sensitive detector means, an enclosure for said detector means, a printed circuit board, and an electrical heater means for maintaining said infrared radiation sensitive detector means at a selected operating temperature, said heater means comprising thick film heating elements on said printed circuit board and said printed circuit board comprising means for connecting said thick film heating elements across an electrical power supply.

5. An infrared radiation detector unit as defined in claim 4 in which the printed circuit board comprises circuit means for so reducing the impedance of electrical signals outputted by the infrared radiation-sensitive detector means as to reduce the susceptibility of said signals to contamination by electromagnetic interference.

6. An infrared radiation detector unit as defined in claim 4 which comprises heater circuit means for controlling the operation of said heater means, said heater circuit means comprising means for sensing the temperature of the infrared radiation-sensitive detector means, and said printed circuit board comprising means for electrically connecting said temperature sensing means to said heater circuit means.

7. An infrared radiation detector unit as defined in claim 4 in which the infrared radiation-sensitive detector means is mounted on said printed circuit board.

8. An infrared radiation detector unit as defined in claim 7 in which said infrared radiation-sensitive detector means comprises a reference detector, a data detector, a reference filter, and a data filter, said reference filter and said data filter being mounted on said printed circuit board in radiant energy intercepting relationship to said reference detector and said data detector.

9. An infrared radiation detector unit as defined in claim 8 in which said data detector and said reference detector are mounted on said printed circuit board in an orthogonal relationship by a support means having integral, normally extending, first and second legs; said reference detector being assembled to one of said first and second legs and said data detector being assembled to the other of said first and second legs.

10. An infrared radiation detector unit as defined in claim 9 in which said reference detector and said data detector are seated in recesses in said first and second legs and the reference and data filters are fixed to said first and second legs in overlying relationship to said reference and data detectors.

11. An infrared radiation detector unit as defined in claim 4 in which the enclosure comprises an open-sided casing and said printed circuit board is so assembled to said casing as to be a cover for the open side of said casing.

12. An infrared radiation detector unit as defined in claim 4 in which said printed circuit board is one component of an assembly which also includes reference and data detectors and a detector support means for mounting said data and reference detectors to said printed circuit board, said assembly being installed in said detector unit enclosure.

13. An infrared radiation detector unit as defined in claim 12 in which said assembly comprises reference and data filters fixed to the detector support means in infrared radiation-intercepting relationships with said reference and data detectors.

14. An infrared radiation detector unit as defined in claim 11 which comprises a beam splitter for resolving a beam of radiant energy propagated to the detector unit into two components comprised of energy of different wavelengths, for transmitting one of said components to one of said detectors, and for reflecting the second of the components to the other of said components, said beam splitter being mounted in said open sided casing.

15. A detector unit as defined in claim 11 which has an electrostatic shield surrounding said casing and said printed circuit board.

* * * * *